US008288432B2

(12) United States Patent
Page et al.

(10) Patent No.: US 8,288,432 B2
(45) Date of Patent: Oct. 16, 2012

(54) TETRAHYDROINDOLE DERIVATIVES AS NADPH OXIDASE INHIBITORS

(75) Inventors: Patrick Page, Savonni (FR); Mike Orchard, Oxon (GB); Laetitia Fioraso-Cartier, Fillinges (FR); Bianca Mottironi, Geneva (CH)

(73) Assignee: Genkyotex SA, Plan-les-Ouates (CH)

( * ) Notice: Subject to any disclaimer, the term of this patent is extended or adjusted under 35 U.S.C. 154(b) by 377 days.

(21) Appl. No.: 12/532,567

(22) PCT Filed: Mar. 28, 2008

(86) PCT No.: PCT/EP2008/053704
§ 371 (c)(1),
(2), (4) Date: Sep. 22, 2009

(87) PCT Pub. No.: WO2008/116926
PCT Pub. Date: Oct. 2, 2008

(65) Prior Publication Data
US 2010/0120749 A1 May 13, 2010

Related U.S. Application Data

(60) Provisional application No. 60/908,414, filed on Mar. 28, 2007.

(30) Foreign Application Priority Data

Jun. 4, 2007 (EP) .................................... 07109561

(51) Int. Cl.
*A61K 31/405* (2006.01)

(52) U.S. Cl. ........................................................ 514/415
(58) Field of Classification Search .................. 514/415
See application file for complete search history.

(56) References Cited

U.S. PATENT DOCUMENTS

| | | | |
|---|---|---|---|
| 3,931,407 A | 1/1976 | Allen et al. | |
| 4,909,827 A | 3/1990 | Gehring et al. | |
| 5,869,516 A | 2/1999 | Arlt et al. | |
| 6,624,309 B1 | 9/2003 | Lloyd et al. | |
| 2009/0099179 A1* | 4/2009 | Klein et al. | 514/235.2 |
| 2010/0048560 A1 | 2/2010 | Page et al. | |
| 2011/0172266 A1 | 7/2011 | Page et al. | |
| 2011/0178081 A1 | 7/2011 | Page et al. | |
| 2011/0178082 A1 | 7/2011 | Page et al. | |
| 2011/0269757 A1 | 11/2011 | Page et al. | |

FOREIGN PATENT DOCUMENTS

| | | |
|---|---|---|
| DE | 102005048897 | 10/2005 |
| EP | 0274642 A | 7/1988 |
| EP | 1505068 | 2/2005 |
| EP | 2002835 A | 12/2008 |
| WO | WO 2004-005267 | 1/2004 |
| WO | WO 2005-080378 | 9/2005 |
| WO | WO 2006-041874 | 4/2006 |
| WO | WO2006041874 * | 4/2006 |
| WO | WO 2008/113856 | 9/2008 |
| WO | WO 2010/035217 | 4/2010 |
| WO | WO 2010/035219 | 4/2010 |
| WO | WO 2010/035220 | 4/2010 |
| WO | WO 2010/035221 | 4/2010 |

OTHER PUBLICATIONS

Klein et al. CAS: 147: 427219, 2007.*
Slade et al. CAS: 144:412361, 2006.*
International Preliminary Search Report on Patentability for PCT/EP2008/053704 issued by the European Patent Office (74 pages), 2008.
Djordjevic, T., et al., "Human Urotensin II is a Novel Activator of NADPH Oxidase in Human Pulmonary Artery Smooth Muscle Cells," Arterioscler. Thromb. Vasc. Biol. 2005; 25; 519-525.
Hua, C., et al., "The vascular NAD(P)H oxidases as therapeutic targets in cardiovascular diseases", TRENDS in Pharmacological Sciences, vol. 24, No. 9, Sep. 2003.
Saxena, U, et al., "New approaches for treatment of diabetic nephropathy: the endothelium as a target for drug discovery", Expert Opin. Ther. Targets (2001) 5(5):539-545.
Thabut, G., et al., "Tumor Necrosis Factor-α Increases Airway Smooth Muscle Oxidants Production through a NADPH Oxidase-like System to Enhance Myosin Light Chain Phosphorylation and Contractility", Journal of Biological Chemistry, vol. 227, No. 25, Issue of Jun. 21, 2002, pp. 22814-22821.
Yang, S., et al., "Characterization of Interferon Gamma Receptors on Osteoclasts: Effect of Interferon Gamma on Osteoclastic Superoxide Generation", Jounal of Cellular Biochemistry 84:645-654, 2002.
Bedard, K. et al. "The NOX Family of ROS-Generating NADPH Oxidases: Physiology and Pathophysiology" *Physiological Reviews*, Jan. 2007, pp. 245-313, vol. 87.
Ferrara, N. et al. "Angiogenesis as a therapeutic target" *Nature*, Dec. 15, 2005, pp. 967-974, vol. 438.
Folkman, J. "Angiogenesis" *Annu. Rev. Med.*, 2006, pp. 1-18, vol. 57.
Griendling, K. K. et al. "NAD(P)H Oxidase: Role in Cardiovascular Biology and Disease" *Circulation Research*, 2000, pp. 494-501, vol. 86.
Ray, R. et al. "NADPH oxidase and endothelial cell function" *Clinical Science*, 2005, pp. 217-226, vol. 109.
Wu, D. et al. "NADPH oxidase mediates oxidative stress in the 1-methyl-4-phenyl-1,2,3,6-tetrahydropyridine model of Parkinson's disease" *PNAS*, May 13, 2003, pp. 6145-6150, vol. 100, No. 10.
Garrido-Urbani, S. et al. "Targeting Vascular NADPH Oxidase 1 Blocks Tumor Angiogenesis through a PPARα Mediated Mechanism" *PLoS ONE*, Feb. 2011, pp. 1-13, vol. 6, Issue 2.
Chang, G. et al. "Specific Inhibition of NADP(H) Oxidase (NOX) Abrogates the Tumorigenic Phenotype of Renal Cancer Cells" Poster at Annual Meeting of the Society of Basic Urology, Nov. 2009, New Orleans, USA, p. 1.
Jain, V. K. et al. "NADPH Oxidase and Myeloperoxidase Activity in Psoriasis Leukocytes" *The Journal of Dermatology*, 1985, pp. 425-428, vol. 12.

(Continued)

*Primary Examiner* — Rei-tsang Shiao
(74) *Attorney, Agent, or Firm* — Saliwanchik, Lloyd & Eisenschenk

(57) ABSTRACT

The present invention is related to tetrahydroindole derivatives of Formula (I), pharmaceutical composition thereof, methods of preparation thereof and to their use for the treatment and/or prophylaxis of disorders or conditions related to Nicotinamide adenine dinucleotide phosphate oxidase (NADPH Oxidase).

25 Claims, No Drawings

OTHER PUBLICATIONS

Baker, M. A. et al. "Reactive oxygen species in spermatozoa: methods for monitoring and significance for the origins of genetic disease and infertility" *Reproductive Biology and Endorcinology*, 2005, pp. 1-9, vol. 3, No. 67.

Chen, P. et al. "Role of NADPH oxidase and ANG II in diabetes-induced retinal leukostasis" *Am. J. Physiol. Reul. Integr. Comp. Physiol.*, 2007, pp. R1619-R1629, vol. 293.

Cucoranu, I. et al. "NAD(P)H Oxidase 4 Mediates Transforming Growth Factor-b1-Induced Differentiation of Cardiac Fibroblasts Into Myofibroblasts" *Circulation Research*, 2005, pp. 900-907, vol. 97.

El Benna, J. et al. "NADPH Oxidase Priming and p47phox Phosphorylation in Neutrophils from Synovial Fluid of Patients with Rheumatoid Arthritis and Spondylarthropathy" *Inflammation*, Dec. 2002, pp. 273-278, vol. 26, No. 6.

Ellis E. A. et al. "Time Course of NADH Oxidase, Inducible Nitric Oxide Synthase and Peroxynitrite in Diabetic Retinopathy in the BBZ/WOR Rat" *Nitric Oxide: Biology and Chemistry*, 2002, pp. 295-304, vol. 6, No. 3.

Fukuyama, M. et al. "Overexpression of a novel superoxide-producing enzyme, NADPH oxidase 1, in adenoma and well differentiated adenocarcinoma of the human colon" *Cancer Letters*, 2005, pp. 97-104, vol. 221.

Gavazzi, G. et al. "NOX1 Deficiency Protects from Aortic Dissection in Response to Angiotensin II" *Hypertension*, 2007, pp. 189-196, vol. 50.

Gukovskaya, A. S. et al. "Neutrophils and NADPH Oxidase Mediate Intrapancreatic Trypsin Activation in Murine Experimental Acute Pancreatitis" *Gastroenterology*, 2002, pp. 974-984, vol. 122.

Hausmann, M. et al. "Subtractive screening reveals up-regulation of NADPH oxidase expression in Crohn's disease intestinal macrophages" *Clin. Exp. Immunol.*, 2001, pp. 48-55, vol. 125.

Hoidal, J. R. et al. "The Role of Endogenous NADPH Oxidases in Airway and Pulmonary Vascular Smooth Muscle Function" *Antioxidants & Redox Signaling*, 2003, pp. 751-758, vol. 5.

Inoguchi, T. et al. "NAD(P)H Oxidase Activation: A Potential Target Mechanism for Diabetic Vascular Complications, Progressive β-Cell Dysfunction and Metabolic Syndrome" *Current Drug Targets*, 2005, pp. 495-501, vol. 6.

Jin, L. et al. "NADPH oxidase: recent evidence for its role in erectile dysfunction" *Asian J. Androl.*, Jan. 2008, pp. 6-13, vol. 10.

Kawai, Y. et al. "Relationship of Intracellular Calcium and Oxygen Radicals to Cisplatin-Related Renal Cell Injury" *J. Pharmacol. Sci.*, 2006, pp. 65-72, vol. 100.

Klees, R. F. et al. "Apocynin Derivatives Interrupt Intracellular Signaling Resulting in Decreased Migration in Breast Cancer Cells" *Journal of Biomedicine and Biotechnology*, 2006, pp. 1-10, vol. 2006.

Krijnen, P. A. et al. "Increased Nox2 expression in human cardiomyocytes after acute myocardial infarction" *J. Clin. Pathol.*, 2003, pp. 194-199, vol. 56.

Lanone S. et al. "Bilirubin decreases NOS2 expression via inhibition of NAD(P)H oxidase: implications for protection against endotoxic shock in rats" *The FASEB Journal*, 2005, pp. 1-26.

Lee, N. K. et al. "A crucial role for reactive oxygen species in RANKL-induced osteoclast differentiation" *Blood*, 2005, pp. 852-859, vol. 106.

Liu, Y. et al. "Suppression of Microglial Inflammatory Activity by Myelin Phagocytosis: Role of p47-PHOX-Mediated Generation of Reactive Oxygen Species" *The Journal of Neuroscience*, Dec. 13, 2006, pp. 12904-12913, vol. 26, No. 50.

Nibali, L. et al. "NADPH oxidase (CYBA) and FcγR polymorphisms as risk factors for aggressive periodontitis" *J. Clin. Periodontol*, 2006, pp. 529-539, vol. 33.

Patel, C. et al. "Prolonged Reactive Oxygen Species Generation and Nuclear Factor-κB Activation after a High-Fat, High-Carbohydrate Meal in the Obese" *The Journal of Clinical Endocrinology & Metabolism*, 2007, pp. 4476-4479, vol. 92, No. 111.

Patel, M. et al. "Activation of NADPH oxidase and extracellular superoxide production in seizure-induced hippocampal damage" *Journal of Neurochemistry*, 2005, pp. 123-131, vol. 92.

Hougee, S. et al. "Oral administration of the NADPH-oxidase inhibitor apocynin partially restores diminished cartilage proteoglycan synthesis and reduces inflammation in mice" *European Journal of Pharmacology*, 2006, pp. 264-269, vol. 531.

Qian, L. et al. "Sinomenine, a natural dextrorotatory morphinan analog, is anti-inflammatory and neuroprotective through inhibition of microglial NADPH oxidase" *Journal of Neuroinflammation*, 2007, pp. 1-14, vol. 4, No. 23.

Ritsick, D. R. et al. "Spring brings breezes, wheezes, and pollen oxidases" *The Journal of Clinical Investigation*, Aug. 2005, vol. 115, No. 8.

Sato, K. et al. "In vivo lipid-derived free radical formation by NADPH oxidase in acute lung injury induced by lipopolysaccharide: a model for ARDS" *FASEB J.*, 2002, pp. 1713-1720, vol. 16.

Satoh, M. et al. "NAD(P)H oxidase and uncoupled nitric oxide synthase are major sources of glomerular superoxide in rats with experimental diabetic nephropathy" *Am. J. Physiol Renal Physiol*, 2005, pp. F1144-F1152, vol. 288.

Sharma, K. et al. "TGF-β impairs renal autoregulation via generation of ROS" *Am. J. Physiol Renal Physiol*, 2005, pp. F1069-F1079, vol. 288.

Sirker, A. et al. "Involvement of NADPH Oxidases in Cardiac Remodelling and Heart Failure" *Am. J. Nephrol*, 2007, pp. 649-660, vol. 27.

Sonta, T. et al. "Evidence for Contribution of Vascular NAD(P)H Oxidase to Increased Oxidative Stress in Animal Models of Diabetes and Obesity" *Free Radical Biology & Medicine*, 2004, pp. 115-123, vol. 37, No. 1.

Vaquero, V. C. et al. "Reactive Oxygen Species Produced by NAD(P)H Oxidase Inhibit Apoptosis in Pancreatic Cancer Cells" *The Journal of Biological Chemistry*, Aug. 13, 2004, pp. 34643-34654, vol. 279, No. 33.

Kerbel, R. S. "Tumor Angiogenesis" *N. Engl J Med*, May 8, 2008, pp. 2039-2049, vol. 358.

Banfi, B. et al. "NOX3, a Superoxide-generating NADPH Oxidase of the Inner Ear" *The Journal of Biological Chemistry*, Oct. 29, 2004, pp. 46065-46072, vol. 279, No. 44.

Laleu, B. et al. "First in Class, Potent, and Orally Bioavailable NADPH Oxidase Isoform 4 (Nox4) Inhibitors for the Treatment of Idiopathic Pulmonary Fibrosis" *J. Med. Chem.*, 2010, pp. 7715-7730, vol. 53.

Lambeth, J. D. et al. "NOX enzymes as novel targets for drug development" *Semin Immunopathol*, 2008, pp. 1-25.

Rao, P. V. et al. "Expression of nonphagocytic NADPH oxidase system in the ocular lens" *Molecular Vision*, 2004, pp. 112-121, vol. 10.

Vendrov, A. E. et al. "NADPH Oxidases Regulate CD44 and Hyaluronic Acid Expression in Thrombin-treated Vascular Smooth Muscle Cells and in Atherosclerosis" *The Journal of Biological Chemistry*, Aug. 20, 2010, pp. 26545-26557, vol. 285, No. 34.

Sedeek, M. et al. "Critical role of Nox4-based NADPH oxidase in glucose-induced oxidative stress in the kidney: implications in type 2 diabetic nephropathy" *Am. J. Physiol. Renal Physiol.*, 2010, pp. F1348-F1358, vol. 229.

Cai, H. et al. "The vascular NAD(P)H oxidases as therapeutic targets in cardiovascular diseases" *TRENDS in Pharmacological Sciences*, Sep. 2003, pp. 471-478, vol. 24, No. 9.

Nunomura, A. et al. "Oxidative Damage Is the Earliest Event in Alzheimer Disease" *Journal of Neuropathology and Experimental Neurology*, Aug. 2001, pp. 759-767, vol. 60, No. 8.

Shi, Y. et al. "Increased NAD(P)H Oxidase and Reactive Oxygen Species in Coronary Arteries After Balloon Injury" *Arterioscler Thromb Vasc Biol.*, 2001, pp. 739-745, vol. 21.

Office Action dated Jun. 18, 2012 in U.S. Appl. No. 12/532,336.

Office Action dated Oct. 13, 2010 in U.S. Appl. No. 12/532,336.

Office Action dated Mar. 29, 2011 in U.S. Appl. No. 12/532,336.

Cancer [online], retrieved on Jul. 6, 2007, retrieved from the Internet, URL: http://www.nim.nih.gov/medlineplus/cancer.html, pp. 1-10.

Junker, L. M. et al. "High-Throughput Screens for Small-Molecule Inhibitors of *Pseudomonas aeruginosa* Biofilm Development" *Antimicrobial Agents and Chemotherapy*, Oct. 2007, pp. 3582-3590, vol. 51, No. 10.

Dornow, A. et al. "Darstellung and Umsetzung einiger substituierter 3-Nitro-pyridine" *Chem. Ber.*, 1966, pp. 244-253, vol. 99.

Ellis, E. A. et al. "Increased H$_2$O$_2$, Vascular Endothelial Growth Factor and Receptors in the Retina of the BBZ/WOR Diabetic Rat" *Free Radical Biology & Medicine*, 2000, pp. 91-191, vol. 28, No. 1.
Chemcats Accession No. 2029347921, Jun. 13, 2008, XP-002514328, p. 1.
Written Opinion in International Application No. PCT/IB2009/054148, Oct. 12, 2009, pp. 1-8.
Office Action dated Apr. 17, 2012 in U.S. Appl. No. 13/120,436.
Database CA [Online] Chemical Abstracts Service, Accession No. 2007:341007, 2007, XP-002558729, p. 1, 2007.
Database CA [Online] Chemical Abstracts Service, Accession No. 2004:14711, 2003, XP-002558730, pp. 1-2, 2004.
Written Opinion in International Application No. PCT/IB2009/054156, Mar. 3, 2010, pp. 1-10.
Ushio-Fukai, M. et al. "Reactive oxygen species and angiogenesis: NADPH oxidase as target for cancer therapy" *Cancer Letters*, 2008, pp. 37-52, vol. 266.
Chemcats Accession No. 2049339652, Jun. 13, 2008, XP-002514424, pp. 1-6.
Office Action dated Apr. 16, 2012 in U.S. Appl. No. 13/120,438.
Written Opinion in International Application No. PCT/IB2009/054155, Nov. 6, 2010, pp. 1-7.
Lala, P. K. et al. "Role of nitric oxide in tumor progression: Lessons from experimental tumors" *Cancer and Metastasis Reviews*, 1998, pp. 91-106, vol. 17.
Golub, T. R. et al. "Molecular Classification of Cancer: Class Discovery and Class Prediction by Gene Expression Monitoring" *Science*, Oct. 15, 1999, pp. 531-537, vol. 286.
Wolff, M. E. et al. "Burger's Medicinal Chemistry and Drug Discovery", 1994 Wiley-Interscience, Fifth Edition, vol. I: Principles and Practice, pp. 975-977.
"Derivative." Merriam-Webster Online Dictionary, 2010, accessed Apr. 20, 2010, http://merriam-webster.com/dictionary/derivative.
Written Opinion in International Application No. PCT/EP2008/053390, Jul. 21, 2008, pp. 1-6.
Written Opinion in International Application No. PCT/IB2009/054150, Oct. 13, 2010, pp. 1-11.
Abdelrahman, M. et al. "Inhibitors of NADPH Oxidase Reduce the Organ Injury in Hemorrhagic Shock" *Shock*, 2005, pp. 107-114, vol. 23, No. 2.
Anantharam, V. et al. "Pharmacological inhibition of neuronal NADPH oxidase protects against 1-methyl-4-phenylpyridinium (MPP$^+$)-induced oxidative stress and apoptosis in mesencephalic dopaminergic neuronal cells" *NeuroToxicology*, 2007, pp. 988-997, vol. 28.
Puntambekar, P. et al. "Essential Role of Rac1/NADPH oxidase in nerve growth factor induction of TRPV1 expression" *Journal of Neurochemistry*, 2005, pp. 1689-1703, vol. 95.
Sturrock, A. et al. "Nox4 mediates TGF-β1-induced retinoblastoma protein phosphorylation, proliferaton, and hypertrophy in human airway smooth muscle cells" *Am. J Physiol. Lung. Cell Mol. Physiol.*, 2007, pp. L1543-L1555. vol. 292, No. 6.
Wu, D.-C. et al. "The inflammatory NADPh oxidase enzyme modulates motor neuron degeneration in amyotrophic lateral sclerosis mice" *PNAS*, Aug. 8, 2006, pp. 12132-12137, vol. 103, No. 32.
Klein, C. et al. CAS:147:427219, 2007, Accession No. 2007:1146277, pp. 1-4, 2007.
Slade, R. et al. CAS:144:412361, 2006, Accession No. 2006:361235, pp. 1-4, 2006.

\* cited by examiner

TETRAHYDROINDOLE DERIVATIVES AS NADPH OXIDASE INHIBITORS

CROSS-REFERENCE TO RELATED APPLICATION

This application is a National Stage filing of PCT International Application Serial No. PCT/IB2008/053704, filed Mar. 28, 2008, which claims the benefit of U.S. Provisional Application Ser. No. 60/908,414, filed Mar. 28, 2007, and European Application No. EP 07109561.6, filed Jun. 6, 2007, the disclosures each of which are expressly incorporated herein by reference.

FIELD OF THE INVENTION

The present invention relates to tetrahydroindole derivatives of Formula (I), pharmaceutical composition thereof, methods of preparation thereof and to their use for the preparation of a medicament for the treatment and/or prophylaxis of cardiovascular diseases, respiratory disorders, disorders affecting the metabolism, skin and/or bone diseases, neuromuscular degenerative diseases, kidney diseases, reproduction disorders, inflammatory disorders and cancers. Specifically, the present invention is related to tetrahydroindole derivatives useful for the preparation of a pharmaceutical formulation for the modulation, notably the inhibition of the activity or function of the Nicotinamide adenine dinucleotide phosphate oxidase (NADPH Oxidase).

BACKGROUND OF THE INVENTION

NADPH oxidases (NOX) are proteins that transfer electrons across biological membranes. In general, the electron acceptor is oxygen and the product of the electron transfer reaction is superoxide. The biological function of NOX enzymes is therefore the generation of reactive oxygen species (ROS) from oxygen. Reactive oxygen species (ROS) are oxygen-derived small molecules, including oxygen radicals (super oxide anion [$.O_2^-$], hydroxyl [HO.], peroxyl [ROO.], alkoxyl [RO.] and hydroperoxyl [HOO.]) and certain non-radicals that are either oxidizing agents and/or are easily converted into radicals. Nitrogen-containing oxidizing agents, such as nitric oxide are also called reactive nitrogen species (RNS). ROS generation is generally a cascade of reactions that starts with the production of superoxide. Superoxide rapidly dismutates to hydrogen peroxide either spontaneously, particularly at low pH or catalyzed by superoxide dismutase. Other elements in the cascade of ROS generation include the reaction of superoxide with nitric oxide to form peroxynitrite, the peroxidase-catalyzed formation of hypochlorous acid from hydrogen peroxide, and the iron-catalyzed Fenton reaction leading to the generation of hydroxyl radical.

ROS avidly interact with a large number of molecules including other small inorganic molecules as well as DNA, proteins, lipids, carbohydrates and nucleic acids. This initial reaction may generate a second radical, thus multiplying the potential damage. ROS are involved not only in cellular damage and killing of pathogens, but also in a large number of reversible regulatory processes in virtually all cells and tissues. However, despite the importance of ROS in the regulation of fundamental physiological processes, ROS production can also irreversibly destroy or alter the function of the target molecule. Consequently, ROS have been increasingly identified as major contributors to damage in biological organisms, so-called "oxidative stress".

During inflammation, NADPH oxidase is one of the most important sources of ROS production in vascular cells under inflammatory conditions (Thabut et al, 2002, *J. Biol. Chem.*, 277:22814-22821).

In the lung, tissues are constantly exposed to oxidants that are generated either endogenously by metabolic reactions (e.g. by mitochondrial respiration or activation of recruited inflammatory cells) or exogenously in the air (e.g. cigarette smoke or air pollutants). Further, the lungs, constantly exposed to high oxygen tensions as compared to other tissues, have a considerable surface area and blood supply and are particularly susceptible to injury mediated by ROS (Brigham, 1986, *Chest*, 89(6): 859-863). NADPH oxidase-dependent-ROS generation has been described in pulmonary endothelial cells and smooth muscle cells. NADPH oxidase activation in response to stimuli has been thought to be involved in the development of respiratory disorders such as pulmonary hypertension and enhancement of pulmonary vasoconstriction (Djordjevic et al, 2005, *Arterioscler. Thromb. Vase. Biol,* 25, 519-525; Liua et al, 2004, *Am. J. Physiol Lung, Cell Mol. Physiol,* 287: L111-118). Further, pulmonary fibrosis has been characterized by lung inflammation and excessive generation of ROS.

Osteoclasts which are macrophage-like cells that play a crucial role in bone turn-over (e.g. bone resorption) generate ROS through NADPH oxidase-dependant mechanisms (Yang et al, 2002, *J. Cell. Chem.* 84, 645-654).

Diabetes is known to increase oxidative stress (e.g. increased generation of ROS by auto-oxidation of glucose) both in humans and animals and increased oxidative stress has been said to play an important role in the development of diabetic complications. It has been shown that increased peroxide localization and endothelial cell dysfunction in the central retina of diabetic rats coincides with the areas of NADPH oxidase activity in the retinal endothelial cells (Ellis et al, 2000, *Free Rad. Biol. Med.,* 28:91-101). Further, it has been suggested that controlling oxidative stress (ROS) in mitochondria and/or inflammation may be a beneficial approach for the treatment of diabetes (Pillarisetti et al, 2004, *Expert Opin. Ther. Targets,* 8(5):401-408).

ROS are also strongly implicated in the pathogenesis of atherosclerosis, cell proliferation, hypertension and reperfusion injury cardiovascular diseases in general (Cai et al., 2003, *Trends Pharmacol. Sci,* 24:471-478). Not only is superoxide production, for example in the arterial wall, increased by all risk factors for atherosclerosis, but ROS also induce many "proatherogenic" in vitro cellular responses. An important consequence of the formation of ROS in vascular cells is the consumption of nitric oxide (NO). NO inhibits the development of vascular diseases, and loss of NO is important in the pathogenesis of cardiovascular diseases. The increase in NADPH oxidase activity in vascular wall after balloon injury has been reported (Shi et al, 2001, *Throm. Vase. Biol,* 2001, 21, 739-745)

It is believed that oxidative stress or free radical damage is also a major causative factor in neuromuscular degenerative diseases. Such damages may include mitochondrial abnormalities, neuronal demyelination, apoptosis, and neuronal death leading to the development of progressive neuromuscular degenerative diseases.

Further, the generation of ROS by sperm has been demonstrated in a large number of species and has been suggested to be attributed to an NADPH oxidase within spermatozoa (Vernet et al, *Biol. Reprod.,* 2001, 65:1102-1113). Excessive ROS generation has been suggested to be implicated in sperm pathology, including male infertility and also in some penile disorders and prostate cancer.

NADPH oxidases are multi-subunit enzymes made up of a membrane-bound cytochrome b558 domain and three cytosolic protein subunits, p47phox, p67phox and a small GTPase, Rac. Seven isoforms of NOX enzymes have been identified including NOX1, NOX2, NOX3, NOX4, NOX5, DUOX1 and DUOX2 (Leto et al, 2006, *Antioxid Redox Signal,* 8(9-10): 1549-61; Cheng et al, 2001, *Gene,* 16; 269(1-2):131-40).

Tetrahydroindoles have been described to be useful in the treatment of neural disorders due to amyloid or tangles deposits, such as Alzheimer's disease, dementia and cognitive impairment (WO 2006/041874).

Thus, ROS derived from NADPH contribute to the pathogenesis of numerous diseases, especially cardiovascular diseases or disorders, respiratory disorder or disease, disease or disorder affecting the metabolism, bone disorders, neuromuscular degenerative diseases, inflammatory diseases, reproduction disorder or disease, pain, cancer and disease or disorders of the gastrointestinal system. Therefore, it would be highly desirable to develop new active agents focusing on the ROS signalling cascade, especially on NADPH oxidases (NOX).

SUMMARY OF THE INVENTION

The present invention is directed towards new molecules useful in the treatment and/or prophylaxis of Nicotinamide adenine dinucleotide phosphate oxidase (NADPH Oxidase) related disorders such as cardiovascular diseases, respiratory disorders, disorders affecting the metabolism, skin and/or bone diseases, neuromuscular degenerative diseases, kidney diseases, reproduction disorders, inflammatory disorders, allergic disorders, traumatisms, septic, hemorrhagic and anaphylactic shock, cancers, a diseases or disorders of the gastrointestinal system and other diseases and/or disorders associated with Nicotinamide adenine dinucleotide phosphate oxidase (NADPH Oxidase). Notably, the invention is related to new molecules useful in the inhibition or reduction of ROS production in cells.

A first aspect of the invention provides a use of a tetrahydroindole derivative according to Formula (I) wherein d, $G_2$, $G_3$, $A_1$; $A_2$, $A_3$, $A_4$, $B_1$, $B_2$, $B_3$, $D_1$, $D_2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are as defined in the detailed description; as well as pharmaceutically acceptable salts and pharmaceutically active derivative and tautomers thereof for the preparation of a medicament for the treatment or prophylaxis of a disease or condition selected from cardiovascular diseases, respiratory disorders, disorders affecting the metabolism, skin and/or bone diseases, neuromuscular degenerative diseases, kidney diseases, reproduction disorders, inflammatory disorders, allergic disorders, traumatisms, septic, hemorrhagic and anaphylactic shock, cancers, a diseases or disorders of the gastrointestinal system and other diseases and/or disorders associated with Nicotinamide adenine dinucleotide phosphate oxidase (NADPH Oxidase).

A second aspect of the invention relates to a method for treating a patient suffering from a disease or condition selected from cardiovascular diseases, respiratory disorders, disorders affecting the metabolism, skin and/or bone diseases, neuromuscular degenerative diseases, kidney diseases, reproduction disorders, inflammatory disorders, allergic disorders, traumatisms, septic, hemorrhagic and anaphylactic shock, cancers, a diseases or disorders of the gastrointestinal system and other diseases and/or disorders associated with Nicotinamide adenine dinucleotide phosphate oxidase (NADPH Oxidase). The method comprises administering a compound according to Formula (I) in a patient in need thereof.

A third aspect of the invention provides a tetrahydroindole derivative according to Formula (I) wherein $G_1$, $G_2$, $G_3$, $A_1$, $A_2$, $A_3$, $A_4$, $B_1$, $B_2$, $B_3$, $D_1$, $D_2$, $R^1$, $R^2$, $R^3$, $R^4$, $R^5$, $R^6$, $R^7$, $R^8$, $R^9$, $R^{10}$, $R^{11}$, $R^{12}$, $R^{14}$ and $R^{15}$ are as defined in the detailed description; $R^{13}$ is selected from optionally substituted alkenyl; optionally substituted alkynyl; optionally substituted amino alkyl; optionally substituted $C_3$-$C_8$-cycloalkyl; optionally substituted heterocycloalkyl; optionally substituted aryl; optionally substituted heteroaryl; optionally substituted alkyl aryl; optionally substituted alkyl heteroaryl; optionally substituted aryl alkyl; optionally substituted heteroaryl alkyl; optionally substituted alkyl $C_3$-$C_8$-cycloalkyl; optionally substituted alkyl heterocycloalkyl; optionally substituted $C_3$-$C_8$-cycloalkyl alkyl and optionally substituted heterocycloalkyl alkyl; as well as pharmaceutically acceptable salts and pharmaceutically active derivative and tautomers thereof for use as a medicament.

A fourth aspect of the invention provides a tetrahydroindole derivative according to Formula (I) wherein $G_1$, $G_2$, $G_3$, $A_1$, $A_2$, $A_3$, $A_4$, $B_1$, $B_2$, $B_3$, $D_1$, $D_2$, $R^1$, $R^2$, $R^3$, $R^4$, $R^5$, $R^6$, $R^7$, $R^8$, $R^9$, $R^{10}$, $R^{11}$, $R^{12}$ and $R^{15}$ are defined in the detailed description $R^{14}$ is H and $R^{13}$ is selected from optionally substituted non fused aryl and optionally substituted heteroaryl; as well as pharmaceutically acceptable salts and pharmaceutically active derivative and tautomers thereof; as well as pharmaceutically acceptable salts and pharmaceutically active derivative and tautomers thereof.

A fifth aspect of the invention provides a tetrahydroindole derivative according to Formula (I) wherein $G_1$, $G_2$, $G_3$, $A_1$, $A_2$, $A_3$, $A_1$, $B_1$, $B_2$, $B_3$, $D_1$, $D_2$, $R^1$, $R^2$, $R^3$, $R^4$, $R^5$, $R^6$, $R^7$, $R^5$, $R^9$, $R^{10}$, $R^{11}$, $R^{12}$ and $R^{15}$ are as defined in the detailed description; $R^{13}$ and $R^{14}$ are independently selected from optionally substituted alkyl; optionally substituted alkenyl; optionally substituted alkynyl; optionally substituted amino alkyl; optionally substituted $C_3$-$C_8$-cycloalkyl; optionally substituted heterocycloalkyl; optionally substituted aryl; optionally substituted heteroaryl; optionally substituted alkyl aryl; optionally substituted alkyl heteroaryl; optionally substituted aryl alkyl; optionally substituted heteroaryl alkyl; optionally substituted alkyl $C_3$-$C_8$-cycloalkyl; optionally substituted alkyl heterocycloalkyl; optionally substituted $C_3$-$C_8$-cycloalkyl alkyl and optionally substituted heterocycloalkyl alkyl; as well as pharmaceutically acceptable salts and pharmaceutically active derivative and tautomers thereof.

A sixth aspect of the invention provides a tetrahydroindole derivative according to Formula (I) wherein $G_1$ is selected from the following groups:

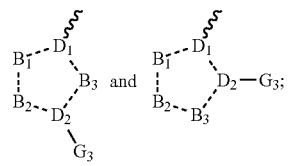

and wherein $G_2$, $G_3$, $B_1$, $B_2$, $B_3$, $D_1$, $D_2$, $R^1$, $R^2$, $R^3$, $R^4$, $R^5$, $R^6$, $R^7$, $R^5$, $R^9$, $R^{11}$, $R^{12}$, $R^{13}$, $R^{14}$ and $R^{15}$ are as defined in the detailed description; as well as pharmaceutically acceptable salts and pharmaceutically active derivative and tautomers thereof.

A seventh aspect of the invention relates to a pharmaceutical composition containing at least one derivative according to the invention and a pharmaceutically acceptable carrier, diluent or excipient thereof.

An eighth aspect of the invention relates to a tetrahydroindole derivative according to the invention for use as a medicament.

A ninth aspect of the invention relates to a tetrahydroindole derivative according to the invention for use in the treatment or prophylaxis of a disease or condition selected from cardiovascular diseases, respiratory disorders, disorders affecting the metabolism, skin and/or bone diseases, neuromuscular degenerative diseases, kidney diseases, reproduction disorders, inflammatory disorders, allergic disorders, traumatisms, septic, hemorrhagic and anaphylactic shock, cancers, a diseases or disorders of the gastrointestinal system and other diseases and/or disorders associated with Nicotinamide adenine dinucleotide phosphate oxidase (NADPH Oxidase).

Other features and advantages of the invention will be apparent from the following detailed description.

DETAILED DESCRIPTION OF THE INVENTION

The following paragraphs provide definitions of the various chemical moieties that make up the compounds according to the invention and are intended to apply uniformly throughout the specification and claims, unless an otherwise expressly set out definition provides a broader definition.

The term "alkyl" when used alone or in combination with other terms, comprises a straight chain or branched $C_1$-$C_{20}$ alkyl which refers to monovalent alkyl groups having 1 to 20 carbon atoms. This term is exemplified by groups such as methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, n-heptyl, 2-methylhexyl, 3-methylhexyl, 4-methylhexyl, 5-methylhexyl, n-heptyl, n-octyl, n-nonyl, n-decyl, tetrahydrogeranyl, n-dodecyl, n-tridecyl, n-tetradecyl, n-pentadecyl, n-hexadecyl, n-octadecyl, n-nonadecyl, and n-eicosanyl and the like. Preferably, these include $C_1$-$C_9$ alkyl, more preferably $C_1$-$C_6$ alkyl, especially preferably $C_1$-$C_4$ alkyl, which, by analogy, refer respectively to monovalent alkyl groups having 1 to 9 carbon atoms, monovalent alkyl groups having 1 to 6 carbon atoms and monovalent alkyl groups having 1 to 4 carbon atoms.

The term "alkenyl" when used alone or in combination with other terms, comprises a straight chain or branched $C_2$-$C_{20}$ alkenyl. It may have any available number of double bonds in any available positions, and the configuration of the double bond may be the (E) or (Z) configuration. This term is exemplified by groups such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 1-heptenyl, 1-octenyl, geranyl, 1-decenyl, 1-tetradecenyl, 1-octadecenyl, 9-octadecenyl, 1-eicosenyl, and 3,7,11,15-tetramethyl-1-hexadecenyl, and the like. Preferably, these include $C_2$-$C_8$ alkenyl, more preferably $C_2$-$C_6$ alkenyl. Among others, especially preferred are vinyl or ethenyl (—CH=$CH_2$), n-2-propenyl (allyl, —$CH_2$CH=$CH_2$), isopropenyl, 1-propenyl, 2-methyl-1-propenyl, 1-butenyl, 2-butenyl, and 3-methyl-2-butenyl and the like.

The term "alkynyl" when used alone or in combination with other terms, comprises a straight chain or branched $C_2$-$C_{20}$ alkynyl. It may have any available number of triple bonds in any available positions. This term is exemplified by groups such as alkynyl groups that may have a carbon number of 2-20, and optionally a double bond, such as ethynyl (—C≡CH), 1-propynyl, 2-propynyl (propargyl: —$CH_2$C≡CH), 2-butynyl, 2-pentene-4-ynyl, and the like. Preferably, these include $C_2$-$C_6$ alkynyl, more preferably $C_2$-$C_6$ alkynyl and the like.

The term "heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl and the like.

The term "aryl" refers to an unsaturated aromatic carbocyclic group of from 6 to 14 carbon atoms having a single ring (e.g., phenyl) or multiple condensed rings (e.g., indenyl, naphthyl). Aryl include phenyl, naphthyl, anthryl, phenanthrenyl and the like.

The term "alkyl aryl" refers to aryl groups having an alkyl substituent, including methyl phenyl, ethyl phenyl and the like.

The term "aryl alkyl" refers to alkyl groups having an aryl substituent, including 3-phenylpropanyl, benzyl and the like.

The term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

The term "alkyl heteroaryl" refers to heteroaryl groups having an alkyl substituent, including methyl furyl and the like.

The term "heteroaryl alkyl" refers to alkyl groups having a heteroaryl substituent, including furyl methyl and the like.

The term "alkenyl aryl" refers to an aryl groups having an alkenyl substituent, including vinyl phenyl and the like.

The term "aryl alkenyl" refers to an alkenyl groups having an aryl substituent, including phenyl vinyl and the like.

The term "alkenyl heteroaryl" refers to heteroaryl groups having an alkenyl substituent, including vinyl pyridinyl and the like.

The term "heteroaryl alkenyl" refers to alkenyl groups having a heteroaryl substituent, including pyridinyl vinyl and the like.

The term "$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl includes cyclopentyl, cyclohexyl, norbornyl and the like.

The term "heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidinyl, piperidinyl, piperazinyl, morpholinyl, tetrahydrofuranyl and the like.

The term "alkyl $C_3$-$C_8$-cycloalkyl" refers to $C_3$-$C_8$-cycloalkyl groups having an alkyl substituent, including methyl cyclopentyl and the like.

The term "C$_3$-C$_8$-cycloalkyl alkyl" refers to alkyl groups having a C$_3$-C$_8$-cycloalkyl substituent, including 3-cyclopentyl propyl and the like.

The term "alkyl heterocycloalkyl" refers to heterocycloalkyl groups having an alkyl substituent, including 4-methylpiperidinyl and the like.

The term "heterocycloalkyl alkyl" refers to alkyl groups having a heterocycloalkyl substituent, including (1-methylpiperidin-4-yl)methyl and the like.

The term "carboxy" refers to the group —C(O)OH.

The term "carboxy alkyl" refers to alkyl groups having a carboxy substituent, including 2-carboxyethyl and the like.

The term "acyl" refers to the group —C(O)R where R includes H, "alkyl," "aryl," "heteroaryl," "C$_3$-C$_8$-cycloalkyl," "heterocycloalkyl," "aryl alkyl," "heteroaryl alkyl," "C$_3$-C$_8$-cycloalkyl alkyl" or "heterocycloalkyl alkyl", including acetyl and the like.

The term "acyl alkyl" to alkyl groups having an acyl substituent, including 2-acetylethyl and the like.

The term "acyl aryl" refers to aryl groups having an acyl substituent, including 2-acetylphenyl and the like.

The term "acyloxy" refers to the group —OC(O)R where R includes H, "alkyl", "alkenyl," "alkynyl," "C$_3$-C$_8$-cycloalkyl," "heterocycloalkyl," "aryl," "heteroaryl," "aryl alkyl," "heteroaryl alkyl," "aryl alkenyl," "heteroaryl alkenyl," "aryl alkynyl," "heteroaryl alkynyl," "C$_3$-C$_8$-cycloalkyl alkyl," or "heterocycloalkyl alkyl", including acetyloxy and the like.

The term "acyloxy alkyl" refers to alkyl groups having an acyloxy substituent, including 2-(ethylcarbonyloxy)ethyl and the like.

The term "alkoxy" refers to the group —O—R where R includes "alkyl," "aryl," "heteroaryl," "aryl alkyl" or "heteroaryl alkyl". Preferred alkoxy groups include for example, methoxy, ethoxy, phenoxy and the like.

The term "alkoxy alkyl" refers to alkyl groups having an alkoxy substituent, including methoxyethyl and the like.

The term "alkoxycarbonyl" refers to the group —C(O)OR where R includes "alkyl", "aryl", "heteroaryl", "aryl alkyl", "heteroaryl alkyl" or "heteroalkyl", including methoxycarbonyl and the like.

The term "alkoxycarbonyl alkyl" refers to alkyl groups having an alkoxycarbonyl substituent, including 2-(benzyloxycarbonyl)ethyl and the like.

The term "aminocarbonyl" refers to the group —C(O)NRR' where R and R' are independently H, alkyl, aryl, heteroaryl, "aryl alkyl" or "heteroaryl alkyl," including N-phenyl carbonyl and the like.

The term "aminocarbonyl alkyl" refers to alkyl groups having an aminocarbonyl substituent, including 2-(dimethylaminocarbonyl)ethyl, N-ethylacetamidyl, N,N-Diethylacetamidyl and the like.

The term "acylamino" refers to the group —NRC(O)R' where R and R' are independently H, "alkyl," "alkenyl," "alkynyl," "C$_3$-C$_8$-cycloalkyl," "heterocycloalkyl," "aryl," "heteroaryl," "aryl alkyl," "heteroaryl alkyl," "aryl alkenyl," "heteroaryl alkenyl," "aryl alkynyl," "heteroaryl alkynyl," "cycloalkyl alkyl," or "heterocycloalkyl alkyl", including acetylamino and the like.

The term "acylamino alkyl" refers to alkyl groups having an acylamino substituent, including 2-(propionylamino)ethyl and the like.

The term "ureido" refers to the group —NRC(O)NR'R" where R, R' and R" are independently H, "alkyl," "alkenyl," "alkynyl," "C$_3$-C$_8$-cycloalkyl," "heterocycloalkyl," "aryl," "heteroaryl," "aryl alkyl," "heteroaryl alkyl," "aryl alkenyl," "heteroaryl alkenyl," "aryl alkynyl," "heteroaryl alkynyl," "cycloalkyl alkyl," or "heterocycloalkyl alkyl," and where R' and R", together with the nitrogen atom to which they are attached, can optionally form a 3-8-membered heterocycloalkyl ring.

The term "ureido alkyl" refers to -alkyl groups having an ureido substituent, including 2-(N'-methylureido)ethyl and the like.

The term "carbamate" refers to the group —NRC(O)OR' where R and R' are independently "alkyl," "alkenyl," "alkynyl," "C$_3$-C$_8$-cycloalkyl," "heterocycloalkyl," "aryl," "heteroaryl," "alkyl aryl," "heteroaryl alkyl," "aryl alkenyl," "heteroaryl alkenyl," "aryl alkynyl," "heteroaryl alkynyl," "cycloalkyl alkyl," or "heterocycloalkyl alkyl" and optionally R can also be hydrogen.

The term "amino" refers to the group —NRR' where R and R' are independently H, "alkyl," "aryl," "heteroaryl," "alkyl aryl," "alkyl heteroaryl," "cycloalkyl," or "heterocycloalkyl," and where R and R', together with the nitrogen atom to which they are attached, can optionally form a 3-8-membered heterocycloalkyl ring.

The term "amino alkyl" refers to alkyl groups having an amino substituent, including 2-(1-pyrrolidinyl)ethyl and the like.

The term "ammonium" refers to a positively charged group —N$^+$RR'R" where R, R' and R" are independently "alkyl," "alkyl aryl," "alkyl heteroaryl," "cycloalkyl," or "heterocycloalkyl," and where R and R', together with the nitrogen atom to which they are attached, can optionally form a 3-8-membered heterocycloalkyl ring.

The term "ammonium alkyl" refers to alkyl groups having an ammonium substituent, including 1-ethylpyrrolidinium and the like.

The term "halogen" refers to fluoro, chloro, bromo and iodo atoms.

The term "sulfonyloxy" refers to a group —OSO$_2$—R wherein R is selected from "alkyl," "alkyl" substituted with halogens, e.g., an —OSO$_2$—CF$_3$ group, "alkenyl," "alkynyl," "C$_3$-C$_8$-cycloalkyl," "heterocycloalkyl," "aryl," "heteroaryl," "aryl alkyl," "heteroaryl alkyl," "aryl alkenyl," "heteroaryl alkenyl," "aryl alkynyl," "heteroaryl alkynyl," "cycloalkyl alkyl," or "heterocycloalkyl alkyl".

The term "sulfonyloxy alkyl" refers to alkyl groups having a sulfonyloxy substituent, including 2-(methylsulfonyloxy)ethyl and the like.

The term "sulfonyl" refers to group "—SO$_2$—R" wherein R is selected from "aryl," "heteroaryl," "alkyl," "alkyl" substituted with halogens, e.g., an —SO$_2$—CF$_3$ group, "alkenyl," "alkynyl," "C$_3$-C$_8$-cycloalkyl," "heterocycloalkyl," "aryl," "heteroaryl," "aryl alkyl," "heteroaryl alkyl," "aryl alkenyl," "heteroaryl alkenyl," "aryl alkynyl," "heteroaryl alkynyl," "cycloalkyl alkyl," or "heterocycloalkyl alkyl".

The term "sulfonyl alkyl" refers to alkyl groups having a sulfonyl substituent, including 2-(methylsulfonyl)ethyl and the like.

The term "sulfinyl" refers to a group "—S(O)—R" wherein R is selected from "alkyl," "alkyl" substituted with halogens, e.g., a —SO—CF$_3$ group, "alkenyl," "alkynyl," "C$_3$-C$_8$-cycloalkyl," "heterocycloalkyl," "aryl," "heteroaryl," "aryl alkyl," "heteroaryl alkyl," "aryl alkenyl," "heteroaryl alkenyl," "aryl alkynyl," "heteroaryl alkynyl," "C$_3$-C$_8$-cycloalkyl alkyl," or "heterocycloalkyl alkyl".

The term "sulfinyl alkyl" refers to alkyl groups having a sulfinyl substituent, including 2-(methylsulfinyl)ethyl and the like.

The term "sulfanyl" refers to groups —S—R where R includes H, "alkyl," "alkyl" substituted with halogens, e.g., a —S—CF$_3$ group, "alkenyl," "alkynyl," "C$_3$-C$_8$-cycloalkyl,"

"heterocycloalkyl," "aryl," "heteroaryl," "aryl alkyl," "heteroaryl alkyl," "aryl alkenyl," "heteroaryl alkenyl," "aryl alkynyl," "alkynylheteroaryl," "cycloalkyl alkyl," or "heterocycloalkyl alkyl". Preferred sulfanyl groups include methylsulfanyl, ethylsulfanyl, and the like.

The term "sulfanyl alkyl" refers to $C_1$-$C_8$-alkyl groups having a sulfanyl substituent, including 2-(ethylsulfanyl)ethyl and the like.

The term "sulfonylamino" refers to a group —$NRSO_2$—R' where R and R' are independently "alkyl," "alkenyl," "alkynyl," "$C_3$-$C_8$-cycloalkyl," "heterocycloalkyl," "aryl," "heteroaryl," "aryl alkyl", "heteroaryl alkyl," "aryl alkenyl," "heteroaryl alkenyl," "aryl alkynyl," "heteroaryl alkynyl," "$C_3$-$C_8$-cycloalkyl alkyl," or "heterocycloalkyl alkyl".

The term "sulfonylamino alkyl" refers to alkyl groups having a sulfonylamino substituent, including 2-(ethylsulfonylamino)ethyl and the like.

The term "aminosulfonyl" refers to a group —$SO_2$—NRR' where R and R' are independently H, "alkyl," "alkenyl," "alkynyl," "$C_3$-$C_8$-cycloalkyl," "heterocycloalkyl," "aryl," "heteroaryl," "aryl alkyl", "heteroaryl alkyl," "aryl alkenyl," "heteroaryl alkenyl," "aryl alkynyl," "heteroaryl alkynyl," "$C_3$-$C_8$-cycloalkyl alkyl," or "heterocycloalkyl alkyl", and where R and R', together with the nitrogen atom to which they are attached, can optionally form a 3-8-membered heterocycloalkyl ring. Aminosulfonyl groups include cyclohexylaminosulfonyl, piperidinylsulfonyl and the like.

The term "aminosulfonyl alkyl" refers to alkyl groups having an aminosulfonyl substituent, including 2-(cyclohexylaminosulfonyl)ethyl and the like.

Unless otherwise constrained by the definition of the individual substituent, the term "substituted" refers to groups substituted with from 1 to 5 substituents selected from the group consisting of "alkyl," "alkenyl," "alkynyl," "$C_3$-$C_8$-cycloalkyl," "heterocycloalkyl," "alkyl aryl," "alkyl heteroaryl," "alkyl cycloalkyl," "alkyl heterocycloalkyl," "amino," "aminosulfonyl," "ammonium," "acyl amino," "amino carbonyl," "aryl," "heteroaryl," "sulfinyl," "sulfonyl," "alkoxy," "alkoxy carbonyl," "carbamate," "sulfanyl," "halogen," trihalomethyl, cyano, hydroxy, mercapto, nitro, and the like.

The term "pharmaceutically acceptable salts or complexes" refers to salts or complexes of the below-specified compounds of Formula (I). Examples of such salts include, but are not restricted, to base addition salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein.

The term "indirectly" also encompasses prodrugs which may be converted to the active form of the drug via endogenous enzymes or metabolism. The prodrug is a derivative of the compound according to the invention and presenting NADPH oxidase inhibiting activity that has a chemically or metabolically decomposable group, and a compound that may be converted into a pharmaceutically active compound in vivo by solvolysis under physiological conditions.

The term "cardiovascular disorder or disease" comprises atherosclerosis, especially diseases or disorders associated with endothelial dysfunction including but not limited to hypertension, cardiovascular complications of Type I or Type II diabetes, intimal hyperplasia, coronary heart disease, cerebral, coronary or arterial vasospasm, endothelial dysfunction, heart failure including congestive heart failure, peripheral artery disease, restenosis, trauma caused by a stent, stroke, ischemic attack, vascular complications such as after organ transplantation, or viral or bacterial infections, myocardial infarction, hypertension, formation of atherosclerotic plaques, platelet aggregation, angina pectoris, aneurysm, aortic dissection, ischemic heart disease, cardiac hypertrophy, pulmonary embolus, thrombotic events including deep vein thrombosis, injury caused after ischemia by restoration of blood flow or oxygen delivery as in organ transplantation, open heart surgery, angioplasty, hemorrhagic shock, angioplasty of ischemic organs including heart, brain, liver, kidney, retina and bowel.

The term "respiratory disorder or disease" comprises bronchial asthma, bronchitis, allergic rhinitis, adult respiratory syndrome, cystic fibrosis, lung viral infection (influenza), pulmonary hypertension and chronic obstructive pulmonary diseases (COPD).

The term "allergic disorder" includes hay fever and asthma.

The term "traumatism" includes polytraumatism.

The term "disease or disorder affecting the metabolism" includes obesity, metabolic syndrome and Type II diabetes.

The term "skin disease" or disorder" includes psoriasis, eczema, dermatitis, wound healing and scar formation.

The term "bone disorder" includes osteoporosis, osteoporasis, osteosclerosis, periodontitis, and hyperparathyroidism.

The term "neuromuscular degenerative diseases" comprises a disease or a state characterized by a deterioration of the neuromuscular junctions, allowing for example a greater area of contact between each nerve terminal and the muscle fiber. The progression of these disorders comprises a progressive atrophy and weakness of skeletal muscles. The muscle fibers degenerate and are replaced by fatty and fibrous tissue. This term includes disorders such as Parkinson's disease, Huntington's disease, amyotrophic lateral sclerosis, epilepsy, multiple sclerosis, muscular dystrophy and the like.

The term "kidney disease or disorder" includes diabetic nephropathy, renal failure, glomerulonephritis, nephrotoxicity of aminoglycosides and platinum compounds and hyperactive bladder.

The term "reproduction disorder or disease" includes erectile dysfunction, fertility disorders, prostatic hypertrophy and benign prostatic hypertrophy.

The term "disease or disorder affecting the eye and/or the lens" includes cataract including diabetic cataract, re-opacification of the lens post cataract surgery, diabetic and other forms of retinopathy.

The term "conditions affecting the inner ear" includes presbyacusis, tinnitus, Meniere's disease and other balance problems, utriculolithiasis, vestibular migraine, and noise induced hearing loss and drug induced hearing loss (ototoxicity).

The term "inflammatory disorder or disease" means inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, heart failure, myocardial infarction, psoriasis, cystic fibrosis, stroke, acute bronchitis, chronic bronchitis, acute bronchiolitis, chronic bronchiolitis, osteoarthritis, gout, myelitis, ankylosing spondylitis, Reuter syndrome, psoriatic arthritis, spondylarthritis, juvenile arthritis or juvenile ankylosing spondylitis, reactive arthritis, infectious arthritis or arthritis after infection, gonococcal arthritis, tuberculous arthritis, viral arthritis, arthritis by bacteria, syphilitic arthritis, Lyme disease, arthritis induced by "angiitis syndrome," polyarteritis nodosa, anaphylactic angiitis, Luegenec granulomatosis, rheumatoid polymyalgia, articular cell rheumatism, calcium ciystal deposition arthritis, pseudogout, non-arthritic rheumatism, bursitis, tendosynovitis, epicondyle inflammation (tennis elbow), carpal tunnel syndrome, disorders by repetitive use (typing), mixed form of arthritis, neuropathic arthropathy, hemorrhagic arthritis, vascular peliosis, hypertrophic osteoarthropathy, multicentric reticulohistiocytosis, arthritis induced by specific diseases, blood pigmentation, sickle cell disease and other hemoglobin abnormality, hyperlipoproteinemia, dysgammaglobulinemia, hyperparathyroidism, acromegaly, familial Mediterranean fever, Bechet's disease, systemic autoimmune disease erythematosus, multiple sclerosis and Crohn's disease or diseases like relapsing polychondritis, chronic inflammatory bowel diseases (IBD) or the related diseases which require the administration to a mammal in a therapeutic effective dose of a compound expressed by Formula (I) in a sufficient dose to inhibit NADPH oxidase.

The term liver diseases or disorders include liver fibrosis, alcohol induced fibrosis, steatosis and non alcoholic steatohepatitis.

The term "arthritis" means acute rheumatic arthritis, chronic rheumatoid arthritis, chlamydial arthritis, chronic absorptive arthritis, chylous arthritis, arthritis based on bowel disease, filarial arthritis, gonorrheal arthritis, gouty arthritis, hemophilic arthritis, hypertrophic arthritis, juvenile chronic arthritis, Lyme arthritis, neonatal foal arthritis, nodular arthritis, ochronotic arthritis, psoriatic arthritis or suppurative arthritis, or the related diseases which require the administration to a mammal in a therapeutic effective dose of a compound expressed by Formula (I) in a sufficient dose to inhibit NADPH oxidase.

The term "pain" includes hyperalgesia associated with inflammatory pain.

The term "cancer" means carcinoma (e.g., fibrosarcoma, myxosarcoma, liposarcoma, chondrosarcoma, osteogenic sarcoma, chordoma, angiosarcoma, endothelium sarcoma, lymphangiosarcoma, lymphangioendothelioma, periosteoma, mesothelioma, Ewing's tumor, leiomyosarcoma, rhabdomyosarcoma, colon carcinoma, pancreatic cancer, breast cancer, ovarian cancer, prostatic carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, embryonal carcinoma, Wilms' tumor, cervical cancer, orchioncus, lung cancer, small-cell lung cancer, bladder cancer or epithelial cancer).

The term "disease or disorders of the gastrointestinal system," includes gastric mucosa disorders ischemic bowel disease management, enteritis/colitis or neutropenia.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions.

The term "subject" as used herein refers to mammals. For examples, mammals contemplated by the present invention include human, primates, domesticated animals such as cattle, sheep, pigs, horses and the like.

The term "inhibitor" used in the context of the invention is defined as a molecule that inhibits completely or partially the activity of NADPH oxidase and/or inhibit or reduce the generation of reactive oxygen species (ROS).

Compositions

The invention provides pharmaceutical or therapeutic agents as compositions and methods for treating a patient, preferably a mammalian patient, and most preferably a human patient who is suffering from a medical disorder, and in particular a disorder mediated by NADPH oxidase, such as cardiovascular diseases, respiratory disorders, disorders affecting the metabolism, skin and/or bone diseases, neuromuscular degenerative diseases, kidney diseases, reproduction disorders, inflammatory disorders, allergic disorders, traumatisms, septic, hemorrhagic and anaphylactic shock, cancers, a diseases or disorders of the gastrointestinal system and other diseases and/or disorders associated with Nicotinamide adenine dinucleotide phosphate oxidase (NADPH Oxidase).

Pharmaceutical compositions of the invention can contain one or more tetrahydroindole derivative in any form described herein. Compositions of this invention may further comprise one or more pharmaceutically acceptable additional ingredient(s), such as alum, stabilizers, antimicrobial agents, buffers, coloring agents, flavoring agents, adjuvants, and the like.

The compounds of the invention, together with a conventionally employed adjuvant, earner, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. Compositions according to the invention are preferably injectable.

Compositions of this invention may also be liquid formulations, including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives, including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in Part 5 of *Remington's Pharmaceutical Sciences*, 20th Edition, 2000, Merck Publishing Company, Easton, Pa., which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration, including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the stratum corneum, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the stratum corneum. The compounds of this invention can also be administered in sustained release forms or from sustained release drug delivery systems. A description of representative sustained release materials can also be found in the incorporated materials in *Remington's Pharmaceutical Sciences*.

Mode of Administration

Compositions of this invention may be administered in any manner, including, but not limited to, orally, parenterally, sublingually, transdermally, rectally, transmucosally, topically, via inhalation, via buccal or intranasal administration, or combinations thereof. Parenteral administration includes, but is not limited to, intravenous, intra-arterial, intra-peritoneal, subcutaneous, intramuscular, intra-thecal, and intra-articular. The compositions of this invention may also be administered in the form of an implant, which allows slow release of the compositions as well as a slow controlled i.v. infusion. In a preferred embodiment, a tetrahydroindole derivative according to the invention are administered intravenously or subcutaneously.

This invention is further illustrated by the following examples that are not intended to limit the scope of the invention in any way.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Patients

In an embodiment, patients according to the invention are patients suffering from a cardiovascular disorder or disease.

In another embodiment, patients according to the invention are patients suffering from a respiratory disorder or disease.

In another embodiment, patients according to the invention are patients suffering from a disease or disorder affecting the metabolism.

In another embodiment, patients according to the invention are patients suffering from a skin disorder.

In another embodiment, patients according to the invention are patients suffering from a bone disorder.

In another embodiment, patients according to the invention are patients suffering from a neuromuscular degenerative disorder.

In another embodiment, patients according to the invention are patients suffering from a kidney disease.

In another embodiment, patients according to the invention are patients suffering from a reproduction disorder.

In another embodiment, patients according to the invention are patients suffering from a disease or disorder affecting the eye and/or the lens and/or a condition affecting the inner ear.

In another embodiment, patients according to the invention are patients suffering from an inflammatory disorder or disease.

In another embodiment, patients according to the invention are patients suffering from a liver disease.

In another embodiment, patients according to the invention are patients suffering from pain, such as inflammatory pain.

In another embodiment, patients according to the invention are patients suffering from allergic disorders.

In another embodiment, patients according to the invention are patients suffering from traumatisms.

In another embodiment, patients according to the invention are patients suffering from septic, hemorrhagic and anaphylactic shock.

In another embodiment, patients according to the invention are patients suffering from a disease or disorders of the gastrointestinal system.

In another embodiment, patients according to the invention are patients suffering from a cancer.

Use According to the Invention

In one embodiment, the invention provides a use of a tetrahydroindole derivative according to Formula (I):

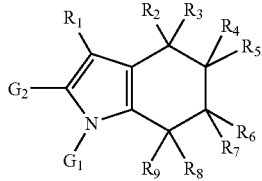

(I)

wherein $G_1$ is selected from the following groups:

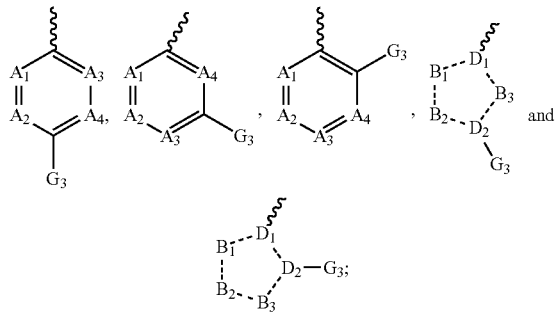

$G_2$ is selected from optionally substituted alkyl such as methyl, optionally substituted aryl, such as optionally phenyl (e.g. phenyl); optionally substituted heteroaryl such as optionally substituted pyridinyl (e.g. 2-pyridinyl-2-yl or 2-pyridinyl-3-yl), or optionally substituted benzimidazolyl (e.g. 1-methyl-1H-benzimidazol-2-yl) or optionally substituted benzo[1,4]oxazinyl (e.g. 3-oxo-3,4-dihydro-2H-1,4-benzoxazin-6-yl) or optionally substituted thiazolyl (e.g. 1,3-thiazol-2-yl); optionally substituted $C_3$-$C_8$-cycloalkyl and optionally substituted heterocycloalkyl;

$G_3$ is —C(O)$NR^{13}R^{14}$;

$A_1$, $A_2$, $A_3$ and $A_4$ are independently selected from $CR^{10}$ or N;

$B_1$, $B_2$ and $B_3$ are independently selected from $NR^{11}$, O, $CR^{11}R^{12}$ and S;

$D_1$ and $D_2$ are $CR^{11}$;

$R^1$, $R^2$, $R^3$, $R^4$, $R^5$, $R^6$, $R^7$, $R^8$ and $R^9$ are independently selected from H, halogen, optionally substituted alkyl such as optionally substituted methyl (e.g. methyl); optionally substituted alkenyl; optionally substituted alkynyl; optionally substituted aryl; optionally substituted heteroaryl; optionally substituted $C_3$-$C_8$-cycloalkyl; optionally substituted heterocycloalkyl; optionally substituted heteroalkyl; OH; $NH_2$; $NHR^{15}$; $NHCOR^{15}$; $NHSO_2R^{15}$; $SR^{15}$; $S(O)R^{15}$; $SO_2R^{15}$; $CO_2H$; and $CONHR^{15}$;

$R^{10}$ is selected from H; halogen, OH, O-alkyl, NH-Alkyl, N(Alkyl)$_2$, and optionally substituted alkyl;

$R^{11}$ and $R^{12}$ can be independently absent or when present are selected from H, halogen, optionally substituted alkyl, optionally substituted alkenyl, and optionally substituted alkynyl;

$R^{13}$ and $R^{14}$ are independently selected from H; optionally substituted alkyl, such as propyl; optionally substituted alkenyl; optionally substituted alkynyl; optionally substituted amino alkyl like optionally substituted amino propyl (e.g. 3-(dibutylamino)propyl or (3-cyclohexyl(methyl)amino) propyl or (3-butyl(methyl)amino) propyl or (3-benzyl(ethyl) amino)propyl or 3-(dipropylamino)propyl or 2-ethylpiperidin-1-yl)propyl or 3-(dimethylamino)propyl) or 3-(diethylamino)propyl) or like optionally substituted amino ethyl (e.g. (2-cyclohexyl(methyl)amino) ethyl) or 2-(diethylamino)ethyl or 2-(butyl(ethyl)amino)ethyl or 2-(dimethylamino)ethyl); optionally substituted $C_3$-$C_8$-cycloalkyl; optionally substituted heterocycloalkyl; optionally substituted aryl; optionally substituted heteroaryl; optionally substituted alkyl aryl; optionally substituted alkyl heteroaryl; optionally substituted aryl alkyl; optionally substituted heteroaryl alkyl; optionally substituted alkyl $C_3$-$C_8$-cycloalkyl; optionally substituted alkyl heterocycloalkyl; optionally substituted $C_3$-$C_8$-cycloalkyl alkyl and optionally substituted heterocycloalkyl alkyl such as optionally substituted piperidinyl alkyl like optionally substituted piperidinyl ethyl (e.g. 2-(methylpiperidin-1-yl)ethyl or piperidin-1-yl ethyl), like optionally substituted piperidinyl propyl (e.g. 2-(methylpiperidin-1-yl)propyl or 2-(ethylpiperidin-1-yl)propyl or (2,6-dimethylpiperidin-1-yl)propyl or (3,5-dimethylpiperidin-1-yl)propyl or (4-benzylpiperidin-1-yl)propyl or 4-(propylpiperidin-1-yl)propyl or 3-(piperidin-1-ylpropyl), such as optionally substituted piperazinyl alkyl like optionally substituted piperazinyl propyl (e.g. 4-(ethylpiperazin-1-yl)propyl or 4-(propylpiperazin-1-yl)propyl or (4-benzylpiperazin-1-yl) propyl), like optionally substituted piperazinyl ethyl (e.g. (4-methylpiperazin-1-yl)ethyl); such as optionally substituted pyrrolidinyl alkyl, like optionally substituted pyrrolidinyl methyl (e.g. 1-ethylpyrrolidin-2-yl-methyl), or like optionally substituted pyrrolidinyl propyl (e.g. 3-pyrrolidin-1-yl-propyl); such as optionally substituted azepan alkyl, like optionally substituted azepan propyl (e.g. 3-azepan-1-ylpropyl or 2-azepan-1-ylethyl); such as optionally substituted morpholinyl alkyl, like optionally substituted morpholinyl ethyl (e.g. 2-morpholin-4-yl ethyl) or like optionally substituted morpholinyl propyl (e.g. 3-morpholin-4-ylpropyl);

$R^{15}$ is selected from H; optionally substituted alkyl; optionally substituted alkenyl; optionally substituted alkynyl; optionally substituted $C_3$-$C_8$-cycloalkyl; optionally substituted heterocycloalkyl; optionally substituted aryl; optionally substituted heteroaryl; optionally substituted alkyl aryl; optionally substituted alkyl heteroaryl; optionally substituted aryl alkyl; optionally substituted heteroaryl alkyl; optionally substituted alkyl $C_3$-$C_8$-cycloalkyl; optionally substituted alkyl heterocycloalkyl; optionally substituted $C_3$-$C_8$-cycloalkyl alkyl and optionally substituted heterocycloalkyl alkyl;

"-----" is selected from a single and a double bond; as well as pharmaceutically acceptable salts and pharmaceutically active derivative and tautomers thereof for the preparation of a medicament for the treatment or prophylaxis of a disease or condition selected from cardiovascular diseases, respiratory disorders, disorders affecting the metabolism, skin and/or bone diseases, neuromuscular-degenerative diseases, kidney diseases, reproduction disorders, inflammatory disorders, allergic disorders, traumatisms, septic, hemorrhagic and anaphylactic shock, cancers, a diseases or disorders of the gastrointestinal system and other diseases and/or disorders associated with Nicotinamide adenine dinucleotide phosphate oxidase (NADPH Oxidase).

In another embodiment, the invention provides a use of a tetrahydroindole derivative according to Formula (I) wherein $G_1$, $G_2$, $G_3$, $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{15}$, $A_1$, $A_2$, $A_3$ and $A_4$ are as defined in the detailed description; as well as pharmaceutically acceptable salts and pharmaceutically active derivative and tautomers thereof for the preparation of a medicament for the treatment or prophylaxis of a disease or condition selected from cardiovascular diseases, respiratory disorders, disorders affecting the metabolism, skin and/or bone diseases, Parkinson's disease, Huntington's disease, amylotrophic lateral sclerosis, epilepsy, muscular dystrophy, multiple sclerosis, kidney diseases, reproduction disorders, inflammatory disorders, allergic disorders, traumatisms, septic, hemorrhagic and anaphylactic shock, cancers, a diseases or disorders of the gastrointestinal system and other diseases and/or disorders associated with Nicotinamide adenine dinucleotide phosphate oxidase (NADPH Oxidase).

In another embodiment, the invention provides a use according to the invention, wherein the disease or condition selected from cardiovascular diseases, respiratory disorders, disorders affecting the metabolism, skin and/or bone diseases, Parkinson's disease, Huntington's disease, amylotrophic lateral sclerosis, epilepsy, muscular dystrophy, multiple sclerosis, kidney diseases, reproduction disorders, allergic disorders, traumatisms, septic, hemorrhagic and anaphylactic shock, cancers, a diseases or disorders of the gastrointestinal system.

In a further embodiment, the invention provides a use of a tetrahydroindole derivative according to the invention wherein $G_1$ is:

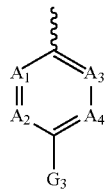

and wherein $G_2$, $G_3$, $R^1$, $R^2$, $R^3$, $R^4$, $R^5$, $R^6$, $R^7$, $R^8$, $R^9$, $R^{13}$, $R^{14}$ and $R^{15}$ are as defined in the detailed description; $A_1$, $A_2$, $A_3$ and $A_4$ are CH.

In another further embodiment, the invention provides a use of a tetrahydroindole derivative according to the invention wherein $G_1$ is:

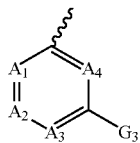

and wherein $G_2$, $G_3$, $R^1$, $R^2$, $R^3$, $R^4$, $R^5$, $R^6$, $R^7$, $R^8$, $R^9$, $R^{13}$, $R^{14}$ and $R^{15}$ are as defined in the detailed description; $A_1$, $A_2$, $A_3$ and $A_4$ are CH.

In another further embodiment, the invention provides a use of a tetrahydroindole derivative according to the invention wherein $G_1$ is selected from:

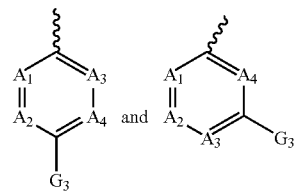

and wherein $G_2$, $G_3$, $R^1$, $R^2$, $R^3$, $R^4$, $R^5$, $R^6$, $R^7$, $R^8$, $R^9$, $R^{13}$, $R^{14}$ and $R^{15}$ are as defined in the detailed description; At least one among $A_1$, $A_2$, $A_3$ and $A_4$ is N.

In another further embodiment, the invention provides a use of a tetrahydroindole derivative according to the invention wherein $G_1$ is selected from:

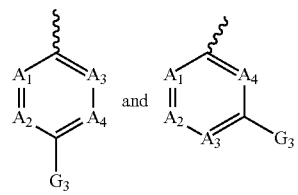

and wherein $G_2$, $G_3$, $R^1$, $R^2$, $R^3$, $R^4$, $R^5$, $R^6$, $R^7$, $R^8$, $R^9$, $R^{13}$, $R^{14}$ and $R^{15}$ are as defined in the detailed description; $A_2$ is N and $A_1$, $A_3$ and $A_4$ are CH.

In another further embodiment, the invention provides a use of a tetrahydroindole derivative according to the invention wherein $G_1$ is selected from:

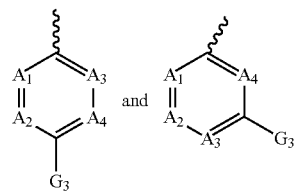

and wherein $G_2$, $G_3$> $R^1$, $R^2$, $R^3$, $R^4$, $R^5$, $R^6$, $R^7$, $R^8$, $R^9$, $R^{13}$, $R^{14}$ and $R^{15}$ are as defined in the detailed description; $A_1$ is N and $A_2$, $A_3$ and $A_4$ are CH.

In a further embodiment, the invention provides a use of a tetrahydroindole derivative according to the invention wherein $G_2$ is selected from optionally substituted aryl and optionally substituted heteroaryl.

In another further embodiment, the invention provides a use of a tetrahydroindole derivative according to the invention wherein $G_2$ is optionally substituted alkyl.

In a further embodiment, the invention provides a use of a tetrahydroindole derivative according to the invention wherein $R^2$, $R^3$, $R^5$, $R^6$, $R^7$, $R^8$ and $R^9$ are H.

In a further embodiment, the invention provides a use of a tetrahydroindole derivative according to the invention wherein $R^1$ and $R^4$ are independently selected from H and optionally substituted alkyl such as methyl.

In a further embodiment, the invention provides a use of a tetrahydroindole derivative according to the invention wherein $R^1$ and $R^4$ are independently selected from H and optionally substituted alkyl; $R^2$, $R^3$, $R^5$, $R^6$, $R^7$, $R^8$ and $R^9$ are H.

In a further embodiment, the invention provides a use of a tetrahydroindole derivative according to the invention wherein $R^{14}$ is H.

In a further embodiment, the invention provides a use of a tetrahydroindole derivative according to the invention wherein $R^{14}$ is optionally substituted such as methyl.

In a further embodiment, the invention provides a use of a tetrahydroindole derivative according to the invention wherein $R^{13}$ is optionally substituted amino alkyl.

In another further embodiment, the invention provides a use of a tetrahydroindole derivative according to the invention wherein $R^{13}$ is selected from optionally substituted $C_3$-$C_8$-cycloalkyl alkyl and optionally substituted heterocycloalkyl alkyl.

In another further embodiment, the invention provides a use of a tetrahydroindole derivative according to the invention wherein $R^{14}$ is H and $R^{13}$ is selected from optionally substituted amino alkyl and optionally substituted heterocycloalkyl alkyl.

In another further embodiment, the invention provides a use of a tetrahydroindole derivative according to the invention wherein $R^{14}$ is optionally substituted alkyl and $R^{13}$ is optionally substituted amino alkyl.

In another further embodiment, the invention provides a use of a tetrahydroindole derivative according to the invention wherein $G_1$ is:

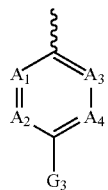

and wherein $G_2$, $G_3$ are as defined in the detailed description; $A_1$, $A_2$, $A_3$ and $A_4$ are CH; $R^1$ and $R^4$ are independently selected from H and optionally substituted alkyl; $R^2$, $R^3$, $R^5$, $R^6$, $R^7$, $R^8$ and $R^9$ are H; $R^{14}$ is H and $R^{13}$ is selected from optionally substituted amino alkyl and optionally substituted heterocycloalkyl alkyl.

In a further embodiment, the invention provides a use of a tetrahydroindole derivative according to the invention wherein $G_1$, $G_2$, $G_3$, $A_1$, $A_2$, $A_3$, $A_4$, $B_1$, $B_2$, $B_3$, $D_1$, $D_2$, $R^1$, $R^2$, $R^3$, $R^4$, $R^5$, $R^6$, $R^7$, $R^8$, $R^9$, $R^{10}$, $R^{11}$, $R^{12}$ and $R^{15}$ are as defined in the detailed description; $R^{14}$ is H and $R^{13}$ is selected from optionally substituted non fused aryl; and optionally substituted heteroaryl; as well as pharmaceutically acceptable salts and pharmaceutically active derivative and tautomers thereof.

In a further embodiment, the invention provides a use of a tetrahydroindole derivative according to the invention wherein $G_1$, $G_2$, $G_3$, $A_1$, $A_2$, $A_3$, $A_4$, $B_1$, $B_2$, $B_3$, $D_1$, $D_2$, $R^1$, $R^2$, $R^3$, $R^4$, $R^5$, $R^6$, $R^7$, $R^8$, $R^9$, $R^{10}$, $R^{11}$, $R^{12}$ and $R^{15}$ are as defined in the detailed description; $R^{13}$ and $R^{14}$ are independently selected from optionally substituted alkyl; optionally substituted alkenyl; optionally substituted alkynyl; optionally substituted amino alkyl; optionally substituted $C_3$-$C_8$-cycloalkyl; optionally substituted heterocycloalkyl; optionally substituted aryl; optionally substituted heteroaryl; optionally substituted alkyl aryl; optionally substituted alkyl heteroaryl; optionally substituted aryl alkyl; optionally substituted heteroaryl alkyl; optionally substituted alkyl $C_3$-$C_8$-cycloalkyl; optionally substituted alkyl heterocycloalkyl; optionally substituted $C_3$-$C_8$-cycloalkyl alkyl and optionally substituted heterocycloalkyl alkyl; as well as pharmaceutically acceptable salts and pharmaceutically active derivative and tautomers thereof.

In a further embodiment, the invention provides a use of a tetrahydroindole derivative according to the invention wherein $G_1$ is selected from the following groups:

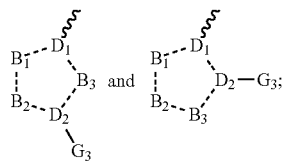

$G_2$, $G_3$, $B_1$, $B_2$, $B_3$, $D_1$, $D_2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are as defined in the detailed description; as well as pharmaceutically acceptable salts and pharmaceutically active derivative and tautomers thereof.

In another further embodiment, the invention provides a use of a tetrahydroindole derivative according to the invention wherein $G_1$ is:

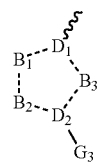

and wherein $G_2$, $G_3$, $R^1$, $R^2$, $R^3$, $R^4$, $R^5$, $R^6$, $R^7$, $R^8$, $R^9$, $R^{13}$, $R^{14}$, $R^{15}$, $B_1$, $B_2$, $B_3$, $D_1$ and $D_2$ are as defined in the detailed description.

In another further embodiment, the invention provides a use of a tetrahydroindole derivative according to the invention wherein $G_1$ is:

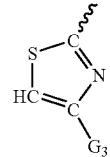

and wherein $G_2$, $G_3$, $R^1$, $R^2$, $R^3$, $R^4$, $R^5$, $R^6$, $R^7$, $R^8$, $R^9$, $R^{13}$, $R^{14}$ and $R^{15}$ are as defined in the detailed description.

In another further embodiment, the invention provides a use of a tetrahydroindole derivative according to the invention wherein $G_1$ is:

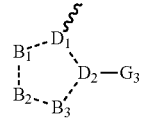

and wherein $G_2$, $G_3$, $R^1$, $R^2$, $R^3$, $R^4$, $R^5$, $R^6$, $R^7$, $R^8$, $R^9$, $R^{13}$, $R^{14}$, $R^{15}$, $B_1$, $B_2$, $B_3$, $D_1$ and $D_2$ are as defined in the detailed description.

In another embodiment, the invention provides a tetrahydroindole derivative according to Formula (I):

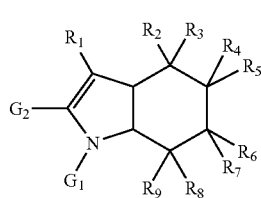

(I)

wherein $G_1, G_2, G_3, A_1, A_2, A_3, A_4, B_1, B_2, B_3, D_1, D_2, R^1, R^2, R^3, R^4, R^5, R^6, R^7, R^8, R^9, R^{10}, R^{11}, R^{12}, R^{14}$ and $R^{15}$ are as defined in the detailed description; $R^{13}$ is selected from optionally substituted alkyl; optionally substituted alkenyl; optionally substituted alkynyl; optionally substituted amino alkyl; optionally substituted $C_3$-$C_8$-cycloalkyl; optionally substituted heterocycloalkyl; optionally substituted aryl; optionally substituted heteroaryl; optionally substituted alkyl aryl; optionally substituted alkyl heteroaryl; optionally substituted aryl alkyl; optionally substituted heteroaryl alkyl; optionally substituted alkyl $C_3$-$C_8$-cycloalkyl; optionally substituted alkyl heterocycloalkyl; optionally substituted $C_3$-$C_8$-cycloalkyl alkyl and optionally substituted heterocycloalkyl alkyl; as well as pharmaceutically acceptable salts and pharmaceutically active derivative and tautomers thereof for use as a medicament.

In another embodiment, the invention provides a tetrahydroindole derivative according to Formula (I):

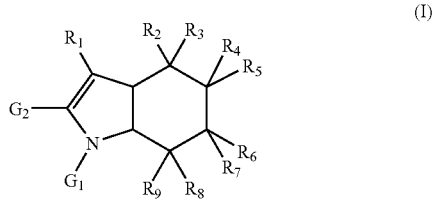

wherein $G_1, G_2, G_3, A_1, A_2, A_3, A_4, B_1, B_2, B_3, D_1, D_2, R^1, R^2, R^3, R^4, R^5, R^6, R^7, R^8, R^9, R^{10}, R^{11}, R^{12}, R^{14}$ and $R^{15}$ are as defined in the detailed description; $R^{13}$ is selected from optionally substituted alkenyl; optionally substituted alkynyl; optionally substituted amino alkyl; optionally substituted $C_3$-$C_8$-cycloalkyl; optionally substituted heterocycloalkyl; optionally substituted aryl; optionally substituted heteroaryl; optionally substituted alkyl aryl; optionally substituted alkyl heteroaryl; optionally substituted aryl alkyl; optionally substituted heteroaryl alkyl; optionally substituted alkyl $C_3$-$C_8$-cycloalkyl; optionally substituted alkyl heterocycloalkyl; optionally substituted $C_3$-$C_8$-cycloalkyl alkyl and optionally substituted heterocycloalkyl alkyl; as well as pharmaceutically acceptable salts and pharmaceutically active derivative and tautomers thereof for use as a medicament.

In another embodiment, the invention provides a tetrahydroindole derivative according to Formula (I):

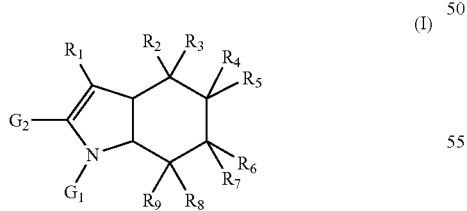

wherein $G_1, G_2, G_3, A_1, A_2, A_3, A_4, B_1, B_2, B_3, D_1, D_2, R^1, R^2, R^3, R^4, R^5, R^6, R^7, R^8, R^9, R^{10}, R^{11}, R^{12}$ and $R^{15}$ are as defined in the detailed description; $R^{14}$ is H and $R^{13}$ is selected from optionally substituted non fused aryl and optionally substituted heteroaryl; as well as pharmaceutically acceptable salts and pharmaceutically active derivative and tautomers thereof; as well as pharmaceutically acceptable salts and pharmaceutically active derivative and tautomers thereof.

In another embodiment, the invention provides a tetrahydroindole derivative according to Formula (I):

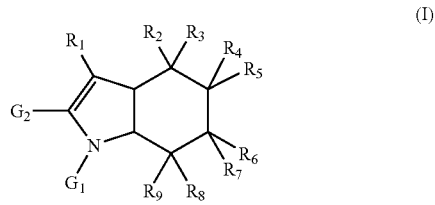

Wherein $G_1, G_2, G_3, A_1, A_2, A_3, A_4, B_1, B_2, B_3, D_1, D_2, R^1, R^2, R^3, R^4, R^5, R^6, R^7, R^8, R^9, R^{10}, R^{11}, R^{12}$ and $R^{15}$ are as defined in the detailed description; $R^{13}$ and $R^{14}$ are independently selected from optionally substituted alkyl; optionally substituted alkenyl; optionally substituted alkynyl; optionally substituted amino alkyl; optionally substituted $C_3$-$C_8$-cycloalkyl; optionally substituted heterocycloalkyl; optionally substituted aryl; optionally substituted heteroaryl; optionally substituted alkyl aryl; optionally substituted alkyl heteroaryl; optionally substituted aryl alkyl; optionally substituted heteroaryl alkyl; optionally substituted alkyl $C_3$-$C_8$-cycloalkyl; optionally substituted alkyl heterocycloalkyl; optionally substituted $C_3$-$C_8$-cycloalkyl alkyl and optionally substituted heterocycloalkyl alkyl; as well as pharmaceutically acceptable salts and pharmaceutically active derivative and tautomers thereof.

In another embodiment, the invention provides a tetrahydroindole derivative according to Formula (I) wherein $G_1, G_2, G_3, A_1, A_2, A_3, A_4, B_1, B_2, B_3, D_1; D_2, R^1, R^2, R^3, R^4, R^5, R^6, R^7, R^8, R^9, R^{10}, R^{11}, R^{12}$ and $R^{15}$ are as defined in the detailed description; and $R^{14}$ is optionally substituted alkyl and $R^{13}$ is selected from optionally substituted alkyl; optionally substituted alkenyl; optionally substituted alkynyl; optionally substituted amino alkyl; optionally substituted $C_3$-$C_8$-cycloalkyl; optionally substituted heterocycloalkyl; optionally substituted aryl; optionally substituted heteroaryl; optionally substituted alkyl aryl; optionally substituted alkyl heteroaryl; optionally substituted aryl alkyl; optionally substituted heteroaryl alkyl; optionally substituted alkyl $C_3$-$C_8$-cycloalkyl; optionally substituted alkyl heterocycloalkyl; optionally substituted $C_3$-$C_8$-cycloalkyl alkyl and optionally substituted heterocycloalkyl alkyl; as well as pharmaceutically acceptable salts and pharmaceutically active derivative and tautomers thereof.

In another embodiment, the invention provides a tetrahydroindole derivative according to Formula (I):

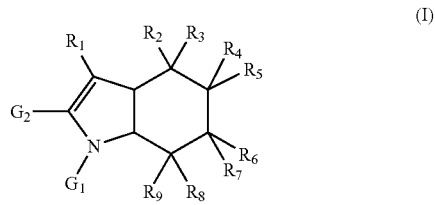

wherein $G_1$ is selected from the following groups:

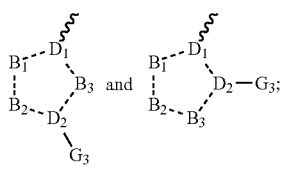

$G_2, G_3, B_1, B_2, B_3, D_1, D_2, R^1, R^2, R^3, R^4, R^5, R^6, R^7, R^8, R^9,$ $R^{11}, R^{12}, R^{13}, R^{14}$ and $R^{15}$ are as defined in the detailed description; as well as pharmaceutically acceptable salts and pharmaceutically active derivative and tautomers thereof.

In another further embodiment, the invention provides a tetrahydroindole derivative according to the invention wherein $G_1$ is:

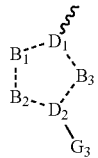

and wherein $G_2, G_3, R^1, R^2, R^3, R^4, R^5, R^6, R^7, R^8, R^9, R^{13},$ $R^{14}, R^{15}, B_1, B_2, B_3, D_1$ and $D_2$ are as defined in the detailed description.

In another further embodiment, the invention provides a tetrahydroindole derivative according to the invention wherein $G_1$ is:

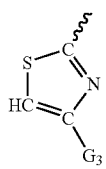

and wherein $G_2, G_3, R^1, R^2, R^3, R^4, R^5, R^6, R^7, R^8, R^9, R^{13},$ $R^{14}$ and $R^{15}$ are as defined in the detailed description.

In another further embodiment, the invention provides a tetrahydroindole derivative according to the invention wherein $G_1$ is:

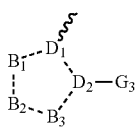

and wherein $G_2, G_3, R^1, R^2, R^3, R^4, R^5, R^6, R^7, R^8, R^9, R^{13},$ $R^{14}, R^{15}, B_1, B_2, B_3, D_1$ and $D_2$ are as defined in the detailed description.

In a further embodiment, the invention provides a tetrahydroindole derivative according to the invention wherein $G_1$ is:

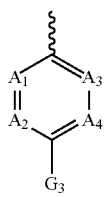

wherein $G_2, G_3, R^1, R^2, R^3, R^4, R^5, R^6, R^7, R^8, R^9, R^{11}, R^{13},$ $R^{14}$ and $R^{15}$ are as defined in the detailed description; $A_1, A_2, A_3$ and $A_4$ are CH.

In a further embodiment, the invention provides a tetrahydroindole derivative according to the invention wherein $G_1$ is:

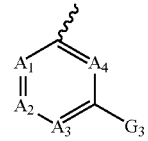

and wherein $G_2, G_3, R^1, R^2, R^3, R^4, R^5, R^6, R^7, R^8, R^9, R^{13},$ $R^{14}$ and $R^{15}$ are as defined in the detailed description; $A_1, A_2, A_3$ and $A_4$ are CH.

In another further embodiment, the invention provides a tetrahydroindole derivative according to the invention wherein $G_1$ is selected from:

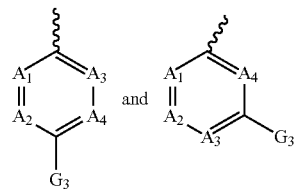

and wherein $G_2, G_3, R^1, R^2, R^3, R^4, R^5, R^6, R^7, R^8, R^9, R^{13},$ $R^{14}$ and $R^{15}$ are as defined in the detailed description; At least one among $A_1, A_2, A_3$ and $A_4$ is N.

In another further embodiment, the invention a tetrahydroindole derivative according to the invention wherein $G_1$ is selected from:

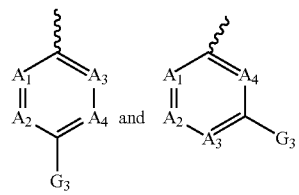

and wherein $G_2, G_3, R^1, R^2, R^3, R^4, R^5, R^6, R^7, R^8, R^9, R^{13},$ $R^{14}$ and $R^{15}$ are as defined in the detailed description; $A_2$ is N and $A_1, A_3$ and $A_4$ are CH.

In another further embodiment, the invention provides a tetrahydroindole derivative according to the invention wherein $G_1$ is selected from:

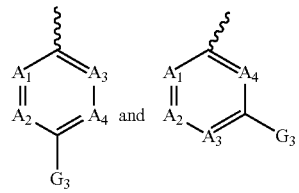

and wherein $G_2, G_3, R^1, R^2, R^3, R^4, R^5, R^6, R^7, R^8, R^9, R^{13},$ $R^{14}$ and $R^{15}$ are as defined in the detailed description; $A_1$ is N and $A_2, A_3$ and $A_4$ are CH.

In a further embodiment, the invention provides a tetrahydroindole derivative according to the invention wherein $G_2$ is selected from optionally substituted aryl and optionally substituted heteroaryl.

In a further embodiment, the invention provides a tetrahydroindole derivative according to the invention wherein $G_2$ is selected from optionally substituted alkyl.

In a further embodiment, the invention provides a tetrahydroindole derivative according to the invention wherein $R^2$, $R^3$, $R^5$, $R^6$, $R^7$, $R^8$ and $R^9$ are H.

In a further embodiment, the invention provides a tetrahydroindole derivative according to the invention wherein $R^1$ and $R^4$ are selected from H and optionally substituted alkyl.

In a further embodiment, the invention provides a tetrahydroindole derivative according to the invention wherein $R^1$ and $R^4$ are selected from H and optionally substituted alkyl; $R^2$, $R^3$, $R^5$, $R^6$, $R^7$, $R^8$ and $R^9$ are H.

In a further embodiment, the invention provides a tetrahydroindole derivative according to the invention wherein $R^{13}$ is optionally substituted amino alkyl.

In another further embodiment, the invention provides a tetrahydroindole derivative according to the invention wherein $R^{14}$ is optionally substituted alkyl.

In a further embodiment, the invention provides a tetrahydroindole derivative according to the invention wherein $R^{14}$ is H and $R^{13}$ is selected from optionally substituted amino alkyl and optionally substituted heterocycloalkyl alkyl.

In another further embodiment, the invention provides a tetrahydroindole derivative according to the invention wherein $R^{14}$ is optionally substituted alkyl and $R^{13}$ is optionally substituted amino alkyl.

In a further embodiment, the invention provides a tetrahydroindole derivative according to the invention for use as a medicament.

In another embodiment, the invention provides a pharmaceutical composition containing at least one derivative tetrahydroindole according to Formula (I) and a pharmaceutically acceptable carrier, diluent or excipient thereof.

In another embodiment, the invention provides a method for treating a patient suffering from a disease or condition selected from cardiovascular disorders, respiratory disorders, metabolism disorders, skin disorders, bone disorders, neuromuscular degenerative disorder, kidney diseases, reproduction disorders, diseases affecting the eye and/or the lens and/or conditions affecting the inner ear, inflammatory disorders, liver diseases, pain, allergic disorders, traumatisms, septic, hemorrhagic and anaphylactic shock, diseases or disorders of the gastrointestinal system and other diseases and disorders associated with Nicotinamide adenine dinucleotide phosphate oxidase (NADPH Oxidase). The method comprises administering a compound according to Formula (I) in a patient in need thereof.

In another embodiment, the invention provides a tetrahydroindole derivative according to the invention for use in the treatment of a disease or condition selected from cardiovascular disorders, respiratory disorders, metabolism disorders, skin disorders, bone disorders, neuromuscular degenerative disorder, kidney diseases, reproduction disorders, diseases affecting the eye and/or the lens and/or conditions affecting the inner ear, inflammatory disorders, liver diseases, pain, allergic disorders, traumatisms, septic, hemorrhagic and anaphylactic shock, diseases or disorders of the gastrointestinal system and other diseases and disorders associated with Nicotinamide adenine dinucleotide phosphate oxidase (NADPH Oxidase).

Compounds of the present invention include in particular those selected from the following group:
N-[2-(2-methylpiperidin-1-yl)ethyl]-4-(2-phenyl-4,5,6,7-tetrahydro-1H-indol-1-yl)benzamide;
N-[3-(2-methylpiperidin-1-yl)propyl]-4-(2-phenyl-4,5,6,7-tetrahydro-1H-indol-1-yl)benzamide;
N-[3-(4-ethylpiperazin-1-yl)propyl]-4-(2-phenyl-4,5,6,7-tetrahydro-1H-indol-1-yl) benzamide;
N-[3-(dibutylamino)propyl]-4-(2-phenyl-4,5,6,7-tetrahydro-1H-indol-1-yl)benzamide;
4-(5-methyl-2-phenyl-4,5,6,7-tetrahydro-1H-indol-1-yl)-N-[3-(4-propylpiperazin-1-yl)propyl]benzamide;
N-{3-[cyclohexyl(methyl)amino]propyl}-4-(2-phenyl-4,5,6,7-tetrahydro-1H-indol-1-yl)benzamide;
4-(2-phenyl-4,5,6,7-tetrahydro-1H-indol-1-yl)-N-[3-(4-propylpiperazin-1-yl)propyl]benzamide;
N-[3-(2-ethylpiperidin-1-yl)propyl]-4-(2-phenyl-4,5,6,7-tetrahydro-1H-indol-1-yl)benzamide;
N-(3-azepan-1-ylpropyl)-4-(2-phenyl-4,5,6,7-tetrahydro-1H-indol-1-yl)benzamide;
N-[3-(2,6-dimethylpiperidin-1-yl)propyl]-4-(2-phenyl-4,5,6,7-tetrahydro-1H-indol-1-yl)benzamide;
N-{2-[cyclohexyl(methyl)amino]ethyl}-4-(5-methyl-2-phenyl-4,5,6,7-tetrahydro-1H-indol-1-yl)benzamide;
N-{3-[butyl(methyl)amino]propyl}-4-(2-phenyl-4,5,6,7-tetrahydro-1H-indol-1-yl)benzamide;
N-[(1-ethylpyrrolidin-2-yl)methyl]-4-(2-phenyl-4,5,6,7-tetrahydro-1H-indol-1-yl)benzamide;
4-(5-methyl-2-phenyl-4,5,6,7-tetrahydro-1H-indol-1-yl)-N-[2-(4-methylpiperazin-1-yl)ethyl]benzamide;
N-{2-[cyclohexyl(methyl)amino]ethyl}-4-(2-phenyl-4,5,6,7-tetrahydro-1H-indol-1-yl)benzamide;
4-(2-phenyl-4,5,6,7-tetrahydro-1H-indol-1-yl)-N-(3-piperidin-1-ylpropyl)benzamide;
N-[3-(4-benzylpiperazin-1-yl)propyl]-4-(2,5-dimethyl-4,5,6,7-tetrahydro-4H-indol-1-yl)benzamide;
N-[3-(dipropylamino)propyl]-4-(2-phenyl-4,5,6,7-tetrahydro-1H-indol-1-yl)benzamide;
4-(2-phenyl-4,5,6,7-tetrahydro-1H-indol-1-yl)-N-(3-pyrrolidin-1-ylpropyl)benzamide;
N-[2-(diethylamino)ethyl]-4-(2-phenyl-4,5,6,7-tetrahydro-1H-indol-1-yl)benzamide;
4-(2,5-dimethyl-4,5,6,7-tetrahydro-1H-indol-1-yl)-N-[3-(2-methylpiperidin-1-yl)propyl]benzamide;
N-[3-(3,5-dimethylpiperidin-1-yl)propyl]-4-(2-phenyl-4,5,6,7-tetrahydro-1H-indol-1-yl)benzamide;
N-[3-(4-benzylpiperidin-1-yl)propyl]-4-(2,5-dimethyl-4,5,6,7-tetrahydro-1H-indol-1-yl)benzamide;
N-[3-(3,5-dimethylpiperidin-1-yl)propyl]-4-(2,5-dimethyl-4,5,6,7-tetrahydro-1H-indol-1-yl)benzamide;
N-(2-azepan-1-ylethyl)-4-(2-phenyl-4,5,6,7-tetrahydro-1H-indol-1-yl)benzamide;
N-[3-(2,6-dimethylpiperidin-1-yl)propyl]-4-(2,5-dimethyl-4,5,6,7-tetrahydro-1H-indol-1-yl)benzamide;
N-[3-(4-benzylpiperidin-1-yl)propyl]-4-(2-methyl-4,5,6,7-tetrahydro-1H-indol-1-yl)benzamide;
N-{3-[benzyl(ethyl)amino]propyl}-4-(2-methyl-4,5,6,7-tetrahydro-1H-indol-1-yl)benzamide;
N-[3-(2-ethylpiperidin-1-yl)propyl]-4-(2-methyl-4,5,6,7-tetrahydro-1H-indol-1-yl)benzamide;
4-(5-methyl-2-phenyl-4,5,6,7-tetrahydro-1H-indol-1-yl)-N-(2-morpholin-4-ylethyl)benzamide;
N-(3-morpholin-4-ylpropyl)-4-(2-phenyl-4,5,6,7-tetrahydro-1H-indol-1-yl)benzamide;
4-(2,5-dimethyl-4,5,6,7-tetrahydro-1H-indol-1-yl)-N-[(1-ethylpyrrolidin-2-yl)methyl]benzamide;

N-{3-[cyclohexyl(methyl)amino]propyl}-4-(2-methyl-4,5, 6,7-tetrahydro-1H-indol-1-yl)benzamide;
N-[3-(diethylamino)propyl]-4-(2,5-dimethyl-4,5,6,7-tetrahydro-1H-indol-1-yl)benzamide;
N-[3-(3,5-dimethylpiperidin-1-yl)propyl]-4-(2-methyl-4,5, 6,7-tetrahydro-1H-indol-1-yl)benzamide;
N-{2-[cyclohexyl(methyl)amino]ethyl}-4-(2-methyl-4,5,6, 7-tetrahydro-1H-indol-1-yl)benzamide;
N-{2-[butyl(ethyl)amino]ethyl}-4-(2-methyl-4,5,6,7-tetrahydro-1H-indol-1-yl)benzamide;
N-[2-(diethylamino)ethyl]-4-(2-methyl-4,5,6,7-tetrahydro-1H-indol-1-yl)benzamide;
4-(2-methyl-4,5,6,7-tetrahydro-1H-indol-1-yl)-N-(3-piperidin-1-ylpropyl)benzamide;
N-{2-[butyl(ethyl)amino]ethyl}-4-(2-phenyl-4,5,6,7-tetrahydro-1H-indol-1-yl)benzamide;
N-[3-(dimethylamino)propyl]-N-methyl-4-[5-methyl-2-(1-methyl-1H-benzimidazol-2-yl)-4,5,6,7-tetrahydro-1H-indol-1-yl]benzamide;
N-[2-(dimethylamino)ethyl]-4-(5-methyl-2-phenyl-4,5,6,7-tetrahydro-1H-indol-1-yl)benzamide;
N-[4-(diethylamino)-1-methylbutyl]-4-(5-methyl-2-phenyl-4,5,6,7-tetrahydro-1H-indol-1-yl)benzamide;
N-[3-(dimethylamino)propyl]-N-methyl-4-(5-methyl-2-phenyl-4,5,6,7-tetrahydro-1H-indol-1-yl)benzamide;
N-{2-[cyclohexyl(methyl)amino]ethyl}-3-(5-methyl-2-phenyl-4,5,6,7-tetrahydro-1H-indol-1-yl)benzamide;
N-{2-[cyclohexyl(methyl)amino]ethyl}-4-(5-methyl-2-pyridin-2-yl-4,5,6,7-tetrahydro-1H-indol-1-yl)benzamide;
N-{3-[cyclohexyl(methyl)amino]propyl}-4-(5-methyl-2-phenyl-4,5,6,7-tetrahydro-1H-indol-1-yl)benzamide;
N-[2-(dimethylamino)ethyl]-4-(5-methyl-2-pyridin-3-yl-4, 5,6,7-tetrahydro-1H-indol-1-yl)benzamide;
N-[3-(dimethylamino)propyl]-N-methyl-4-(5-methyl-2-pyridin-2-yl-4,5,6,7-tetrahydro-1H-indol-1-yl)benzamide;
N-[3-(dimethylamino)propyl]-N-methyl-4-(5-methyl-2-pyridin-3-yl-4,5,6,7-tetrahydro-1H-indol-1-yl)benzamide;
N-[3-(dimethylamino)propyl]-N-methyl-2-(5-methyl-2-phenyl-4,5,6,7-tetrahydro-1H-indol-1-yl)-1,3-thiazole-4-carboxamide;
N-[3-(dimethylamino)propyl]-N-methyl-5-(5-methyl-2-phenyl-4,5,6,7-tetrahydro-1H-indol-1-yl)pyridine-2-carboxamide;
N-[3-(dimethylamino)propyl]-N-methyl-5-(5-methyl-2-phenyl-4,5,6,7-tetrahydro-1H-indol-1-yl)pyridine-3-carboxamide;
N-[3-(dimethylamino)propyl]-N-methyl-4-[5-methyl-2-(3-oxo-3,4-dihydro-2H-1,4-benzoxazin-6-yl)-4,5,6,7-tetrahydro-1H-indol-1-yl]benzamide;
N-[3-(dimethylamino)propyl]-N-methyl-4-[5-methyl-2-(1, 3-thiazol-2-yl)-4,5,6,7-tetrahydro-1H-indol-1-yl]benzamide;
N-[3-(dimethylamino)propyl]-N-methyl-6-(5-methyl-2-phenyl-4,5,6,7-tetrahydro-1H-indol-1-yl)pyridine-3-carboxamide; and
N-[3-(dimethylamino)propyl]-N-methyl-3-(5-methyl-2-phenyl-4,5,6,7-tetrahydro-1H-indol-1-yl)benzamide.

The compounds of invention have been named according the IUPAC standards used in the program ACD/Name (product version 10.01).

Compounds according to the present invention also comprise its tautomers, its geometrical isomers, its optically active forms as enantiomers, diastereomers and its racemate forms, as well as pharmaceutically acceptable salts thereof.

The derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

References cited herein are hereby incorporated by reference in then entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention having been described, the following examples are presented by way of illustration, and not limitation.

Synthesis of Compounds of the Invention

The derivatives according to Formula (I) can be prepared from readily available starting L5 materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The general synthetic approach for obtaining compounds of Formula (I) is depicted in Scheme 1 below. Therein, tetrahydroindole derivatives according to the general Formula (I), whereby the substituents $G_1$, $G_2$, $G_3$, and $R^1$ to $R^{14}$ are as above defined, may be prepared in three or four chemical steps, from custom made or commercially available substituted enamine derivatives according to Formula (IV) following synthetic protocol, highlighted as outlined in the Scheme 1 below. In a more specific method, cyclohexanone derivatives according to Formula (II) wherein $R^2$ to $R^9$ are as defined above are reacted with pyrrolidine according to Formula (III), in presence of 3 Å molecular sieves, in anhydrous conditions and under refluxing conditions, to give the corresponding enamine derivatives according to Formula (IV). This reaction may be performed in solvents like benzene, toluene or other unreactive solvents. The intermediate compounds of Formula (TV) are further reacted with substituted α-halo ketone derivatives according to Formula (V) wherein $G_2$ and $R^1$ are as defined above, in either toluene or DMF as solvents, allowing to obtain 1,4-diketone derivatives of Formula (VI).

Scheme 1

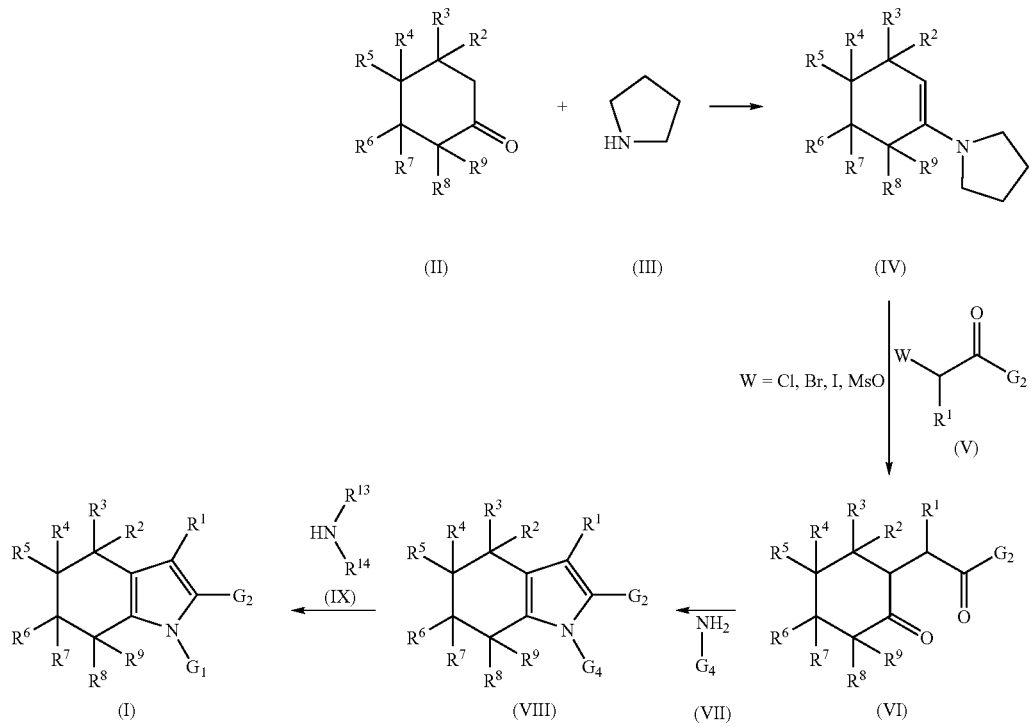

The tetrahydroindole derivatives according to Formula (VIII) are isolated after cyclisation of intermediate compounds according to Formulae (VI) and (VII), preferably in acidic conditions and under inert atmosphere, wherein $G_4$ is selected among the following groups:

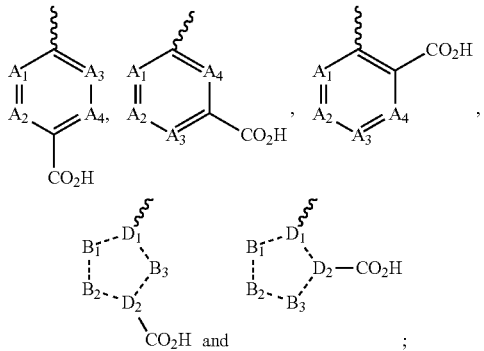

This reaction may be performed without solvent or in solvents like toluene, DMF or other unreactive solvents at room temperature over time depending of the intrinsic reactivity of compounds of Formula (V), but usually required the need of traditional thermal heating or microwave methods, using standard conditions well known to the person skilled in the art as shown in Scheme 1, above. In a subsequent step, the tetrahydroindole derivatives according to Formula (I) are isolated either after chlorination of intermediate compounds of Formula (VIII) in presence of oxalyl chloride or after treatment of compounds of Formula (VIII) with an appropriate coupling reagent such as DCC, HATU or Mukayama reagent in presence of a base like DIPEA or triethylamine, followed by condensation with a primary or secondary amine of Formula (IX) as shown in the Scheme I above. These reactions are usually performed at room temperature in solvents like dichloromethane, dichloroethane or DMF, using standard conditions well known to the person skilled in the art.

The following abbreviations refer respectively to the definitions below:

Å (Angström), min (minute), h (hour), g (gram), MHz (Megahertz), mL (milliliter), mm (millimetre), mmol (millimole), mM (millimolar), ng (nanogram), nm (nanometer), RT (room temperature), NADPH (Nicotinamide Adenine Dinucleotide Diphosphate reduced form), BSA (Bovine Serum Albumin), DCF (2,7-dichlorodihydrofluorescein), DCM (dichloromethane), DIPEA (di-isopropyl ethylamine), DMSO (Dimethyl Sulfoxide), DMF (N,N-Dimethylformamide), DAPI (4,6 Diamidino-2-phenylindole), DPI (Diphenyliodonium), cHex (Cyclohexane), EDTA (ethylenediaminetetraacetic acid), EGF (Epidermal Growth Factor), EtOAc (Ethyl acetate), FC (Flash Chromatography on silica gel), FCS (Fetal calf serum), HATU (0-(7-azabenzotriazol-1-yl)-1,1,3,3-tetramethyluronium hexafluorophosphate), HBSS (Hank's Buffered Salt Solution), HPLC (High Performance Liquid Chromatography), HUVEC (Human umbilical vein endothelial cells), $H_2DCF$-DA (2',7'-dichlorodihydrofluorescein diacetate), IFN (interferon), MEM (2-methoxyethoxymethyl), MS (Mass Spectrometry), NBT (Nitroblue tetrazolium), NMP (N-methyl piperazine), NMR (Nuclear Magnetic Resonance), NOX (NADPH oxidase), PBS (Phosphate Buffered Saline), PetEther (Petroleum ether), TEA (Triethyl amine), TFA (Trifluoroacetic acid), THF (Tetrahydrofuran), tBuOK (Potassium tert-butoxide), ROS (Reactive oxygen Species), rt (room temperature), SOD (Superoxide Dismutase), SPA (Scintillation Proximity Assay), TLC (Thin Layer Chromatography), UV (Ultraviolet).

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in "*Protecting Groups*," Georg Thieme Verlag Stuttgart, New York, 1994 and, Theodora W. Greene and Peter G. M. Wuts in "*Protective Groups in Organic Synthesis*," Wiley Interscience, 3$^{rd}$ Edition 1999.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not construed to be viewed as limiting the scope of the invention.

The HPLC, NMR and MS data provided in the examples described below are obtained as followed: HPLC: column Waters Symmetry C8 50×4.6 mm, Conditions: MeCN/H$_2$O, 5 to 100% (8 min), max plot 230-400 nm; Mass spectra: PE-SCIEX API 150 EX (APCI and ESI), LC/MS spectra: Waters ZMD (ES); $^1$H-NMR: Bruker DPX-300 MHz.

The preparative HPLC purifications are performed with HPLC Waters Prep LC 4000 System equipped with columns Prep Nova-Pak® HR C186 μm 60 Å, 40×30 mm (up to 100 mg) or with XTerra® Prep MS C8, 10 μm, 50×300 mm (up to 1 g). All the purifications are performed with a gradient of MeCN/H$_2$O 0.09% TFA; UV detection at 254 nm and 220 nm; flow 20 mL/min (up to 50 mg). TLC Analysis is performed on Merck Precoated 60 F$_{254}$ plates. Purifications by flash chromatography are performed on SiO$_2$ support, using cyclohexane/EtOAc or DCM/MeOH mixtures as eluents.

Intermediate 1: Formation of 1-cyclohex-1-en-1-ylpyrrolidine (Compound according to Formula (IV), Scheme 1)

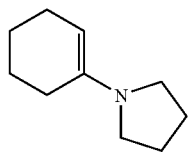

A 50 mL round-bottomed flask containing cyclohexanone (3.82 g, 39 mmol) in anhydrous toluene (20 mL) was fitted with a Dean-Stark trap containing 3 Å molecular sieves, reflux condenser and a heating mantle, pyrrolidine (6.00 mL) was added, and the solution heated to reflux for 18 h. The solvent was evaporated and the crude product 1-cyclohex-1-en-1-ylpyrrolidine was used directly for the next reaction. (6.0 g, 102% yield, 95% purity by HPLC). MS(ESI$^+$): 152.3; MS(ESI$^-$): 150.1.

Intermediate 2: Formation of 1-(4-methylcyclohex-1-en-1-yl)pyrrolidine (Compound according to Formula (IV), Scheme 1)

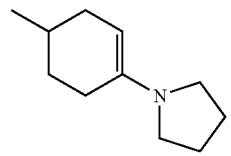

Following the general methods as outlined under Intermediate 1, starting from 4-methylcyclohexanone, and pyrrolidine, the title compound was isolated in 99% yield (96% purity by HPLC). MS(ESI$^+$): 166.4; MS(ESI$^-$): 164.6.

Intermediate 3: Formation of 2-(2-oxo-2-phenylethyl)cyclohexanone (Compound according to Formula (VI), Scheme 1)

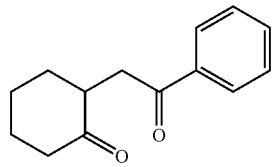

Protocol 1

To a 250-mL round-bottomed flask containing 2.4 mL of 1-cyclohex-1-en-1-ylpyrrolidine was added 100 mL anhydrous DMF, under nitrogen. The flask was fitted with an addition funnel containing 2-bromo-1-phenylethanone (4.12 g) dissolved in 35 mL anhydrous DMF, which was dropped into the enamine solution over 60 min. This solution was stirred at ambient temperature for 10 h, then 90 mL of water was added to the solution and it was stirred for another 11 hours, under nitrogen. The solution was then extracted twice with ethyl acetate and water, the organic layers combined and further washed with water (3×), dried over sodium sulphate, filtered and evaporated to give a yellow oil. The oil was purified by Flash chromatography using a gradient cyclohexane:EtOAc (9:1). The product 2-(2-oxo-2-phenylethyl)cyclohexanone was used directly for the next reaction. (4.0 g, 90% yield, 98% purity by HPLC). MS(ESI$^+$): 217.4; MS(ESI$^-$): 215.6.

Protocol 2

To a 250-mL round-bottomed flask containing 2.4 mL of 1-cyclohex-1-en-1-ylpyrrolidine was added 20 mL anhydrous NMP followed by NaI (0.645 g), under nitrogen. The flask was fitted with an addition funnel containing 2-bromo-1-phenylethanone (4.12 g) dissolved in 35 mL anhydrous NMP, which was dropped into the enamine solution over 60 min. This solution was stirred at ambient temperature for 10 h, then 90 mL of water was added to the solution and it was stirred for another 11 hours, under nitrogen. The solution was then extracted twice with ethyl acetate and water, the organic layers combined and further washed with water (3×), dried over sodium sulphate, filtered and evaporated to give a yellow oil. The oil was purified by Flash chromatography using a gradient cyclohexane:EtOAc (9:1). The product 2-(2-oxo-2-phenylethyl)cyclohexanone was used directly for the next reaction. (4.1 g, 91% yield, 98% purity by HPLC). MS(ESI$^+$): 217.4; MS(ESI$^-$): 215.6.

Intermediate 4: Formation of 4-methyl-2-(2-oxo-2-phenylethyl)cyclohexanone (Compound according to Formula (VI), Scheme 1)

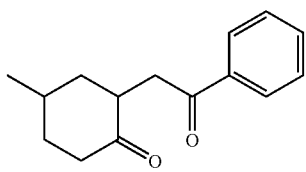

Following the general methods as outlined under Intermediate 3, starting from 1-(4-methylcyclohex-1-en-1-yl)pyrrolidine, and 2-bromo-1-phenylethanone, the title compound was isolated in 98% yield (98% purity by HPLC). MS(ESI$^+$): 231.5; MS(ESI$^-$): 229.4.

Intermediate 5: Formation of 2-(2-oxopropyl)cyclohexanone (Compound according to Formula (VI), Scheme 1)

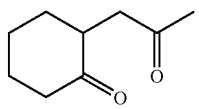

Following the general methods as outlined under Intermediate 3, starting from 1-cyclohex-1-en-1-ylpyrrolidine and 1-bromopropan-2-one, the title compound was isolated in 92% yield (95% purity by HPLC). MS(ESI$^+$): 155.3; MS(ESI$^-$): 153.2.

Intermediate 6: Formation of 4-methyl-2-(2-oxopropyl)cyclohexanone (Compound according to Formula (VI), Scheme 1)

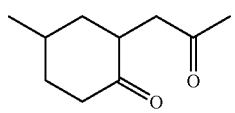

Following the general methods as outlined under Intermediate 3, starting from 1-(4-methylcyclohex-1-en-1-yl)pyrrolidine and 1-bromopropan-2-one, the title compound was isolated in 91% yield (94% purity by HPLC). MS(ESI$^+$): 169.3; MS(ESI$^-$): 167.5.

Intermediate 7: Formation of 4-(2-phenyl-4,5,6,7-tetrahydro-1H-indol-1-yl)benzoic acid (Compound according to Formula (VIII), Scheme 1)

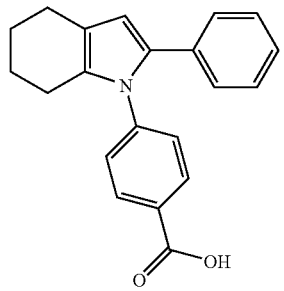

To a solution of 2-(2-oxo-2-phenylethyl)cyclohexanone (0.18 g) in glacial acetic acid (3.0 mL) in a 25-mL round-bottomed flask, under nitrogen, was fitted with a heating mantle and reflux condenser. To this solution was added 4-aminobenzoic acid (0.138 g), which was then heated at 110° C. for 3 hours. The solution was cooled to ambient temperature, 8 mL of water was added, and the suspension was stirred for 18 hours under nitrogen. The solid was filtered, washed with water, and recrystallized in acetonitrile to provide 0.18 g of 4-(2-phenyl-4,5,6,7-tetrahydro-1H-indol-1-yl) benzoic (67% yield, 98% purity by HPLC). MS(ESI$^+$): 318.4; MS(ESI$^-$): 316.5.

Intermediate 8: Formation of 4-(5-methyl-2-phenyl-4,5,6,7-tetrahydro-1H-indol-1-yl)benzoic acid (Compound according to formula (VIII), Scheme 1)

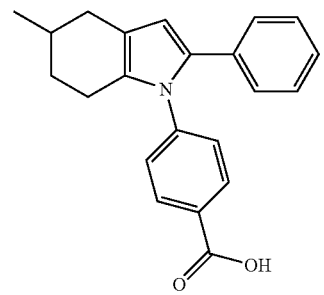

Following the general methods as outlined under Intermediate 7, starting from 4-methyl-2-(2-oxo-2-phenylethyl)cyclohexanone and 4-aminobenzoic acid, the title compound was isolated in 73% yield (95% purity by HPLC). MS(ESI$^+$): 332.5; MS(ESI$^-$): 330.4.

Intermediate 9: Formation of 4-(2-methyloctahydro-1H-indol-1-yl)benzoic acid (Compound according to formula (VIII), Scheme 1)

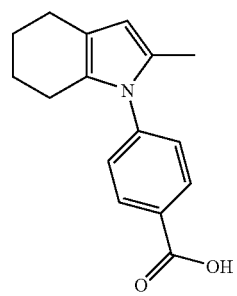

Following the general methods as outlined under Intermediate 7, starting from 2-(2-oxopropyl)cyclohexanone and 4-aminobenzoic acid, the title compound was isolated in 65% yield (98% purity by HPLC). MS(ESI⁺): 256.4; MS(ESI⁻): 254.4.

Intermediate 10: Formation of 4-(2,5-dimethyl-4,5,6,7-tetrahydro-1H-indol-1-yl)benzoic acid (Compound according to formula (VIII), Scheme 1)

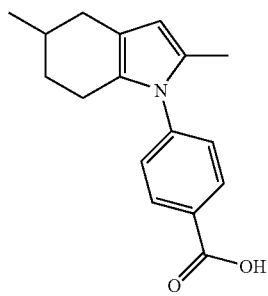

Following the general methods as outlined under Intermediate 7, starting from 4-methyl-2-(2-oxopropyl)cyclohexanone and 4-aminobenzoic acid, the title compound was isolated, in 66% yield (98% purity by HPLC). MS(ESI⁺): 270.5; MS(ESI⁻): 268.4.

Intermediate 11: Formation of 4-methyl-2-[2-oxo-2-(1,3-thiazol-2-yl)ethyl]cyclohexanone (Compound according to Formula (VI), Scheme 1)

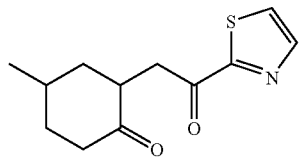

Following the general methods as outlined under Intermediate 3, starting from 1-(4-methylcyclohex-1-en-1-yl)pyrrolidine and 2-bromo-1-(1,3-thiazol-2-yl)ethanone, the title compound was isolated in 90% yield (94% purity by HPLC). MS(ESI⁺): 238.3; MS(ESI⁻): 236.4.

Intermediate 12: Formation of 4-methyl-2-(2-oxopropyl)cyclohexanone (Compound according to Formula (VI), Scheme 1)

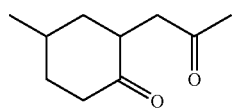

Following the general methods as outlined under Intermediate 3, starting from 1-(4-methylcyclohex-1-en-1-yl)pyrrolidine and 1-bromopropan-2-one, the title compound, was isolated in 91% yield (94% purity by HPLC). MS(ESI⁺): 169.3; MS(ESI⁻): 167.5.

Intermediate 13: Formation of 4-(2-phenyl-4,5,6,7-tetrahydro-1H-indol-1-yl)benzoic acid (Compound according to Formula (VIII), Scheme 1)

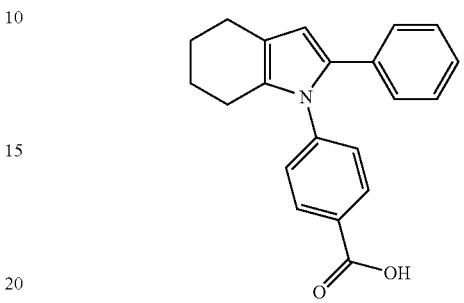

Protocol 1

To a solution of 2-(2-oxo-2-phenylethyl)cyclohexanone (0.18 g) in glacial acetic acid (3.0 mL) in a 25-mL round-bottomed flask, under nitrogen, was fitted with a heating mantle and reflux condenser. To this solution was added 4-aminobenzoic acid (0.138 g), which was then heated at 110° C. for 3 hours. The solution was cooled to ambient temperature, 8 mL of water was added, and the suspension was stirred for 18 hours under nitrogen. The solid was filtered, washed with water, and recrystallized in acetonitrile to provide 0.18 g of 4-(2-phenyl-4,5,6,7-tetrahydro-1H-indol-1-yl)benzoic (67% yield, 98% purity by HPLC).

Protocol 2

To a solution of 2-(2-oxo-2-phenylethyl)cyclohexanone (0.30 g, 1 eq) in toluene/NMP solution (3.0 mL) in a 10-mL round-bottomed flask, under nitrogen, was fitted with a heating mantle and Dean Stark. To this solution was added 4-aminobenzoic acid (0.138 g, 0.8 eq), PTSA (0.02 g, 10% mol). The reaction mixture was then heated at 130° C. and was monitored by TLC and LC/MS. Usually after 3 hours stirring, the solution was cooled to room temperature, 5 mL of water was added, and the suspension was stirred for 18 hours under nitrogen. The solid was filtered, washed with water, to provide 0.21 g 4-(2-phenyl-4,5,6,7-tetrahydro-1H-indol-1-yl)benzoic (78% yield, 98% purity by HPLC). MS(ESI⁺): 318.4; MS(ESI⁻): 316.5.

Intermediate 14: Formation of 4-(5-methyl-2-phenyl-4,5,6,7-tetrahydro-1H-indol-1-yl)benzoic acid (Compound according to Formula (VIII), Scheme 1)

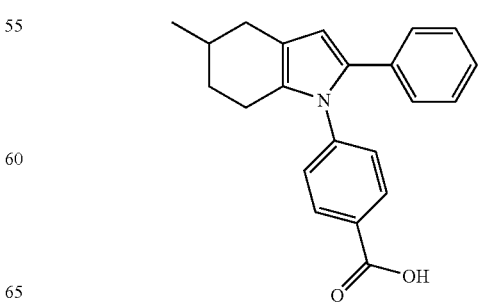

Following the general methods as outlined under Intermediate 13, starting from 4-methyl-2-(2-oxo-2-phenylethyl)cyclohexanone and 4-aminobenzoic acid, the title compound was isolated in 73% yield (95% purity by HPLC). MS(ESI⁺): 332.5; MS(ESI⁻): 330.4.

Intermediate 15: Formation of 4-(2-methyloctahydro-1H-indol-1-yl)benzoic acid (Compound according to Formula (VIII), Scheme 1)

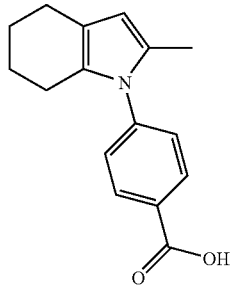

Following the general methods as outlined under Intermediate 13, starting from 2-(2-oxopropyl)cyclohexanone and 4-aminobenzoic acid, the title compound was isolated in 65% yield (98% purity by HPLC). MS(ESI⁺): 256.4; MS(ESI⁻): 254.4.

Intermediate 16: Formation of 4-(2,5-dimethyl-4,5,6,7-tetrahydro-1H-indol-1-yl) benzoic acid (Compound according to Formula (VIII), Scheme 1)

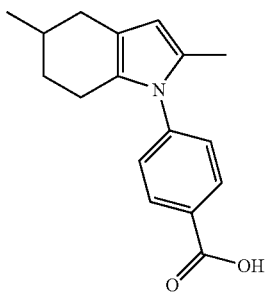

Following the general methods as outlined under Intermediate 13, starting from 4-methyl-2-(2-oxopropyl)cyclohexanone and 4-aminobenzoic acid, the title compound was isolated, in 66% yield (98% purity by HPLC). MS(ESI⁺): 270.5; MS(ESI⁻): 268.4.

Intermediate 17: Formation of 4-[5-methyl-2-(1-methyl-1H-benzimidazol-2-yl)-4,5,6,7-tetrahydro-1H-indol-1-yl]benzoic acid (Compound according to Formula (VIII), Scheme 1)

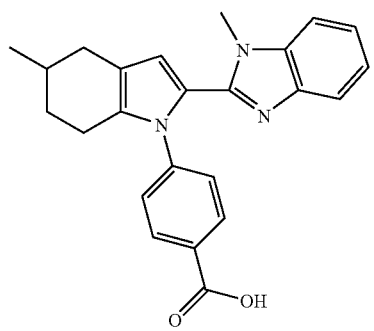

Following the general methods as outlined under Intermediate 13, starting from 4-methyl-2-[2-(1-methyl-1H-benzimidazol-2-yl)-2-oxoethyl]cyclohexanone and 4-aminobenzoic acid, the title compound was isolated in 60% yield (98% purity by HPLC). MS(ESI⁺): 386.6; MS(ESI⁻): 384.2.

Intermediate 18: Formation of 3-(5-methyl-2-phenyl-4,5,6,7-tetrahydro-1H-indol-1-yl)benzoic acid (Compound according to Formula (VIII), Scheme 1)

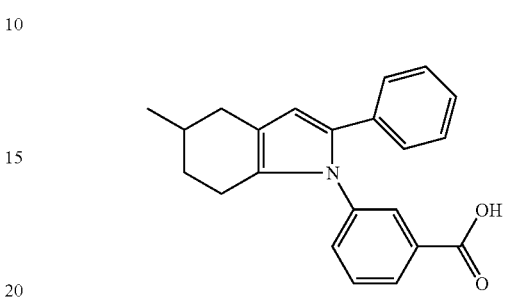

Following the general methods as outlined under Intermediate 13, starting from 4-methyl-2-(2-oxo-2-phenylethyl)cyclohexanone and 3-aminobenzoic acid, the title compound was isolated in 69% yield (98% purity by HPLC). MS(ESI⁺): 332.4; MS(ESI⁻): 330.6.

Intermediate 19: Formation of 4-(5-methyl-2-pyridin-2-yl-4,5,6,7-tetrahydro-1H-indol-1-yl)benzoic acid (Compound according to Formula (VIII), Scheme 1)

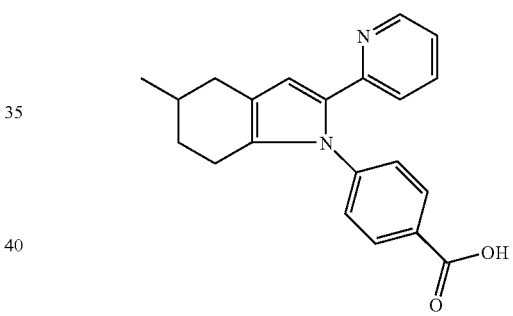

Following the general methods as outlined under Intermediate 13, starting from 4-methyl-2-(2-oxo-2-pyridin-2-ylethyl)cyclohexanone and 4-aminobenzoic acid, the title compound was isolated in 65% yield (96% purity by HPLC). MS(ESI⁺): 333.5; MS(ESI⁻): 331.6.

Intermediate 20: Formation of 4-(5-methyl-2-pyridin-3-yl-4,5,6,7-tetrahydro-1H-indol-1-yl)benzoic acid (Compound according to Formula (VIII), Scheme 1)

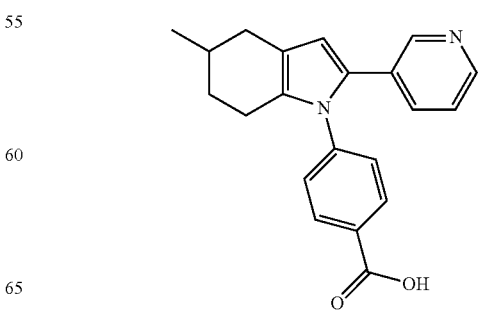

Following the general methods as outlined under Intermediate 13, starting from 4-methyl-2-(2-oxo-2-pyridin-3-ylethyl)cyclohexanone and 4-aminobenzoic acid, the title compound was isolated in 63% yield (98% purity by HPLC). MS(ESI$^+$): 333.5; MS(ESI$^-$): 331.4.

Intermediate 21: Formation of 2-(5-methyl-2-phenyl-4,5,6,7-tetrahydro-1H-indol-1-yl)-1,3-thiazole-4-carboxylic acid (Compound according to Formula (VIII), Scheme 1)

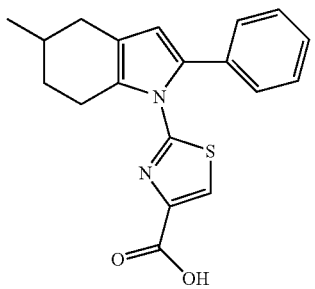

Following the general methods as outlined under Intermediate 13, starting from 4-methyl-2-(2-oxo-2-phenylethyl)cyclohexanone and methyl 2-amino-1,3-thiazole-4-carboxylate, the title compound was isolated in 49% yield (93% purity by HPLC). MS(ESI$^+$): 339.5; MS(ESI$^-$): 337.4.

Intermediate 22: Formation of 5-(5-methyl-2-phenyl-4,5,6,7-tetrahydro-1H-indol-1-yl)pyridine-2-carboxylic acid (Compound according to Formula (VIII), Scheme 1)

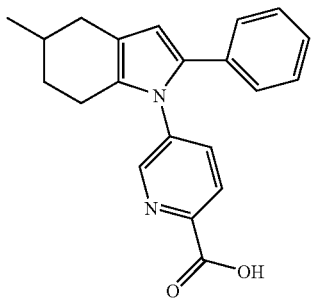

Following the general methods as outlined under Intermediate 13, starting from 4-methyl-2-(2-oxo-2-phenylethyl)cyclohexanone and 5-aminopyridine-2-carboxylic acid, the title compound was isolated in 71% yield (96% purity by HPLC). MS(ESI$^+$): 334.7; MS(ESI$^-$): 332.4.

Intermediate 23: Formation of 5-(5-methyl-2-phenyl-4,5,6,7-tetrahydro-1H-indol-1-yl)pyridine-3-carboxylic acid (Compound according to Formula (VIII), Scheme 1)

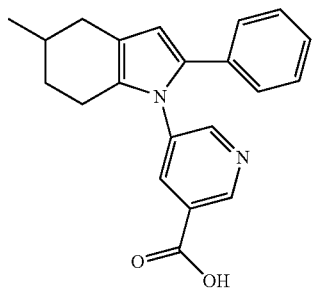

Following the general methods as outlined under Intermediate 13, starting from 4-methyl-2-(2-oxo-2-phenylethyl)cyclohexanone and 5-aminopyridine-3-carboxylic acid, the title compound was isolated in 48% yield (98% purity by HPLC). MS(ESI$^+$): 334.5; MS(ESI$^-$): 332.4.

Intermediate 24: Formation of 4-[5-methyl-2-(3-oxo-3,4-dihydro-2H-1,4-benzoxazin-6-yl)-4,5,6,7-tetrahydro-1H-indol-1-yl]benzoic acid (Compound according to Formula (VIII), Scheme 1)

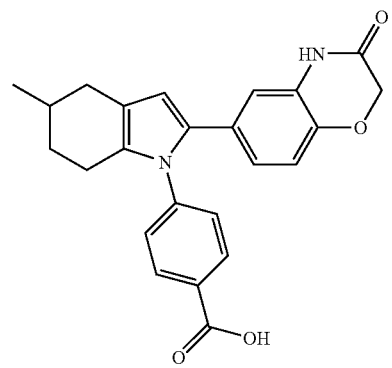

Following the general methods as outlined under Intermediate 13, starting from 6-[(5-methyl-2-oxocyclohexyl)acetyl]-2H-1,4-benzoxazin-3(4H)-one and 4-aminobenzoic acid, the title compound was isolated in 60% yield (98% purity by HPLC). MS(ESI$^+$): 403.7; MS(ESI$^-$): 401.2.

Intermediate 25: Formation of 4-[5-methyl-2-(1,3-thiazol-2-yl)-4,5,6,7-tetrahydro-1H-indol-1-yl]benzoic acid (Compound according to Formula (VIII), Scheme 1)

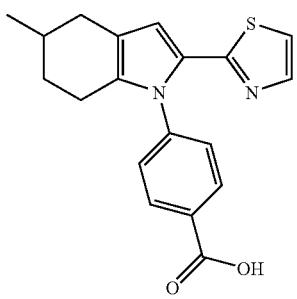

Following the general methods as outlined under Intermediate 13, starting from 4-methyl-2-[2-oxo-2-(1,3-thiazol-2-yl)ethyl]cyclohexanone and 4-aminobenzoic acid, the title compound was isolated in 45% yield (94% purity by HPLC). MS(ESI+): 339.5; MS(ESI−): 337.7.

Intermediate 26: Formation of 6-(5-methyl-2-phenyl-4,5,6,7-tetrahydro-4H-indol-1-yl)pyridine-3-carboxylic acid (Compound according to Formula (VIII), Scheme 1)

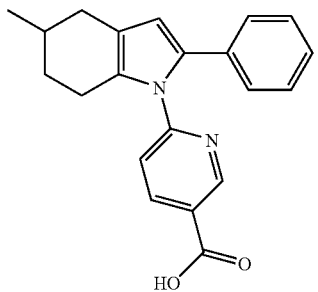

Following the general methods as outlined under Intermediate 13, starting from 4-methyl-2-(2-oxo-2-phenylethyl)cyclohexanone and 6-aminopyridine-3-carboxylic acid, the title compound was isolated in 60% yield (96% purity by HPLC). MS(ESI+): 333.7; MS(ESI−): 331.6.

Example 1

Formation of N-[2-(2-methylpiperidin-1-yl)ethyl]-4-(2-phenyl-4,5,6,7-tetrahydro-1H-indol-1-yl)benzamide (1) (Compound according to Formula (I), Scheme 1)

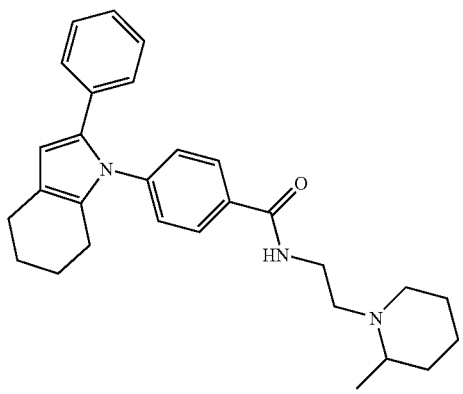

A solution of DCM containing 4-(2-phenyl-4,5,6,7-tetrahydro-1H-indol-1-yl)benzoic acid (Intermediate 7, 1 eq.) was stirred at room temperature, DMAP (1.1 equivalent) and 2-(2-methylpiperidin-1-yl)ethanamine (1 eq.) were added. The reaction mixture was then cooled down to 0° C. and EDC (1.1 eq.) was added portion-wise. After stirring for 1 hour at 0° C., the reaction mixture was allowed to warm to room temperature. The reaction was monitored by TLC and LC/MS. Usually after 12 hours stirring at RT, the reaction mixture was hydrolyzed, washed with sodium carbonate solution (10%), dried over MgSO4, and evaporated in vacuo to give a crude product. Flash chromatography on silica gel, eluting with 60% EtOAc in hexane gave, after evaporation, the expected product N-[2-(2-methylpiperidin-1-yl)ethyl]-4-(2-phenyl-4,5,6,7-tetrahydro-1H-indol-1-yl)benzamide (1) as a beige solid, in 80% yield (96% purity by HPLC). MS(ESI+): 442.7; MS(ESI−): 440.5.

Example 2

Formation of N-[3-(2-methylpiperidin-1-yl)propyl]-4-(2-phenyl-4,5,6,7-tetrahydro-1H-indol-1H-yl)benzamide (2) (Compound according to Formula (I), Scheme 1)

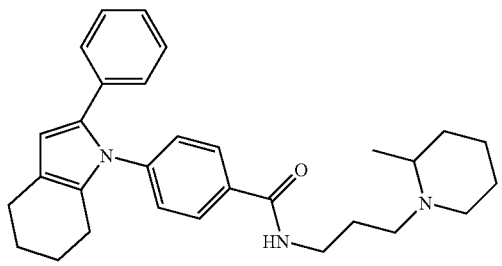

Following the general methods as outlined under Example 1, starting from 4-(2-phenyl-4,5,6,7-tetrahydro-1H-indol-1-yl)benzoic acid (Intermediate 7) and 3-(2-methylpiperidin-1-yl)propan-1-amine, the title compound (2) was isolated as a beige solid in 66% yield (82% purity by HPLC). MS(ESI+): 456.6; MS(ESI−): 454.7.

Example 3

Formation of N-[3-(4-ethylpiperazin-1-yl)propyl]-4-(2-phenyl-4,5,6,7-tetrahydro-1H-indol-1-yl)benzamide (3) (Compound according to Formula (I), Scheme 1)

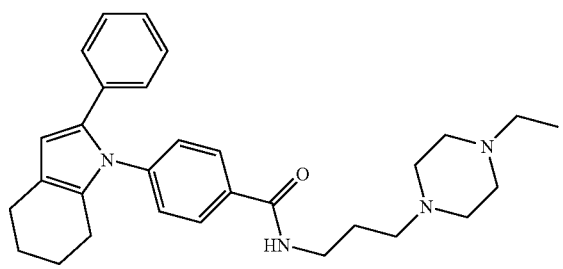

Following the general methods as outlined under Example 1, starting from 4-(2-phenyl-4,5,6,7-tetrahydro-1H-indol-1-yl)benzoic acid (Intermediate 7) and 3-(4-ethylpiperazin-1-yl)propan-1-amine, the title compound (3) was isolated as a beige solid in 69% yield (92% purity by HPLC). MS(ESI+): 471.8; MS(ESI−): 469.5.

Example 4

Formation of N-[3-(dibutylamino)propyl]-4-(2-phenyl-4,5,6,7-tetrahydro-1H-indol-1-yl)benzamide (4) (Compound according to Formula (I), Scheme 1)

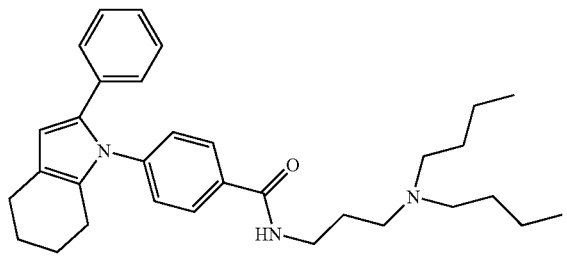

Following the general methods as outlined under Example 1, starting from 4-(2-phenyl-4,5,6,7-tetrahydro-1H-indol-1-yl)benzoic acid (Intermediate 7) and N,N-dibutylpropane-1,3-diamine, the title compound (4) was isolated as a beige solid in 72% yield (98% purity by HPLC). MS(ESI$^+$): 486.8; MS(ESI$^-$): 484.7.

Example 5

Formation of 4-(5-methyl-2-phenyl-4,5,6,7-tetrahydro-1H-indol-1-yl)-N-[3-(4-propylpiperazin-1-yl)propyl]benzamide (5) (Compound according to Formula (I), Scheme 1)

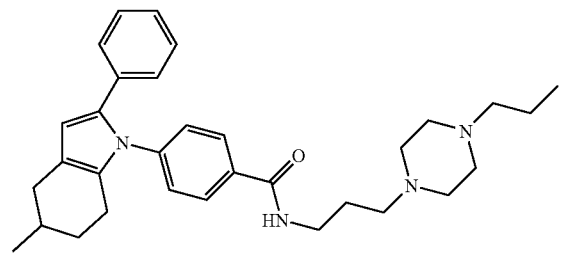

Following the general methods as outlined under Example 1, starting from 4-(5-methyl-2-phenyl-4,5,6,7-tetrahydro-1H-indol-1-yl)benzoic acid (Intermediate 8) and 3(4-propyl piperazin-1-yl)propan-1-amine, the title compound (5) was isolated as a beige solid in 70% yield (97% purity by HPLC). MS(ESI$^+$): 499.8; MS(ESI$^-$): 497.6.

Example 6

Formation of N-{3-[cyclohexyl(methyl)amino]propyl}-4-(2-phenyl-4,5,6,7-tetrahydro-1H-indol-1-yl)benzamide (6) (Compound according to Formula (I), Scheme 1)

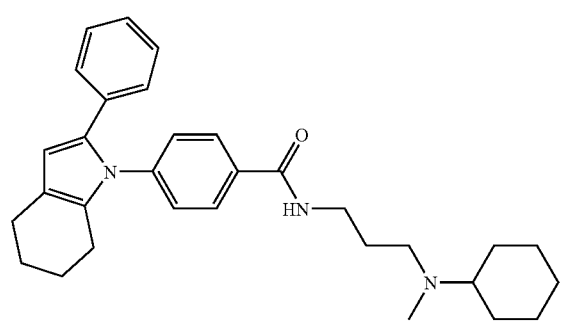

Following the general methods as outlined under Example 1, starting from 4-(2-phenyl-4,5,6,7-tetrahydro-1H-indol-1-yl)benzoic acid (Intermediate 7) and N-cyclohexyl-N-methyl propane-1,3-diamine, the title compound (6) was isolated as a beige solid in 71% yield (96% purity by HPLC). MS(ESI$^+$): 470.8; MS(ESI$^-$): 468.6.

Example 7

Formation of 4-(2-phenyl-4,5,6,7-tetrahydro-1H-indol-1-yl)-N-[3-(4-propylpiperazin-1-yl)propyl]benzamide (7) (Compound according to Formula (I), Scheme 1)

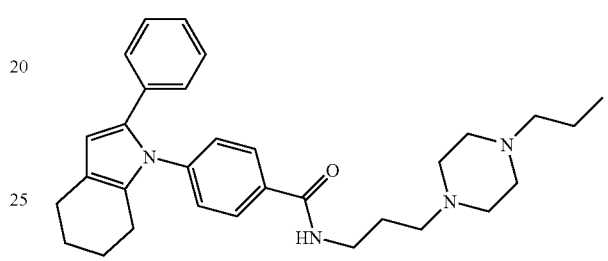

Following the general methods as outlined under Example 1, starting from 4-(2-phenyl-4,5,6,7-tetrahydro-1H-indol-1-yl)benzoic acid (Intermediate 7) and 3-(4-ethylpiperazin-1-yl)propan-1-amine, the title compound (7) was isolated as a beige solid in 66% yield (97% purity by HPLC). MS(ESI$^+$): 485.7; MS(ESI$^-$): 483.8.

Example 8

Formation of N-[3-(2-ethylpiperidin-1-yl)propyl]-4-(2-phenyl-4,5,6,7-tetrahydro-1H-indol-1-yl)benzamide (8) (Compound according to Formula (I), Scheme 1)

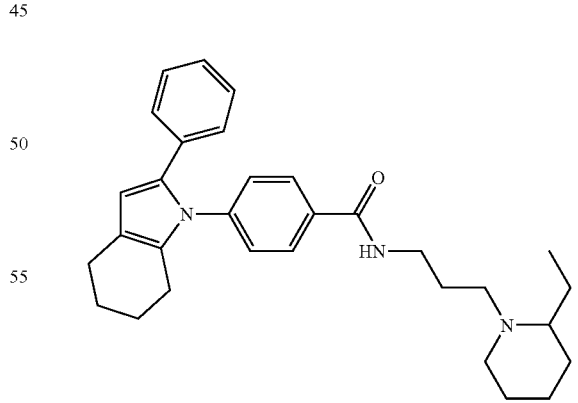

Following the general methods as outlined under Example 1, starting from 4-(2-phenyl-4,5,6,7-tetrahydro-1H-indol-1-yl)benzoic acid (Intermediate 7) and 3-(2-ethylpiperidin-1-yl)propan-1-amine, the title compound (8) was isolated as a beige solid in 62% yield (94% purity by HPLC). MS(ESI$^+$): 470.8; MS(ESI$^-$): 468.7.

Example 9

Formation of N-(3-azepan-1-ylpropyl)-4-(2-phenyl)-4,5,6,7-tetrahydro-1H-indol-1-yl)benzamide (9) (Compound according to Formula (I), Scheme 1)

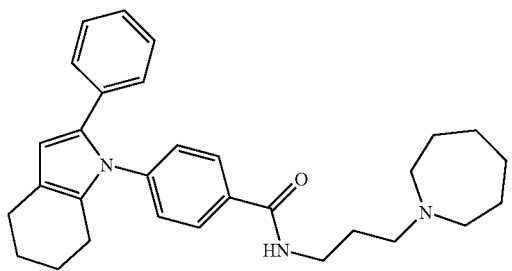

Following the general methods as outlined under Example 1, starting from 4-(2-phenyl-4,5,6,7-tetrahydro-1H-indol-1-yl)benzoic acid (Intermediate 7) and 3-azepan-1-ylpropan-1-amine, the title compound (9) was isolated as a beige solid in 68% yield (95% purity by HPLC). MS(ESI+): 466.8; MS(ESI−): 464.5.

Example 10

Formation of N-[3-(2,6-dimethylpiperidin-1-yl)propyl]-4-(2-phenyl-4,5,6,7-tetrahydro-1H-indol-1-yl)benzamide (10) (Compound according to Formula (I), Scheme 1)

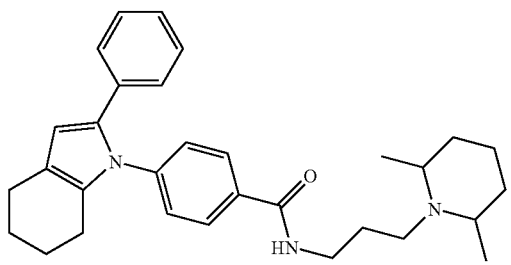

Following the general methods as outlined under Example 1, starting from 4-(2-phenyl-4,5,6,7-tetrahydro-1H-indol-1-yl)benzoic acid (Intermediate 7) and 3-(2,6-dimethyl piperidin-1-yl)propan-1-amine, the title compound (10) was isolated as a beige solid in 70% yield (96% purity by HPLC). MS(ESI+): 470.8; MS(ESI−): 468.8.

Example 11

Formation of N-{2-[cyclohexyl(methyl)amino]ethyl}-4-(5-methyl-2-phenyl-4,5,6,7-tetrahydro-1H-indol-1-yl)benzamide (11) (Compound according to Formula (I), Scheme 1)

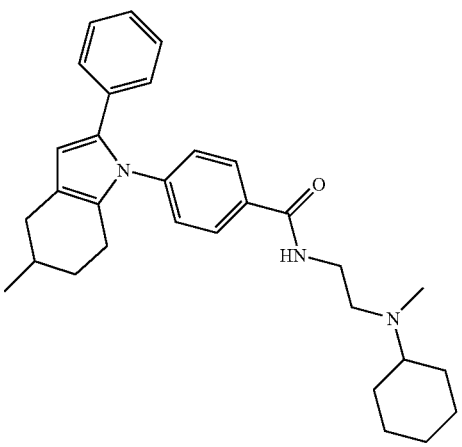

Following the general methods as outlined under Example 1, starting from 4-(5-methyl-2-phenyl-4,5,6,7-tetrahydro-1H-indol-1-yl)benzoic acid (Intermediate 8) and N-cyclohexyl-N-methylethane-1,2-diamine, the title compound (11) was isolated as a beige solid in 68% yield (96% purity by HPLC). MS(ESI+): 470.8; MS(ESI−): 468.7.

Example 12

Formation of N-{3-[butyl(methyl)amino]propyl}-4-(2-phenyl-4,5,6,7-tetrahydro-1H-indol-1-yl)benzamide (12) (Compound according to Formula (I), Scheme 1)

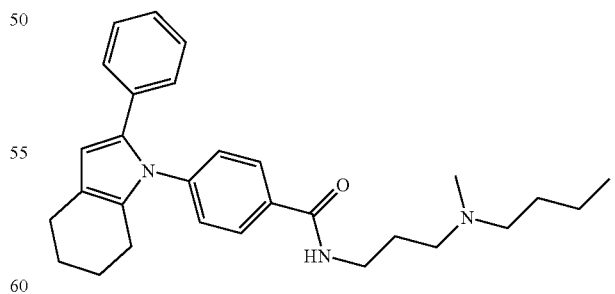

Following the general methods as outlined under Example 1, starting from 4-(2-phenyl-4,5,6,7-tetrahydro-1H-indol-1-yl)benzoic acid (Intermediate 7) and N-butyl-N-methyl propane-1,3-diamine, the title compound (12) was isolated as a beige solid in 75%> yield (95% purity by HPLC). MS(ESI⁺): 444.7; MS(ESI⁻): 442.7.

Example 13

Formation of N-[(1-ethylpyrrolidin-2-yl)methyl]-4-(2-phenyl-4,5,6,7-tetrahydro-1H-indol-1-yl)benzamide (13) (Compound according to Formula (I), Scheme 1)

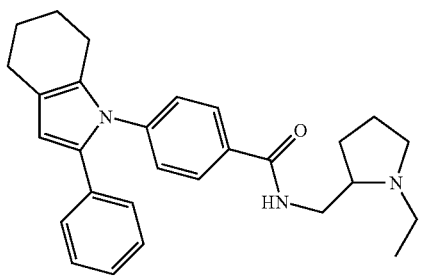

Following the general methods as outlined under Example 1, starting from 4-(2-phenyl-4,5,6,7-tetrahydro-1H-indol-1-yl)benzoic acid (Intermediate 7) and 1-(1-ethylpyrrolidin-2-yl)methanamine, the title compound (13) was isolated as a beige solid in 70%> yield (94% purity by HPLC). MS(ESI⁺): 428.7; MS(ESI⁻): 426.6.

Example 14

Formation of 4-(5-methyl-2-phenyl-4,5,6,7-tetrahydro-1H-indol-1-yl)-N-[2-(4-methylpiperazin-1-yl)ethyl]benzamide (14) (Compound according to Formula (I), Scheme 1)

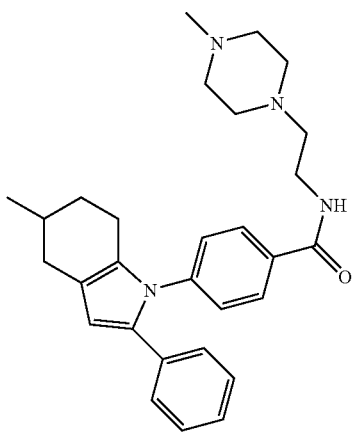

Following the general methods as outlined under Example 1, starting from 4-(5-methyl-2-phenyl-4,5,6,7-tetrahydro-1H-indol-1-yl)benzoic acid (Intermediate 8) and 2-(4-methyl piperazin-1-yl)ethanamine, the title compound (14) was isolated as a beige solid in 69% yield (93% purity by HPLC). MS(ESI⁺): 457.7; MS(ESI⁻): 455.8.

Example 15

Formation of N-{2-[cyclohexyl(methyl)amino]ethyl}-4-(2-phenyl-4,5,6,7-tetrahydro-1H-indol-1-yl)benzamide (15) (Compound according to Formula (I), Scheme 1)

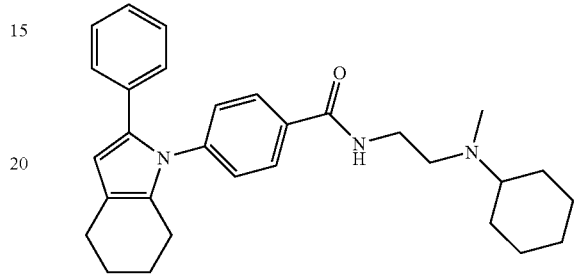

Following the general methods as outlined under Example 1, starting from 4-(2-phenyl-4,5,6,7-tetrahydro-1H-indol-1-yl)benzoic acid (Intermediate 7) and N-cyclohexyl-N-methylethane-1,2-diamine, the title compound (15) was isolated as a beige solid in 72% yield (96% purity by HPLC). MS(ESI⁺): 456.7; MS(ESI⁻): 454.6.

Example 16

Formation of 4-(2-phenyl-4,5,6,7-tetrahydro-1H-indol-1-yl)-N-(3-piperidin-1-ylpropyl)benzamide (16) (Compound according to Formula (I), Scheme 1)

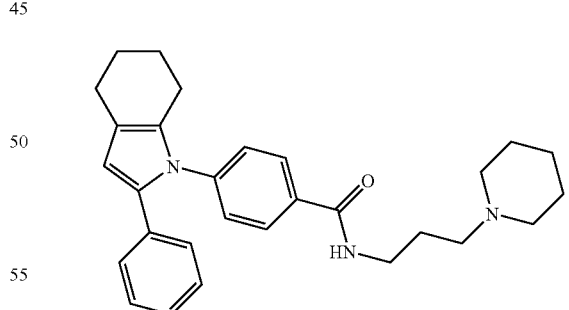

Following the general methods as outlined under Example 1, starting from 4-(2-phenyl-4,5,6,7-tetrahydro-1H-indol-1-yl)benzoic acid (Intermediate 7) and 3-piperidin-1-ylpropan-1-amine, the title compound (16) was isolated as a beige solid in 64% yield (92% purity by HPLC). MS(ESI⁺): 442.7; MS(ESI⁻): 440.6.

Example 17

Formation of N-[3-(4-benzylpiperazin-1-yl)propyl]-4-(2,5-dimethyl-4,5,6,7-tetrahydro-1H-indol-1-yl)benzamide (17) (Compound according to Formula (I), Scheme 1)

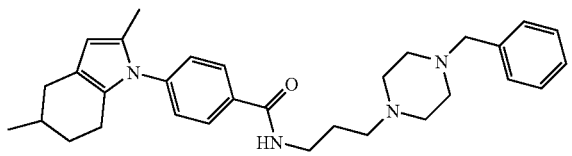

Following the general methods as outlined under Example 1, starting from 4-(2,5-dimethyl-4,5,6,7-tetrahydro-1H-indol-1-yl)benzoic acid (Intermediate 10) and 3-(4-benzylpiperazin-1-yl)propan-1-amine, the title compound (17) was isolated as a beige solid in 66% yield (97% purity by HPLC). MS(ESI$^+$): 485.8; MS(ESI$^-$): 483.6.

Example 18

Formation of N-[3-(dipropylamino)propyl]-4-(2-phenyl-4,5,6,7-tetrahydro-1H-indol-1-yl)benzamide (18) (Compound according to Formula (I), Scheme 1)

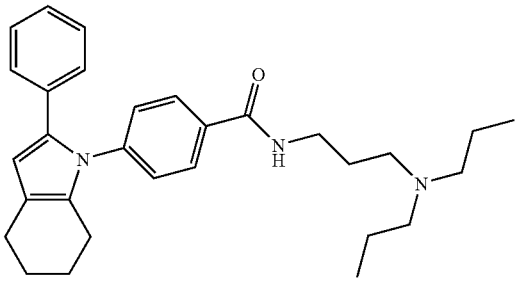

Following the general methods as outlined under Example 1, starting from 4-(2-phenyl-4,5,6,7-tetrahydro-1H-indol-1-yl)benzoic acid (Intermediate 7) and N,N-dipropylpropane-1,3-diamine, the title compound (18) was isolated as a beige solid in 68% yield (99% purity by HPLC). MS(ESI$^+$): 458.9; MS(ESI$^-$): 456.8.

Example 19

Formation of 4-(2-phenyl-4,5,6,7-tetrahydro-1H-indol-1-yl)-N-(3-pyrrolidin-1-ylpropyl)benzamide (19) (Compound according to Formula (I), Scheme 1)

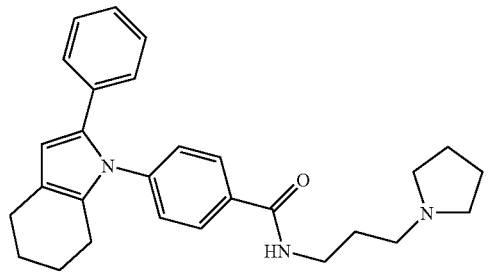

Following the general methods as outlined under Example 1, starting from 4-(2-phenyl-4,5,6,7-tetrahydro-1H-indol-1-yl)benzoic acid (Intermediate 7) and 3-pyrrolidin-1-ylpropan-1-amine, the title compound (19) was isolated as a beige solid in 69% yield (97% purity by HPLC). MS(ESI$^+$): 428.6; MS(ESI$^-$): 426.6.

Example 20

Formation of N-[2-(diethylamino)ethyl]-4-(2-phenyl-4,5,6,7-tetrahydro-1H-indol-1-yl)benzamide (20) (Compound according to Formula (I), Scheme 1)

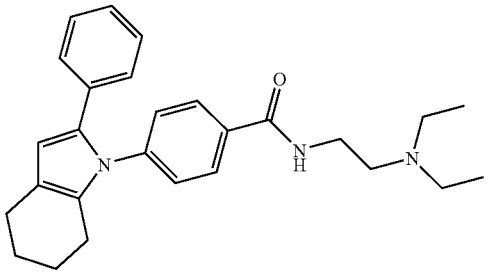

Following the general methods as outlined under Example 1, starting from 4-(2-phenyl-4,5,6,7-tetrahydro-1H-indol-1-yl)benzoic acid (Intermediate 7) and N,N-diethylethane-1,2-diamine, the title compound (20) was isolated as a beige solid in 66% yield (96% purity by HPLC). MS(ESI$^+$): 416.6; MS(ESI$^-$): 414.7.

Example 21

Formation of 4-(2,5-dimethyl-4,5,6,7-tetrahydro-1H-indol-1-yl)-N-[3-(2-methylpiperidin-1-yl)propyl]benzamide (21) (Compound according to Formula (I), Scheme 1)

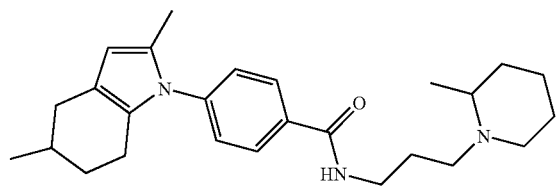

Following the general methods as outlined under Example 1, starting from 4-(2,5-dimethyl-4,5,6,7-tetrahydro-1H-indol-1-yl)benzoic acid (Intermediate 10) and 3-(2-methylpiperidin-1-yl)propan-1-amine, the title compound (21) was isolated as a beige solid in 70% yield (97% purity by HPLC). MS(ESI$^+$): 408.8; MS(ESI$^-$): 406.7.

Example 22

Formation of N-[3-(3,5-dimethylpiperidin-1-yl)propyl]-4-(2-phenyl-4,5,6,7-tetrahydro-1H-indol-1-yl)benzamide (22) (Compound according to Formula (I), Scheme 1)

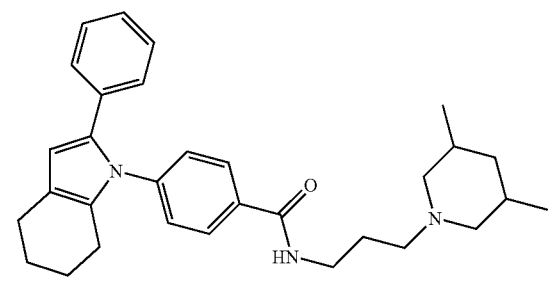

Following the general methods as outlined under Example 1, starting from 4-(2-phenyl-4,5,6,7-tetrahydro-1H-indol-1-yl)benzoic acid (Intermediate 7) and 3-(3,5-dimethyl piperidin-1-yl)propan-1-amine, the title compound (22) was isolated as a beige solid in 68% yield (97% purity by HPLC). MS(ESI⁺): 470.9; MS(ESI⁻): 468.6.

Example 23

Formation of N-[3-(4-benzylpiperidin-1-yl)propyl]-4-(2,5-dimethyl-4,5,6,7-tetrahydro-1H-indol-1-yl)benzamide (23) (Compound according to Formula (I), Scheme 1)

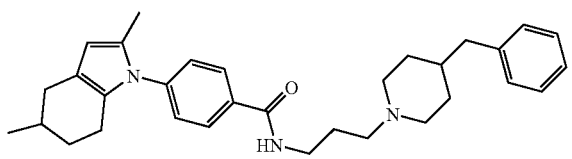

Following the general methods as outlined under Example 1, starting from 4-(2,5-dimethyl-4,5,6,7-tetrahydro-1H-indol-1-yl)benzoic acid (Intermediate 10) and 3-(4-benzylpiperidin-1-yl)propan-1-amine, the title compound (23) was isolated as a beige solid in 78% yield (99% purity by HPLC). MS(ESI⁺): 484.8; MS(ESI⁻): 482.7.

Example 24

Formation of N-[3-(3,5-dimethylpiperidin-1-yl)propyl]-4-(2,5-dimethyl-4,5,6,7-tetrahydro-1H-indol-1-yl)benzamide (24) (Compound according to Formula (I), Scheme 1)

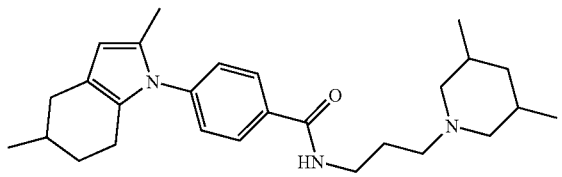

Following the general methods as outlined under Example 1, starting from 4-(2,5-dimethyl-4,5,6,7-tetrahydro-1H-indol-1-yl)benzoic acid (Intermediate 10) and 3-(3,5-dimethyl piperidin-1-yl)propan-1-amine, the title compound (24) was isolated as a beige solid in 75% yield (96% purity by HPLC). MS(ESI⁺): 422.7; MS(ESI⁻): 420.7.

Example 25

Formation of N-(2-azepan-1-ylethyl)-4-(2-phenyl-4,5,6,7-tetrahydro-1H-indol-1-yl)benzamide (25) (Compound according to Formula (I), Scheme 1)

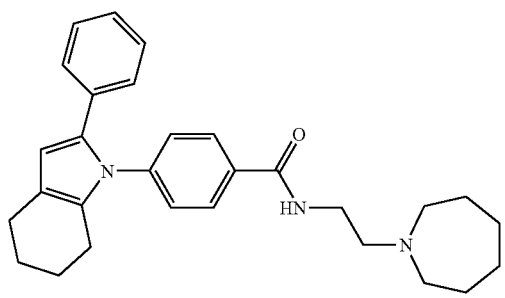

Following the general methods as outlined under Example 1, starting from 4-(2-phenyl-4,5,6,7-tetrahydro-1H-indol-1-yl)benzoic acid (Intermediate 7) and 2-azepan-1-ylethanamine, the title compound (25) was isolated as a beige solid in 79% yield (98% purity by HPLC). MS(ESI⁺): 442.8; MS(ESI⁻): 440.6.

Example 26

Formation of N-[3-(2,6-dimethylpiperidin-1-yl)propyl]-4-(2,5-dimethyl-4,5,6,7-tetrahydro-1H-indol-1-yl)benzamide (26) (Compound according to Formula (I), Scheme 1)

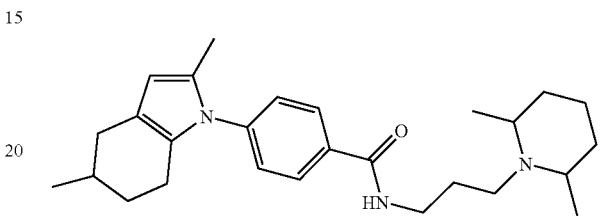

Following the general methods as outlined under Example 1, starting from 4-(2,5-dimethyl-4,5,6,7-tetrahydro-1H-indol-1-yl)benzoic acid (Intermediate 10) and 3-(2,6-dimethylpiperidin-1-yl)propan-1-amine, the title compound (26) was isolated as a beige solid in 75% yield (96% purity by HPLC). MS(ESI⁺): 422.8; MS(ESI⁻): 420.6.

Example 27

Formation of N-[3-(4-benzylpiperidin-1-yl)propyl]-4-(2-methyl-4,5,6,7-tetrahydro-1H-indol-1-yl)benzamide (27) (Compound according to Formula (I), Scheme 1)

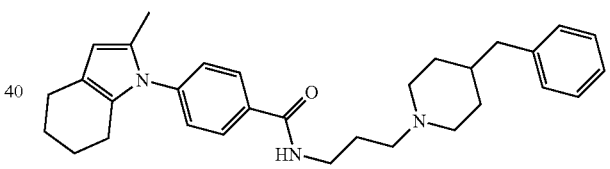

Following the general methods as outlined under Example 1, starting from 4-(2-methyloctahydro-1H-indol-1-yl)benzoic acid (Intermediate 9) and 3-(4-benzylpiperidin-1-yl)propan-1-amine, the title compound (27) was isolated as a beige solid in 78% yield (99% purity by HPLC). MS(ESI⁺): 470.8; MS(ESI⁻): 468.9.

Example 28

Formation of N-{3-[benzyl(ethyl)-amino]propyl}-4-(2-methyl-4,5,6,7-tetrahydro-1H-indol-1-yl)benzamide (28) (Compound according to Formula (I), Scheme 1)

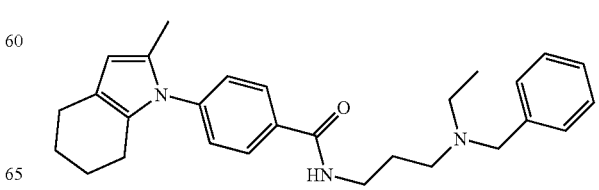

Following the general methods as outlined under Example 1, starting from 4-(2-methyloctahydro-1H-indol-1-yl)benzoic acid (Intermediate 9) and N-benzyl-N-ethylpropane-1,3-diamine, the title compound (28) was isolated as a beige solid in 72% yield (97% purity by HPLC). MS(ESI⁺): 430.6; MS(ESI⁻): 428.5.

Example 29

Formation of N-[3-(2-ethylpiperidin-1-yl)propyl]-methyl-4,5,6,7-tetrahydro-1H-indol-1-yl)benzamide (29) (Compound according to Formula (I), Scheme 1)

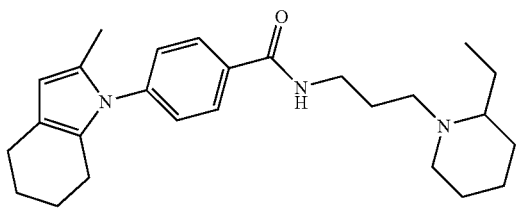

Following the general methods as outlined under Example 1, starting from 4-(2-methyloctahydro-1H-indol-1-yl)benzoic acid (Intermediate 9) and 3-(2-ethylpiperidin-1-yl)propan-1-amine, the title compound (29) was isolated as a beige solid in 70% yield (98% purity by HPLC). MS(ESI⁺): 408.6; MS(ESI⁻): 406.5.

Example 30

Formation of 4-(5-methyl-2-phenyl-4,5,6,7-tetrahydro-1H-indol-1-yl)-N-(2-morpholin-4-ylethyl)benzamide (30) (Compound according to Formula (I), Scheme 1)

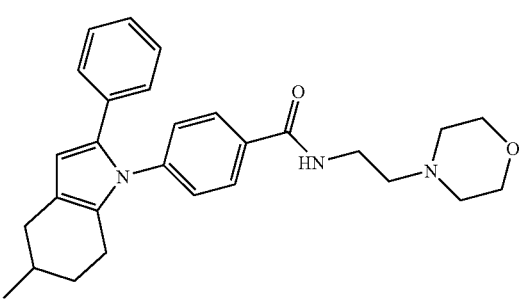

Following the general methods as outlined under Example 1, starting from 4-(5-methyl-2-phenyl-4,5,6,7-tetrahydro-1H-indol-1-yl)benzoic acid (Intermediate 8) and 2-morpholin-4-ylethanamine, the title compound (30) was isolated as a beige solid in 70% yield (96% purity by HPLC). MS(ESI⁺): 444.6; MS(ESI⁻): 442.7.

Example 31

Formation of N-(3-morpholin-4-ylpropyl)-4-(2-phenyl-4,5,6,7-tetrahydro-1H-indol-1-yl)benzamide (31) (Compound according to Formula (I), Scheme 1)

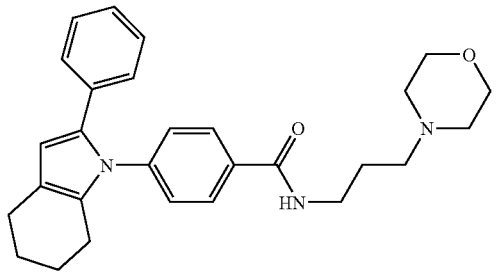

Following the general methods as outlined under Example 1, starting from 4-(2-phenyl-4,5,6,7-tetrahydro-1H-indol-1-yl)benzoic acid (Intermediate 7) and 3-morpholin-4-ylpropan-1-amine, the title compound (31) was isolated as a beige solid in 71% yield (96% purity by HPLC). MS(ESI⁺): 444.6; MS(ESI⁻): 442.6.

Example 32

Formation of 4-(2,5-dimethyl-4,5,6,7-tetrahydro-1H-indol-1-yl)-N-[(1-ethylpyrrolidin-2-yl)methyl]benzamide (32) (Compound according to Formula (I), Scheme 1)

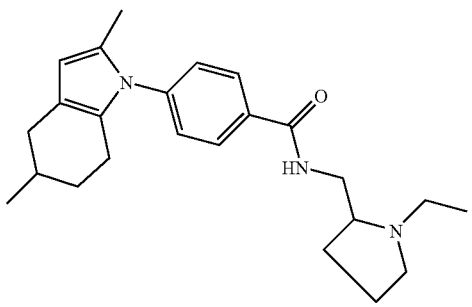

Following the general methods as outlined under Example 1, starting from 4-(2,5-dimethyl-4,5,6,7-tetrahydro-1H-indol-1-yl)benzoic acid (Intermediate 10) and 1-(1-ethylpyrrolidin-2-yl)methanamine, the title compound (32) was isolated as a beige solid in 76% yield (94% purity by HPLC). MS(ESI⁺): 380.6; MS(ESI⁻): 378.6.

Example 33

Formation of N-{3-[cyclohexyl(methyl)amino]propyl}-4-(2-methyl-4,5,6,7-tetrahydro-1H-indol-1-yl)benzamide (33) (Compound according to Formula (I), Scheme 1)

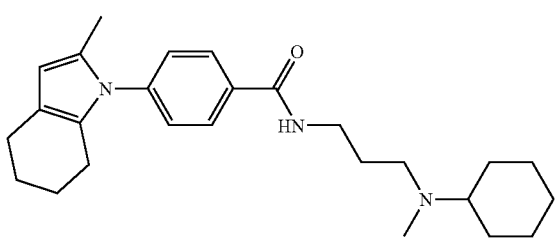

Following the general methods as outlined under Example 1, starting from 4-(2-methyloctahydro-1H-indol-1-yl)benzoic acid (Intermediate 9) and N-cyclohexyl-N-methylpropane-1,3-diamine, the title compound (33) was isolated as a beige solid in 72% yield (96% purity by HPLC). MS(ESI+): 408.7; MS(ESI−): 406.8.

Example 34

Formation of N-[3-(diethylamino)propyl]-4-(2,5-dimethyl-4,5,6,7-tetrahydro-1H-indol-1-yl)benzamide (34) (Compound according to Formula (I), Scheme 1)

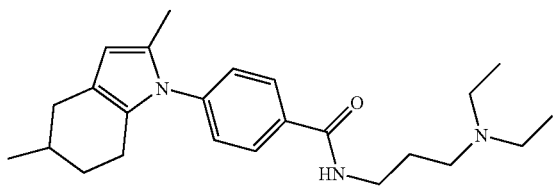

Following the general methods as outlined under Example 1, starting from 4-(2,5-dimethyl-4,5,6,7-tetrahydro-1H-indol-1-yl)benzoic acid (Intermediate 10) and N,N-ethylpropane-1,3-diamine, the title compound (34) was isolated as a beige solid in 764% yield (96% purity by HPLC). MS(ESI+): 381.6; MS(ESI−): 379.6.

Example 35

Formation of N-[3-(3,5-dimethylpiperidin-1-yl)propyl]-4-(2-methyl-4,5,6,7-tetrahydro-1H-indol-1-yl)benzamide (35) (Compound according to Formula (I), Scheme 1)

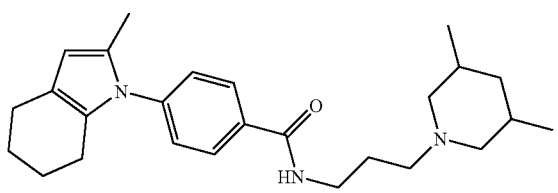

Following the general methods as outlined under Example 1, starting from 4-(2-methyloctahydro-1H-indol-1-yl)benzoic acid (Intermediate 9) and 3-(3,5-dimethylpiperidin-1-yl)propan-1-amine, the title compound (35) was isolated as a beige solid in 62% yield (98% purity by HPLC). MS(ESI+): 408.5; MS(ESI−): 406.6.

Example 36

Formation of N-{2-[cyclohexyl(methyl)amino]ethyl}-4-(2-methyl-4,5,6,7-tetrahydro-1H-indol-1-yl)benzamide (36) (Compound according to Formula (I), Scheme 1)

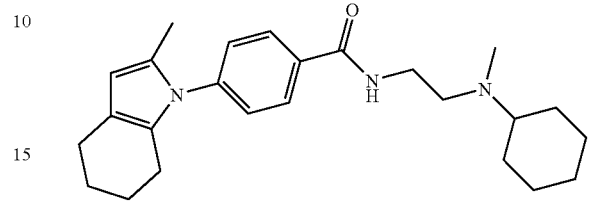

Following the general methods as outlined under Example 1, starting from 4-(2-methyloctahydro-1H-indol-1-yl)benzoic acid (Intermediate 9) and N-cyclohexyl-N-methylethane-1,2-diamine, the title compound (36) was isolated as a beige solid in 68% yield (92% purity by HPLC). MS(ESI+): 394.5; MS(ESI−): 392.6.

Example 37

Formation of N-{2-[butyl(ethyl)amino]ethyl}-4-(2-methyl-4,5,6,7-tetrahydro-1H-indol-1-yl)benzamide (37) (Compound according to Formula (I), Scheme 1)

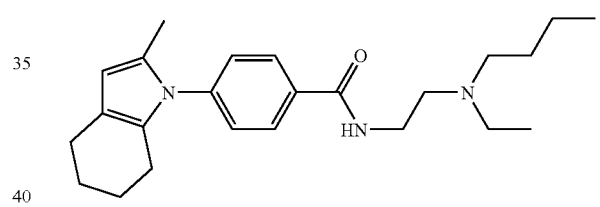

Following the general methods as outlined under Example 1, starting from 4-(2-methyloctahydro-1H-indol-1-yl)benzoic acid (Intermediate 9) and N-butyl-N-ethylethane-1,2-diamine, the title compound (37) was isolated as a beige solid in 70% yield (98% purity by HPLC). MS(ESI+): 382.6; MS(ESI−): 380.6.

Example 38

Formation of N-[2-(diethylamino)ethyl]-4-(2-methyl-4,5,6,7-tetrahydro-1H-indol-1-yl)benzamide (38) (Compound according to Formula (I), Scheme 1)

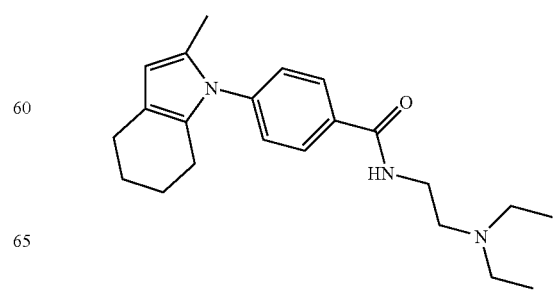

Following the general methods as outlined under Example 1, starting from 4-(2-methyloctahydro-1H-indol-1-yl)benzoic acid (Intermediate 9) and N,N-diethylethane-1,2-diamine, the title compound (38) was isolated as a beige solid in 71% yield (99% purity by HPLC). MS(ESI⁺): 354.5; MS(ESI⁻): 352.6.

Example 39

Formation of 4-(2-methyl-4,5,6,7-tetrahydro-1H-indol-1-yl)-N-(3-piperidin-1-ylpropyl)benzamide (39) (Compound according to Formula (I), Scheme 1)

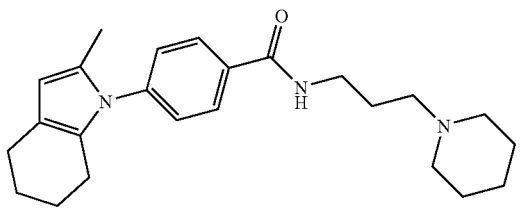

Following the general methods as outlined under Example 1, starting from 4-(2-methyloctahydro-1H-indol-1-yl)benzoic acid (Intermediate 9) and 3-piperidin-1-ylpropan-1-amine, the title compound (40) was isolated as a beige solid in 68% yield (96% purity by HPLC). MS(ESI⁺): 380.5; MS(ESI⁻): 378.6.

Example 40

Formation of N-{2-[butyl(ethyl)amino]ethyl}-4-(2-phenyl-4,5,6,7-tetrahydro-1H-indol-1-yl)benzamide (40) (Compound according to Formula (I), Scheme 1)

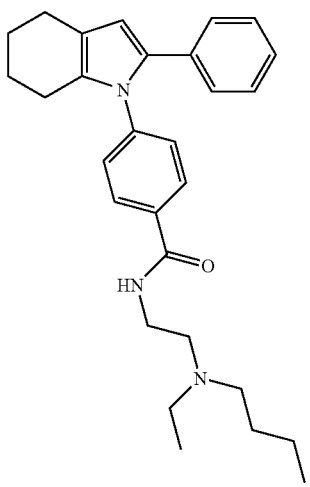

Following the general methods as outlined under Example 1, starting from 4-(2-phenyl-4,5,6,7-tetrahydro-1H-indol-1-yl)benzoic acid (Intermediate 13) and N-butyl-N-ethyl-ethane-1,2-diamine, the title compound (40) was isolated as a white solid in 52% yield (98% purity by HPLC). MS(ESI⁺): 444.6; MS(ESI⁻): 442.7.

Example 41

Formation of N-[3-(dimethylamino)propyl]-N-methyl-4-[5-methyl-2-(1-methyl-1H-benzimidazol-2-yl)-4,5,6,7-tetrahydro-1H-indol-1-yl]benzamide (41) (Compound according to Formula (I), Scheme 1)

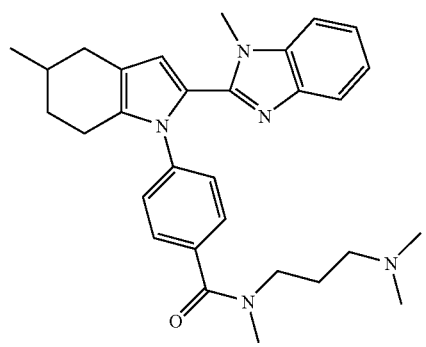

Following the general methods as outlined under Example 1, starting from 4-[5-methyl-2(1-methyl-1H-benzimidazol-2-yl)-4,5,6,7-tetrahydro-1H-indol-1-yl]benzoic acid (Intermediate 17) and N,N,N'-trimethylpropane-1,3-diamine, the title compound (41) was isolated as a beige solid in 61% yield (97% purity by HPLC). MS(ESI⁺): 484.9; MS(ESI⁻): 482.6.

Example 42

Formation of N-[2-(dimethylamino)ethyl]-4-(5-methyl-2-phenyl-4,5,6,7-tetrahydro-1H-indol-1-yl)benzamide (42) (Compound according to Formula (I), Scheme 1)

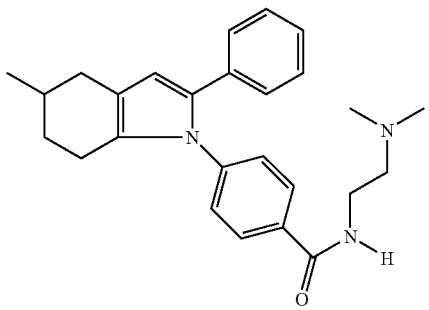

Following the general methods as outlined under Example 1, starting from 4-(5-methyl-2-phenyl-4,5,6,7-tetrahydro-1H-indol-1-yl)benzoic acid (Intermediate 14) and N,N-dimethylethane-1,2-diamine, the title compound (42) was isolated as a white solid in 70% yield (95% purity by HPLC). MS(ESI+): 402.8; MS(ESI−): 400.6.

Example 43

Formation of N-[4-(diethylamino)-1-methylbutyl]-4-(5-methyl-2-phenyl-4,5,6,7-tetrahydro-1H-indol-1-yl)benzamide (43) (Compound according to Formula (I), Scheme 1)

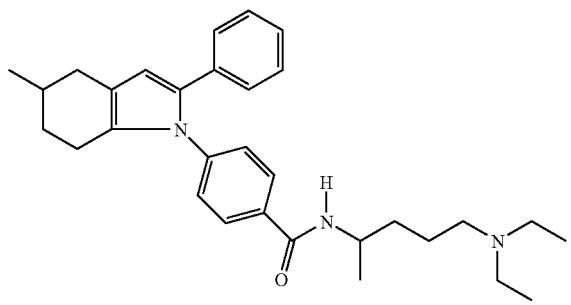

Following the general methods as outlined under Example 1, starting from 4-(5-methyl-2-phenyl-4,5,6,7-tetrahydro-1H-indol-1-yl)benzoic acid (Intermediate 14) and N,N-diethylpentane-1,4-diamine, the title compound (43) was isolated as a white solid in 50% yield (96% purity by HPLC). MS(ESI+): 472.9; MS(ESI−): 470.7.

Example 44

Formation of N-[3-(dimethylamino)propyl]-N-methyl-4-(5-methyl-2-phenyl-4,5,6,7-tetrahydro-1H-indol-1-yl)benzamide (44) (Compound according to Formula (I), Scheme 1)

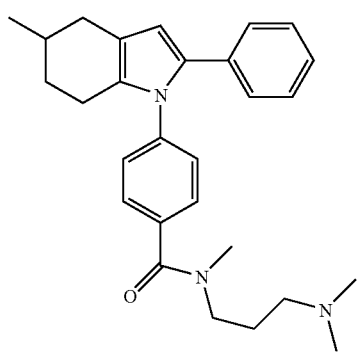

Following the general methods as outlined under Example 1, starting from 4-(5-methyl-2-phenyl-4,5,6,7-tetrahydro-1H-indol-1-yl)benzoic acid (Intermediate 14) and N,N,N'-trimethylpropane-1,3-diamine, the title compound (44) was isolated as a white solid in 63% yield (98% purity by HPLC). MS(ESI+): 430.4; MS(ESI−): 428.8.

Example 45

Formation of N-{2-[cyclohexyl(methyl)amino]ethyl}-3-(5-methyl-2-phenyl-4,5,6,7-tetrahydro-1H-indol-1-yl)benzamide (45) (Compound according to Formula (I), Scheme 1)

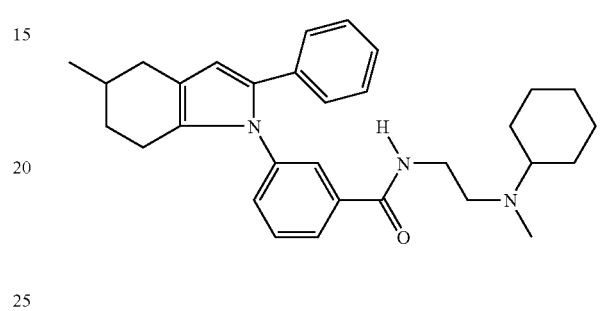

Following the general methods as outlined under Example 1, starting from 3-(5-methyl-2-phenyl-4,5,6,7-tetrahydro-1H-indol-1-yl)benzoic acid (Intermediate 18) and N-cyclohexyl-N-methylethane-1,2-diamine, the title compound (45) was isolated as a white solid in 50% yield (98% purity by HPLC). MS(ESI+): 470.8; MS(ESI−): 468.6.

Example 46

Formation of N-{2-[cyclohexyl(methyl)amino]ethyl}-4-(5-methyl-2-pyridin-2-yl-4,5,6,7-tetrahydro-1H-indol-1-yl)benzamide (46) (Compound according to Formula (I), Scheme 1)

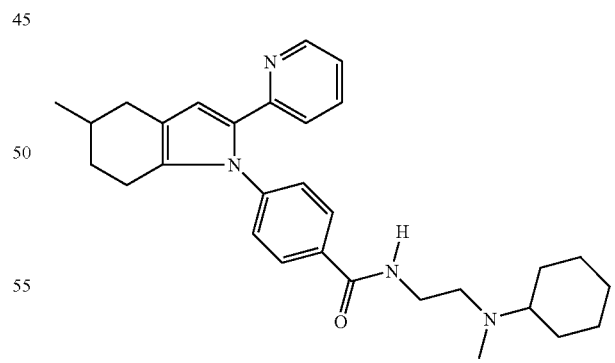

Following the general methods as outlined under Example 1, starting from 4-(5-methyl-2-pyridin-2-yl-4,5,6,7-tetrahydro-1H-indol-1-yl)benzoic acid (Intermediate 19) and N-cyclohexyl-N-methylethane-1,2-diamine, the title compound

(46) was isolated as a white solid in 70% yield (96% purity by HPLC). MS(ESI⁺): 471.7; MS(ESI⁻): 469.4.

Example 47

Formation of N-{3-[cyclohexyl(methyl)amino]propyl}-4-(5-methyl-2-o phenyl-4,5,6,7-tetrahydro-1H-indol-1-yl)-benzamide (47) (Compound according to Formula (I), Scheme 1)

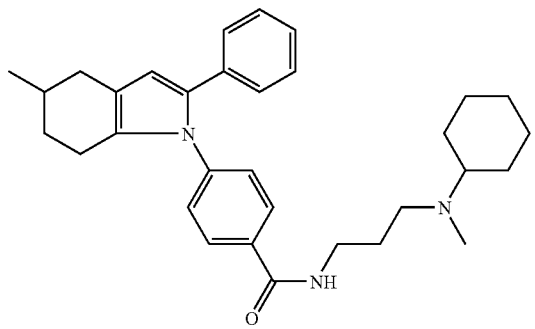

Following the general methods as outlined under Example 1, starting from 4-(5-methyl-2-phenyl-4,5,6,7-tetrahydro-1H-indol-1-yl)benzoic acid (Intermediate 14) and N-cyclohexyl-N-methylpropane-1,3-diamine, the title compound (47) was isolated as a white solid in 48% yield (98% purity by HPLC). MS(ESI⁺): 484.8; MS(ESI⁻): 482.4.

Example 48

Formation of N-[2-(dimethylamino)ethyl]-4-(5-methyl-2-pyridin-3-yl-4,5,6,7-tetrahydro-1H-indol-1-yl)benzamide (48) (Compound according to Formula (I), Scheme 1)

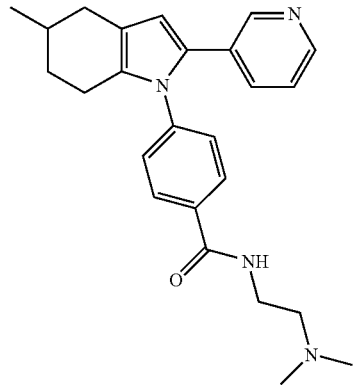

Following the general methods as outlined under Example 1, starting from 4-(5-methyl-2-pyridin-3-yl-4,5,6,7-tetrahydro-1H-indol-1-yl)benzoic acid (Intermediate 20) and N,N-dimethylethane-1,2-diamine, the title compound (48) was isolated as a beige solid in 53% yield (96% purity by HPLC). MS(ESI⁺): 403.8; MS(ESI⁻): 401.6.

Example 49

Formation of N-[3-(dimethylamino)propyl]-N-methyl-4-(5-methyl-2-pyridin-2-yl-4,5,6,7-tetrahydro-1H-indol-1-yl)benzamide (49) (Compound according to Formula (I), Scheme 1)

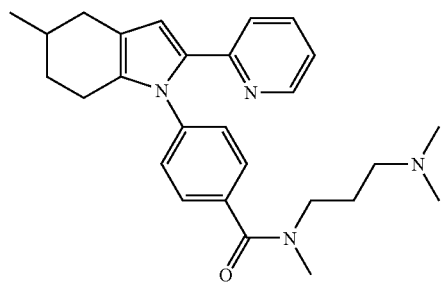

Following the general methods as outlined under Example 1, starting from 4-(5-methyl-2-pyridin-2-yl-4,5,6,7-tetrahydro-1H-indol-1-yl)benzoic acid (Intermediate 19) and N,N,N'-trimethylpropane-1,3-diamine, the title compound (49) was isolated as a white solid in 57% yield (98% purity by HPLC). MS(ESI⁺): 431.7; MS(ESI⁻): 429.8.

Example 50

Formation of N-[3-(dimethylamino)propyl]-N-methyl-4-(5-methyl-2-pyridin-3-yl-4,5,6,7-tetrahydro-1H-indol-1-yl)benzamide (50) (Compound according to Formula (I), Scheme 1)

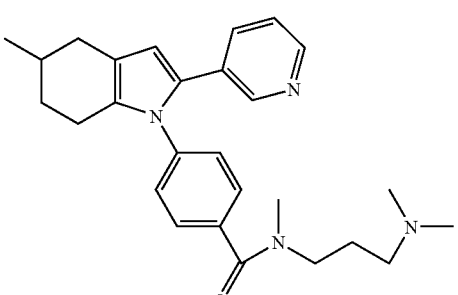

Following the general methods as outlined under Example 1, starting from 4-(5-methyl-2-pyridin-3-yl-4,5,6,7-tetrahydro-1H-indol-1-yl)benzoic acid (Intermediate 20) and N,N,N'-trimethylpropane-1,3-diamine, the title compound (50)

was isolated as a beige solid in 50% yield (97% purity by HPLC). MS(ESI+): 431.7; MS(ESI−): 429.6.

Example 51

Formation of N-[3-(dimethylamino)propyl]-N-methyl-2-(5-methyl-2-phenyl-4,5,6,7-tetrahydro-1H-indol-1-yl)-1,3-thiazole-4-carboxamide (51) (Compound according to Formula (I), Scheme 1)

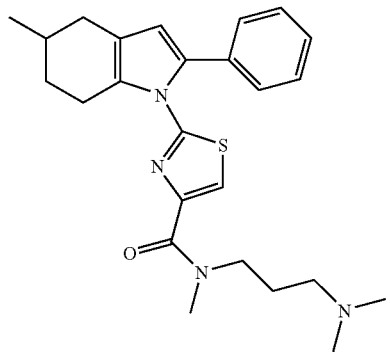

Following the general methods as outlined under Example 1, starting from 2-(5-methyl-2-phenyl-4,5,6,7-tetrahydro-1H-indol-1-yl)-1,3-thiazole-4-carboxylic acid (Intermediate 21) and N,N,N'-trimethylpropane-1,3-diamine, the title compound (51) was isolated as a yellowish solid in 46% yield (98% purity by HPLC). MS(ESI+): 437.9; MS(ESI−): 435.6

Example 52

Formation of N-[3-(dimethylamino)propyl]-N-methyl-5-(5-methyl-2-phenyl-4,5,6,7-tetrahydro-1H-indol-1-yl)pyridine-2-carboxamide (52) (Compound according to Formula (I), Scheme 1)

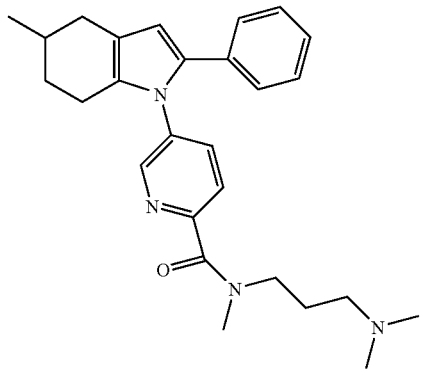

Following the general methods as outlined under Example 1, starting from 5-(5-methyl-2-phenyl-4,5,6,7-tetrahydro-1H-indol-1-yl)pyridine-2-carboxylic acid (Intermediate 22) and N,N,N'-trimethylpropane-1,3-diamine, the title compound (52) was isolated as a white solid in 54% yield (96% purity by HPLC). MS(ESI+): 431.4; MS(ESI−): 429.7.

Example 53

Formation of N-[3-(dimethylamino)propyl]-N-methyl-5-(5-methyl-2-phenyl-4,5,6,7-tetrahydro-1H-indol-1-yl)pyridine-3-carboxamide (53) (Compound according to Formula (I), Scheme 1)

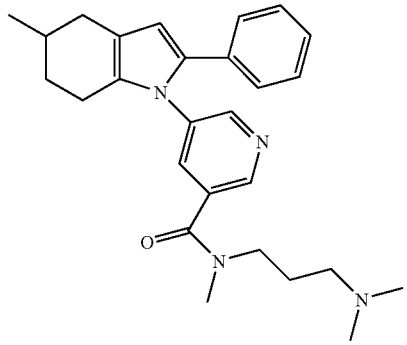

Following the general methods as outlined under Example 1, starting from 5-(5-methyl-2-phenyl-4,5,6,7-tetrahydro-1H-indol-1-yl)pyridine-3-carboxylic acid (Intermediate 23) and N,N,N'-trimethylpropane-1,3-diamine, the title compound (53) was isolated as a yellowish solid in 52% yield (98% purity by HPLC). MS(ESI+): 431.8; MS(ESI−): 429.7.

Example 54

Formation of N-[3-(dimethylamino)propyl]-N-methyl-4-[5-methyl-2-(3-oxo-3,4-dihydro-2H-1,4-benzoxazin-6-yl)-4,5,6,7-tetrahydro-1H-indol-1-yl]benzamide (54) (Compound according to Formula (I), Scheme 1)

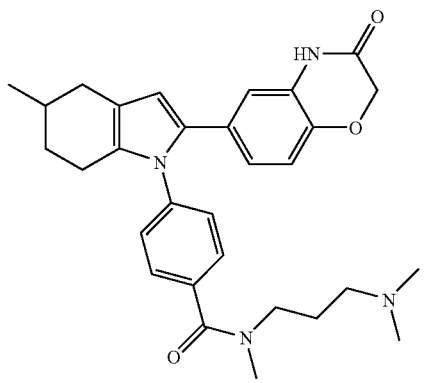

Following the general methods as outlined under Example 1, starting from 4-[5-methyl-2-(3-oxo-3,4-dihydro-2H-1,4-benzoxazin-6-yl)-4,5,6,7-tetrahydro-1H-indol-1-yl]benzoic acid (Intermediate 24) and N,N,N'-trimethylpropane-1,3-diamine, the title compound (54) was isolated as a beige solid in 58% yield (98% purity by HPLC). MS(ESI$^+$): 501.8; MS(ESI$^-$): 499.7.

Example 55

Formation of N-[3-(dimethylamino)propyl]-N-methyl-4-[5-methyl-2-(1,3-thiazol-2-yl)-4,5,6,7-tetrahydro-1H-indol-1-yl]benzamide (55) (Compound according to Formula (I), Scheme 1)

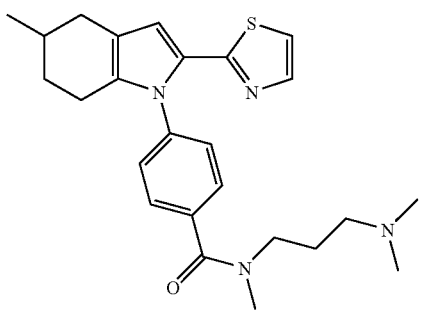

Following the general methods as outlined under Example 1, starting from 4-[5-methyl-2-(1,3-thiazol-2-yl)-4,5,6,7-tetrahydro-1H-indol-1-yl]benzoic acid (Intermediate 25) and N,N,N'-trimethylpropane-1,3-diamine, the title compound (55) was isolated as a yellowish solid in 40% yield (97% purity by HPLC). MS(ESI$^+$): 437.8; MS(ESI$^-$): 435.7.

Example 56

Formation of N-[3-(dimethylamino)propyl]-N-methyl-6-(5-methyl-2-phenyl-4,5,6,7-tetrahydro-1H-indol-1-yl)pyridine-3-carboxamide (56) (Compound according to Formula (I), Scheme 1)

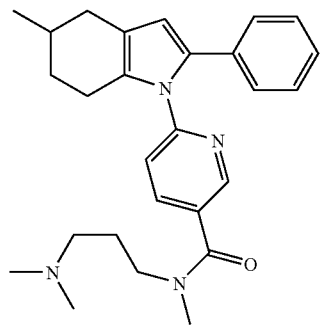

Following the general methods as outlined under Example 1, starting from 6-(5-methyl-2-phenyl-4,5,6,7-tetrahydro-1H-indol-1-yl)pyridine-3-carboxylic acid (Intermediate 26) and N,N,N'-trimethylpropane-1,3-diamine, the title compound (56) was isolated as a beige solid in 57% yield (99% purity by HPLC). MS(ESI$^+$): 431.8; MS(ESI$^-$): 429.7.

Example 57

Formation of N-[3-(dimethylamino)propyl]-N-methyl-3-(5-methyl-2-phenyl-4,5,6,7-tetrahydro-1H-indol-1-yl)benzamide (57) (Compound according to Formula (I), Scheme 1)

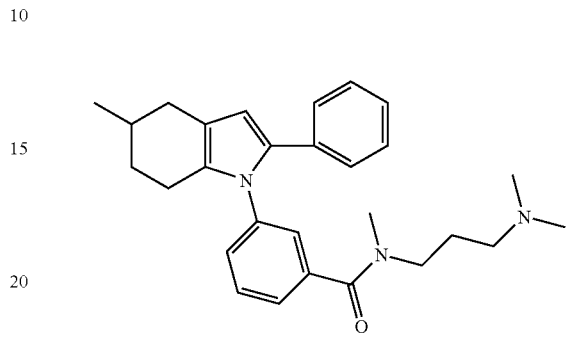

Following the general methods as outlined under Example 1, starting from 3-(5-methyl-2-phenyl-4,5,6,7-tetrahydro-1H-indol-1-yl)benzoic acid (Intermediate 18) and N,N,N'-trimethylpropane-1,3-diamine, the title compound (57) was isolated as a beige solid in 50% yield (98% purity by HPLC). MS(ESI$^+$): 430.8; MS(ESI$^-$): 428.7.

Example 58

Measurement of Levels of Reactive Oxygen Species in Different Cell Cultures

The activity of the compounds according to the invention may be tested for their activity in the inhibition or reduction of formation of reactive oxygen species (ROS) from oxygen in cells. The activity of the compounds is tested in the following cell cultures by different techniques such as nitroblue tetrazolium, Amplex Red, Chemiluminescence (Luminol) and 2',7'-dichlorodihydrofluorescein diacetate (H$_2$DCF-DA) according to the protocols detailed below.

Human Microglia Cell Line

Human microglia cell line (HMC$_3$, human microglia clone 3) (Janabi et al, 1995, *Neurosci Lett* 195:105) were cultured in MEM (Eagle's minimum essential medium) containing 10% FBS with 50 U/mL penicillin G sodium 50 µg/mL streptomycin sulfate, and incubated at 37° C. for 24 hours. IFN-γ (human IFN-γ, Roche. 11 040 596 001) was added to the culture medium for a final concentration of 10 ng/mL 24 h, before detection of O$_2^-$ formation.

Human Umbilical Vein Endothelial Cells (HUVEC)

HUVEC are cultured in endothelial basal medium supplemented with hydrocortisone (1 µg/mL, CalbioChem), bovine brain extract (12 µg/mL), gentamicin (50 µg/mL, CalbioChem), amphotericin B (50 ng/mL, CalBioChem EGF (10 ng/mL, and 10% FCS until the fourth passage. When the fifth passage was started, cells were cultured with a lower concentration of FCS (2%) in the absence of EGF, if not indicated otherwise. All experiments were done with cells of the fifth passage. The cells were incubated with OxLDL (oxidized low-density lipoprotein) or its buffer as control for 24 h, before detection of O$_2^-$ formation.

HL-60 Cells

Human acute myeloid leukemia cell line HL-60 was cultured in RPMI 1640 (Invitrogen) supplemented with 10% heat-inactivated calf serum, 2 mM glutamine, 100 U/mL penicillin (Sigma), and 100 µg streptomycin (Sigma) at 37° C. under a humidified atmosphere of 5% $CO_2$. HL60 differentiation to the neutrophil phenotype was triggered by adding $Me_2SO$ (final concentration 1.25% v/v for 6 days) to the culture medium.

1. Nitroblue Tetrazolium (NBT)

Intracellular and extracellular superoxide was measured by a colorimetric technique using a quantitative nitroblue tetrazolium (NBT) test. SOD-inhibitable conversion of NBT to formazan, a fine blue precipitate, in the presence of superoxide anion was measured using Fluostar Optima spectrometer (BMG labtech). Following incubation with appropriate stimuli, cells were trypsinized (1× Trypsin-EDTA), collected by centrifugation, and washed with PBS to remove medium. $5 \times 10^5$ cells were plated on 48-well plates and incubated in Hank's balanced salt solution containing 0.5 mg/mL NBT with or without 800 U/mL SOD in the presence or absence of compounds according to the invention. As a control, DPI was included at a final concentration of 10 µM. After 2.5 h, cells were fixed and washed with methanol to remove non reduced NBT. The reduced formazan was then dissolved in 230 µl of 2M potassium hydroxide and in 280 µl of dimethylsulfoxide. The absorption was measured at 630 nm. For calculation, the absorbance at 630 nm was normalized for each individual well. The mean of the four blank values was subtracted from each corrected value for each time point. NOX activities were expressed as % of the activity in control cells. Residual activity of DPI-treated cells was usually <10%.

2. Amplex Red

Extracellular hydrogen peroxide was measured using Amplex UltraRed (Molecular Probes). Cells were trypsinized (1× Trypsin-EDTA), collected by centrifugation, and resuspended in HBSS supplemented with 1% glucose. Cells were seeded into black 96-well plates at a density of 50'000 cells in 200 µl testing buffer (HBSS 1% glucose containing 0.005 U/mL horseradish peroxidase (Roche) and 50 µM Amplex Red in the presence or absence of compounds according to the invention. As a control, DPI was included at a final concentration of 10 µM The plates were placed in the fluorescent Optima Fluorescent plate reader and kept at 37° C. during 20 min. Fluorescence was measured for 15 min hours with excitation and emission wavelengths of 544 and 590 nm respectively. NOX activities were expressed as % of the activity in control cells. Residual activity of DPI-treated cells was usually <10%.

The table 1 below summarizes the percentage of inhibition of NOX activity as measured by Amplex Red using DMSO-differentiated HL60 cells as described above:

TABLE 1

| Compound n° | Inhibition (%) |
| --- | --- |
| (29) | 77 |
| (30) | 71 |
| (31) | 70 |
| (32) | 77 |
| (34) | 69 |

The Table 2 below summarizes the $IC_{50}$ of NOX activity as measured by Amplex Red using DMSO-differentiated HL60 cells as described above:

TABLE 2

| Compound n° | $IC_{50}$ (µM) |
| --- | --- |
| (1) | 2.9 |
| (3) | 3.2 |
| (4) | 2.9 |
| (5) | 2.8 |
| (6) | 1.6 |
| (9) | 2.6 |
| (10) | 3.1 |
| (12) | 1.9 |
| (13) | 2.9 |
| (17) | 8.6 |
| (28) | 7.9 |
| (45) | 2.9 |
| (46) | 4.3 |
| (49) | 6.0 |
| (51) | 6.2 |
| (53) | 6.3 |
| (54) | 2.1 |
| (55) | 7.4 |

3. Chemiluminescence (Luminol)

ROS was measured using the chemiluminescent probe luminol. Cells were cultured and plated as for Amplex Red except that the Amplex Red agent was replaced by 10 µg/mL luminol (Sigma 09235). Light emission was recorded continuously at 37° C. for 60 minutes using the luminescence function of the FluoStar Optima fluorescent plate reader. The mean of the four blank values was subtracted from each corrected value for each time point. NOX activities were expressed as % of the activity in control cells. Residual activity of DPI-treated cells was usually <10%.

4. 2',7'-dichlorodihydrofluorescein diacetate ($H_2DCF$-DA)

HUVEC were plated on coverslips and made quiescent overnight in 0.5% BSA before stimulation with TGF-β. Cells were loaded for 10 minutes with 5 µM CM-H2DCFDA in phenol-red-free medium in the dark and then treated with TGF-β (R&D Systems) in the presence or absence of compounds according to the invention. Cells were then visualized by immunofluorescence microscopy after fixation and staining of the nuclei with DAPI or examined live using confocal microscopy. DCF fluorescence was visualized at an excitation wavelength of 488 nm and emission at 515 to 540 nm. To avoid photo-oxidation of the indicator dye, images were collected with a single rapid scan using identical parameters for all samples. For calculation, the absorbance at 540 nm was normalized to absorbance at 540 nm for each individual well. The mean of the four blank values was subtracted from each corrected value for each time point. NOX activities were expressed as % of the activity in control cells. Residual activity of DPI-treated cells was usually <10%.

The invention claimed is:

1. A method for the treatment of a disease or condition selected from cardiovascular diseases, respiratory disorders, disorders affecting the metabolism, skin and/or bone diseases, kidney diseases, reproduction disorders, inflammatory disorders, allergic disorders, traumatisms, septic, hemorrhagic and anaphylactic shock, cancers, diseases or disorders of the gastrointestinal system and other diseases and/or disorders associated with Nicotinamide adenine dinucleotide phosphate oxidase (NADPH Oxidase) catalyzed production of reactive oxygen species (ROS) comprising administering a tetrahydroindole derivative according to Formula (I) in a patient having a disease or condition selected from cardiovascular diseases, respiratory disorders, disorders affecting the metabolism, skin and/or bone diseases, kidney diseases, reproduction disorders, inflammatory disorders, allergic disorders, traumatisms, septic, hemorrhagic and anaphylactic shock, cancers, diseases or disorders of the gastrointestinal system and other diseases and/or disorders associated with Nicotinamide adenine dinucleotide phosphate oxidase (NADPH Oxidase) catalyzed production of reactive oxygen species (ROS):

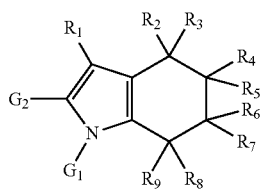

wherein $G_1$ is selected from the following groups:

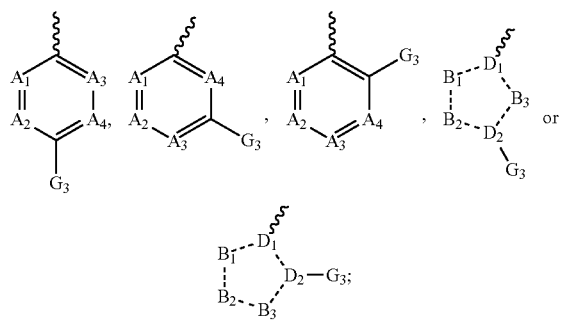

$G_2$ is selected from optionally substituted alkyl, optionally substituted aryl, optionally substituted heteroaryl, optionally substituted $C_3$-$C_8$-cycloalkyl or optionally substituted heterocycloalkyl;

$G_3$ is —C(O)NR$^{13}$R$^{14}$;

$A_1$, $A_2$, $A_3$ and $A_4$ are independently selected from CR$^{10}$ or N;

$B_1$, $B_2$ and $B_3$ are independently selected from NR$^{11}$, O, CR$^{11}$R$^{12}$ or S;

$D_1$ and $D_2$ are CR$^{11}$;

$R^1$, $R^2$, $R^3$, $R^4$, $R^5$, $R^6$, $R^7$, $R^8$ and $R^9$ are independently selected from H, halogen, optionally substituted alkyl, optionally substituted alkenyl, optionally substituted alkynyl, optionally substituted aryl, optionally substituted heteroaryl, optionally substituted $C_3$-$C_8$-cycloalkyl, optionally substituted heterocycloalkyl, optionally substituted heteroalkyl, OH; NH$_2$, NHR$^{15}$, NHCOR$^{15}$, NHSO$_2$R$^{15}$, SR$^{15}$, S(O)R$^{15}$, SO$_2$R$^{15}$, CO$_2$H or CONHR$^{15}$;

$R^{10}$ is selected from H; halogen, OH, O-alkyl, NH-Alkyl, N(Alkyl)$_2$, or optionally substituted alkyl;

$R^{11}$ and $R^{12}$ can be independently absent or when present are selected from H; halogen, optionally substituted alkyl, optionally substituted alkenyl or optionally substituted alkynyl;

$R^{13}$ and $R^{14}$ are independently selected from H; optionally substituted alkyl, optionally substituted alkenyl, optionally substituted alkynyl, optionally substituted amino alkyl, optionally substituted $C_3$-$C_8$-cycloalkyl, optionally substituted heterocycloalkyl, optionally substituted aryl, optionally substituted heteroaryl, optionally substituted alkyl aryl, optionally substituted alkyl heteroaryl, optionally substituted aryl alkyl, optionally substituted heteroaryl alkyl, optionally substituted alkyl $C_3$-$C_8$-cycloalkyl, optionally substituted alkyl heterocycloalkyl, optionally substituted $C_3$-$C_8$-cycloalkyl alkyl or optionally substituted heterocycloalkyl alkyl;

$R^{15}$ is selected from H, optionally substituted alkyl, optionally substituted alkenyl, optionally substituted alkynyl, optionally substituted $C_3$-$C_8$-cycloalkyl, optionally substituted heterocycloalkyl, optionally substituted aryl, optionally substituted heteroaryl, optionally substituted alkyl aryl, optionally substituted alkyl heteroaryl, optionally substituted aryl alkyl, optionally substituted heteroaryl alkyl, optionally substituted alkyl $C_3$-$C_8$-cycloalkyl, optionally substituted alkyl heterocycloalkyl, optionally substituted $C_3$-$C_8$-cycloalkyl alkyl or optionally substituted heterocycloalkyl alkyl; "-----" is selected from a single or double bond;

and pharmaceutically acceptable salts or pharmaceutically active derivatives and tautomers thereof.

2. The method according to claim 1 wherein $G_1$ is:

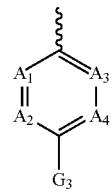

wherein $G_2$, $G_3$, $R^1$, $R^2$, $R^3$, $R^4$, $R^5$, $R^6$, $R^7$, $R^8$, $R^9$, $R^{13}$, $R^{14}$ and $R^{15}$ are as defined in claim 1; $A_1$, $A_2$, $A_3$ and $A_4$ are CH.

3. The method according to claim 1 wherein $G_1$ is:

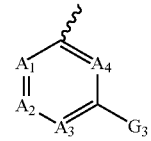

and wherein $G_2$, $G_3$, $R^1$, $R^2$, $R^3$, $R^4$, $R^5$, $R^6$, $R^7$, $R^8$, $R^9$, $R^{13}$, $R^{14}$ and $R^{15}$ are as defined in claim 1; $A_1$, $A_2$, $A_3$ and $A_4$ are CH.

4. The method according to claim 1 wherein $G_1$ is selected from:

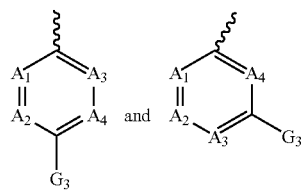

and wherein $G_2$, $G_3$, $R^1$, $R^2$, $R^3$, $R^4$, $R^5$, $R^6$, $R^7$, $R^8$, $R^9$, $R^{13}$, $R^{14}$ and $R^{15}$ are as defined in claim 22; at least one among $A_1$, $A_2$, $A_3$ and $A_4$ is N.

5. The method according to claim 1 wherein $G_1$ is selected from the following groups:

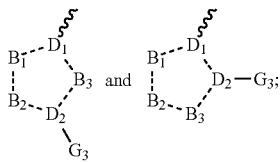

$G_2$, $G_3$, $B_1$, $B_2$, $B_3$, $D_1$, $D_2$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$ and $R^{15}$ are as defined in claim 1.

6. The method according to claim 1 wherein $G_2$ is selected from aryl or heteroaryl.

7. The method according to claim 1 wherein $G_2$ is alkyl.

8. The method according to claim 1 wherein $R^2$, $R^3$, $R^5$, $R^6$, $R^7$, $R^8$ and $R^9$ are H.

9. The method according to claim 1 wherein $R^1$ and $R^4$ are selected from H or alkyl.

10. The method according to claim 1 wherein $R^{13}$ is optionally substituted amino alkyl.

11. The method according to claim 1 wherein $R^{13}$ is selected from optionally substituted $C_3$-$C_8$-cycloalkyl alkyl or optionally substituted heterocycloalkyl alkyl.

12. The method according to claim 1 wherein $R^{14}$ is H.

13. The method according to claim 1 wherein $R^{14}$ is alkyl.

14. The method according to claim 1 wherein the tetrahydroindole derivative is selected from:
N-[2-(2-methylpiperidin-1-yl)ethyl]-4-(2-phenyl-4,5,6,7-tetrahydro-1H-indol-1-yl)benzamide;
N-[3-(2-methylpiperidin-1-yl)propyl]-4-(2-phenyl-4,5,6,7-tetrahydro-1H-indol-1-yl)benzamide;
N-[3-(4-ethylpiperazin-1-yl)propyl]-4-(2-phenyl-4,5,6,7-tetrahydro-1H-indol-1-yl)benzamide;
N-[3-(dibutylamino)propyl]-4-(2-phenyl-4,5,6,7-tetrahydro-1H-indol-1-yl)benzamide;
4-(5-methyl-2-phenyl-4,5,6,7-tetrahydro-1H-indol-1-yl)-N-[3-(4-propylpiperazin-1-yl) propyl]benzamide;
N-{3-[cyclohexyl(methyl)amino]propyl}-4-(2-phenyl-4,5,6,7-tetrahydro-1H-indol-1-yl)benzamide;
4-(2-phenyl-4,5,6,7-tetrahydro-1H-indol-1-yl)-N-[3-(4-propylpiperazin-1-yl)propyl]benzamide;
N-[3-(2-ethylpiperidin-1-yl)propyl]-4-(2-phenyl-4,5,6,7-tetrahydro-1H-indol-1-yl)benzamide;
N-(3-azepan-1-ylpropyl)-4-(2-phenyl-4,5,6,7-tetrahydro-1H-indol-1-yl)benzamide;
N-[3-(2,6-dimethylpiperidin-1-yl)propyl]-4-(2-phenyl-4,5,6,7-tetrahydro-1H-indol-1-yl)benzamide;
N-{2-[cyclohexyl(methyl)amino]ethyl}-4-(5-methyl-2-phenyl-4,5,6,7-tetrahydro-1H-indol-1-yl)benzamide;
N-{3-[butyl(methyl)amino]propyl}-4-(2-phenyl-4,5,6,7-tetrahydro-1H-indol-1-yl)benzamide;
N-[(1-ethylpyrrolidin-2-yl)methyl]-4-(2-phenyl-4,5,6,7-tetrahydro-1H-indol-1-yl)benzamide;
4-(5-methyl-2-phenyl-4,5,6,7-tetrahydro-1H-indol-1-yl)-N-[2-(4-methylpiperazin-1-yl)ethyl]benzamide;
N-{2-[cyclohexyl(methyl)amino]ethyl}-4-(2-phenyl-4,5,6,7-tetrahydro-1H-indol-1-yl)benzamide;
4-(2-phenyl-4,5,6,7-tetrahydro-1H-indol-1-yl)-N-(3-piperidin-1-ylpropyl)benzamide;
N-[3-(4-benzylpiperidin-1-yl)propyl]-4-(2,5-dimethyl-4,5,6,7-tetrahydro-1H-indol-1-yl)benzamide;
N-[3-(dipropylamino)propyl]-4-(2-phenyl-4,5,6,7-tetrahydro-1H-indol-1-yl)benzamide;
4-(2-phenyl-4,5,6,7-tetrahydro-1H-indol-1-yl)-N-(3-pyrrolidin-1-ylpropyl)benzamide;
N-[2-(diethylamino)ethyl]-4-(2-phenyl-4,5,6,7-tetrahydro-1H-indol-1-yl)benzamide;
4-(2,5-dimethyl-4,5,6,7-tetrahydro-1H-indol-1-yl)-N-[3-(2-methylpiperidin-1-yl) propyl]benzamide;
N-[3-(3,5-dimethylpiperidin-1-yl)propyl]-4-(2-phenyl-4,5,6,7-tetrahydro-1H-indol-1-yl)benzamide;
N-[3-(4-benzylpiperidin-1-yl)propyl]-4-(2,5-dimethyl-4,5,6,7-tetrahydro-1H-indol-1-yl)benzamide;
N-[3-(3,5-dimethylpiperidin-1-yl)propyl]-4-(2,5-dimethyl-4,5,6,7-tetrahydro-1H-indol-1-yl)benzamide;
N-(2-azepan-1-ylethyl)-4-(2-phenyl-4,5,6,7-tetrahydro-1H-indol-1-yl)benzamide;
N-[3-(2,6-dimethylpiperidin-1-yl)propyl]-4-(2,5-dimethyl-4,5,6,7-tetrahydro-1H-indol-1-yl)benzamide;
N-[3-(4-benzylpiperidin-1-yl)propyl]-4-(2-methyl-4,5,6,7-tetrahydro-1H-indol-1-yl)benzamide;
N-{3-[benzyl(ethyl)amino]propyl}-4-(2-methyl-4,5,6,7-tetrahydro-1H-indol-1-yl)benzamide;
N-[3-(2-ethylpiperidin-1-yl)propyl]-4-(2-methyl-4,5,6,7-tetrahydro-1H-indol-1-yl)benzamide;
4-(5-methyl-2-phenyl-4,5,6,7-tetrahydro-1H-indol-1-yl)-N-(2-morpholin-4-ylethyl)benzamide;
N-(3-morpholin-4-ylpropyl)-4-(2-phenyl-4,5,6,7-tetrahydro-1H-indol-1-yl)benzamide;
4-(2,5-dimethyl-4,5,6,7-tetrahydro-1H-indol-1-yl)-N-[(1-ethylpyrrolidin-2-yl)methyl]benzamide;
N-{3-[cyclohexyl(methyl)amino]propyl}-4-(2-methyl-4,5,6,7-tetrahydro-1H-indol-1-yl)benzamide;
N-[3-(diethylamino)propyl]-4-(2,5-dimethyl-4,5,6,7-tetrahydro-1H-indol-1-yl)benzamide;
N-[3-(3,5-dimethylpiperidin-1-yl)propyl]-4-(2-methyl-4,5,6,7-tetrahydro-1H-indol-1-yl)benzamide;
N-{2-[cyclohexyl(methyl)amino]ethyl}-4-(2-methyl-4,5,6,7-tetrahydro-1H-indol-1-yl)benzamide;
N-{2-[butyl(ethyl)amino]ethyl}-4-(2-methyl-4,5,6,7-tetrahydro-1H-indol-1-yl)benzamide;
N-{2-(diethylamino)ethyl}-4-(2-methyl-4,5,6,7-tetrahydro-1H-indol-1-yl)benzamide;
4-(2-methyl-4,5,6,7-tetrahydro-1H-indol-1-yl)-N-(3-piperidin-1-ylpropyl)benzamide;
N-{2-[butyl(ethyl)amino]ethyl}-4-(2-phenyl-4,5,6,7-tetrahydro-1H-indol-1-yl)benzamide;
N-[3-(dimethylamino)propyl]-N-methyl-4-[5-methyl-2-(1-methyl-1H-benzimidazol-2-yl)-4,5,6,7-tetrahydro-1H-indol-1-yl]benzamide;
N-[2-(dimethylamino)ethyl]-4-(5-methyl-2-phenyl-4,5,6,7-tetrahydro-1H-indol-1-yl)benzamide;
N-[4-(diethylamino)-1-methylbutyl]-4-(5-methyl-2-phenyl-4,5,6,7-tetrahydro-1H-indol-1-yl)benzamide;
N-[3-(dimethylamino)propyl]-N-methyl-4-(5-methyl-2-phenyl-4,5,6,7-tetrahydro-1H-indol-1-yl)benzamide;
N-{2-[cyclohexyl(methyl)amino]ethyl}-(5-methyl-2-phenyl-4,5,6,7-tetrahydro-1H-indol-1-yl)benzamide;
N-{2-[cyclohexyl(methyl)amino]ethyl}-4-(5-methyl-2-pyridin-2-yl-4,5,6,7-tetrahydro-1H-indol-1-yl)benzamide;
N-{3-[cyclohexyl(methyl)amino]propyl}-4-(5-methyl-2-phenyl-4,5,6,7-tetrahydro-1H-indol-1-yl)benzamide;
N-[2-(dimethylamino)ethyl]-4-(5-methyl-2-pyridin-3-yl-4,5,6,7-tetrahydro-1H-indol-1-yl)benzamide;
N-[3-(dimethylamino)propyl]-N-methyl-4-(5-methyl-2-pyridin-2-yl-4,5,6,7-tetrahydro-1H-indol-1-yl)benzamide;

N-[3-(dimethylamino)propyl]-N-methyl-4-(5-methyl-2-pyridin-3-yl-4,5,6,7-tetrahydro-1H-indol-1-yl)benzamide;

N-[3-(dimethylamino)propyl]-N-methyl-2-(5-methyl-2-phenyl-4,5,6,7-tetrahydro-1H-indol-1-yl)-1,3-thiazole-4-carboxamide;

N-[3-(dimethylamino)propyl]-N-methyl-5-(5-methyl-2-phenyl-4,5,6,7-tetrahydro-1H-indol-1-yl)pyridine-2-carboxamide;

N-[3-(dimethylamino)propyl]-N-methyl-5-(5-methyl-2-phenyl-4,5,6,7-tetrahydro-1H-indol-1-yl)pyridine-3-carboxamide;

N-[3-(dimethylamino)propyl]-N-methyl-4-[5-methyl-2-(3-oxo-3,4-dihydro-2H-1,4-benzoxazin-6-yl)-4,5,6,7-tetrahydro-1H-indol-1-yl]benzamide;

N-[3-(dimethylamino)propyl]-N-methyl-4-[5-methyl-2-(1,3-thiazol-2-yl)-4,5,6,7-tetrahydro-1H-indol-1-yl]benzamide;

N-[3-(dimethylamino)propyl]-N-methyl-6-(5-methyl-2-phenyl-4,5,6,7-tetrahydro-1H-indol-1-yl)pyridine-3-carboxamide; or N-[3-(dimethylamino)propyl]-N-methyl-3-(5-methyl-2-phenyl-4,5,6,7-tetrahydro-1H-indol-1-yl)benzamide.

15. The method according to claim 5, wherein said disease or condition is a respiratory disorder.

16. The method according to claim 15, wherein said respiratory disorder is selected from bronchial asthma, bronchitis, allergic rhinitis, adult respiratory syndrome, cystic fibrosis, lung viral infection (influenza), pulmonary hypertension or chronic obstructive pulmonary diseases (COPD).

17. The method according to claim 16, wherein said respiratory disorder is pulmonary hypertension.

18. A method for the treatment of a neuromuscular degenerative disease comprising administering to a patient suffering from a neuromuscular degenerative disease a tetrahydroindole derivative according to Formula (I)

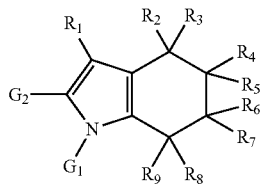

wherein $G_1$ is selected from:

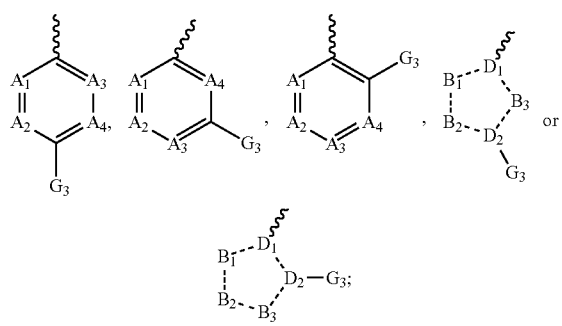

$G_2$ is selected from optionally substituted alkyl, optionally substituted aryl, optionally substituted heteroaryl, optionally substituted $C_3$-$C_8$-cycloalkyl or optionally substituted heterocycloalkyl;

$G_3$ is —C(O)NR$^{13}$R$^{14}$;

$A_1$, $A_2$, $A_3$ and $A_4$ are independently selected from CR$^{10}$ or N;

$B_1$, $B_2$ and $B_3$ are independently selected from NR$^{11}$, O, CR$^{11}$R$^{12}$ or S;

$D_1$ and $D_2$ are CR$^{11}$;

$R^1$, $R^2$, $R^3$, $R^4$, $R^5$, $R^6$, $R^7$, $R^8$ and $R^9$ are independently selected from H, halogen, optionally substituted alkyl, optionally substituted alkenyl, optionally substituted alkynyl, optionally substituted aryl, optionally substituted heteroaryl, optionally substituted $C_3$-$C_8$-cycloalkyl, optionally substituted heterocycloalkyl, optionally substituted heteroalkyl, OH; NH$_2$, NHR$^{15}$, NHCOR$^{15}$', NHSO$_2$R$^{15}$, SR$^{15}$, S(O)R$^{15}$, SO$_2$R$^{15}$, CO$_2$H or CONHR$^{15}$;

$R^{10}$ is selected from H; halogen, OH, O-alkyl, NH-Alkyl, N(Alkyl)$_2$, or optionally substituted alkyl;

$R^{11}$ and $R^{12}$ can be independently absent or when present are selected from H; halogen, optionally substituted alkyl, optionally substituted alkenyl and optionally substituted alkynyl;

$R^{13}$ is selected from optionally substituted amino alkyl, substituted $C_3$-$C_8$-cycloalkyl or optionally substituted heterocycloalkyl;

$R^{14}$ is selected from H; optionally substituted alkyl, optionally substituted alkenyl, optionally substituted alkynyl, optionally substituted amino alkyl, optionally substituted $C_3$-$C_8$-cycloalkyl, optionally substituted heterocycloalkyl, optionally substituted aryl, optionally substituted heteroaryl, optionally substituted alkyl aryl, optionally substituted alkyl heteroaryl, optionally substituted aryl alkyl, optionally substituted heteroaryl alkyl, optionally substituted alkyl $C_3$-$C_8$-cycloalkyl, optionally substituted alkyl heterocycloalkyl, optionally substituted $C_3$-$C_8$-cycloalkyl alkyl or optionally substituted heterocycloalkyl alkyl;

$R^{15}$ is selected from H, optionally substituted alkyl, optionally substituted alkenyl, optionally substituted alkynyl, optionally substituted $C_3$-$C_8$-cycloalkyl, optionally substituted heterocycloalkyl, optionally substituted aryl, optionally substituted heteroaryl, optionally substituted alkyl aryl, optionally substituted alkyl heteroaryl, optionally substituted aryl alkyl, optionally substituted heteroaryl alkyl, optionally substituted alkyl $C_3$-$C_8$-cycloalkyl, optionally substituted alkyl heterocycloalkyl, optionally substituted $C_3$-$C_8$-cycloalkyl alkyl or optionally substituted heterocycloalkyl alkyl;

"-----" is selected from a single or double bond;

and pharmaceutically acceptable salts or pharmaceutically active derivatives and tautomers thereof.

19. The method according to claim 5, wherein said cardiovascular disorder is cardiovascular complications of Type I or Type II diabetes, intimal hyperplasia, coronary heart disease, cerebral, coronary or arterial vasospasm, endothelial dysfunction, heart failure, peripheral artery disease, restenosis, trauma caused by a stent, stroke, ischemic attack, vascular complications after organ transplantation, viral or bacterial infections, myocardial infarction, platelet aggregation, angina pectoris, aneurysm, aortic dissection, ischemic heart disease, cardiac hypertrophy, pulmonary embolus, thrombotic events, injury caused after ischemia by restoration of blood flow or oxygen delivery in organ transplantation, open heart surgery, angioplasty, hemorrhagic shock, or angioplasty of ischemic organs.

20. The method according to claim 5, wherein said metabolism disorder is obesity, metabolic syndrome or Type II diabetes.

21. The method according to claim 5, wherein said bone disorder is osteoporosis, osteoporasis, osteosclerosis, periodontitis, or hyperparathyroidism.

22. The method according to claim 5, wherein said kidney disorder is diabetic nephropathy, renal failure, glomerulonephritis, nephrotoxicity of aminoglycosides and platinum compounds or hyperactive bladder.

23. The method according to claim 5, wherein said inflammatory disorder is inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, cystic fibrosis, stroke, acute bronchitis, chronic bronchitis, acute bronchiolitis, chronic bronchiolitis, osteoarthritis, gout, myelitis, ankylosing spondylitis, Reuter syndrome, psoriatic arthritis, spondylarthritis, juvenile arthritis, juvenile ankylosing spondylitis, reactive arthritis, gonococcal arthritis, tuberculous arthritis, viral arthritis, bacterial arthritis, syphilitic arthritis, Lyme disease, polyarteritis nodosa, anaphylactic angiitis, Luegenec granulomatosis, rheumatoid polymyalgia, articular cell rheumatism, calcium crystal deposition arthritis, pseudogout, non-arthritic rheumatism, bursitis, tendosynovitis, epicondyle inflammation (tennis elbow), carpal tunnel syndrome, mixed form of arthritis, neuropathic arthropathy, hemorrhagic arthritis, vascular peliosis, hypertrophic osteoarthropathy, multicentric reticulohistiocytosis, arthritis induced by specific diseases, blood pigmentation, sickle cell disease and other hemoglobin abnormality, hyperlipoproteinemia, dysgammaglobulinemia, hyperparathyroidism, acromegaly, familial Mediterranean fever, Bechet's disease, systemic autoimmune disease erythematosus, multiple sclerosis, Crohn's disease or chronic inflammatory bowel diseases (IBD).

24. The method according to claim 5, wherein said liver disorder is liver fibrosis, alcohol induced fibrosis, steatosis or non-alcoholic steatohepatitis.

25. The method according to claim 5, wherein said disease or disorder is pulmonary hypertension.

* * * * *

UNITED STATES PATENT AND TRADEMARK OFFICE
CERTIFICATE OF CORRECTION

Page 1 of 4

PATENT NO. : 8,288,432 B2
APPLICATION NO. : 12/532567
DATED : October 16, 2012
INVENTOR(S) : Patrick Page et al.

It is certified that error appears in the above-identified patent and that said Letters Patent is hereby corrected as shown below:

Title Page,
(75) Inventors, "Patrick Page, Savonni (FR)" should read
--Patrick Page, Saint-Julien-en-Genevois (FR);--.

In the Specification:

Column 3,
Line 35, "cancers, a diseases or" should read --cancers, diseases or--.
Line 42, "wherein d," should read --wherein $G_1$,--.
Line 43, "$A_1$; $A_2$," should read --$A_1$, $A_2$,--.
Line 54, "cancers, a diseases or" should read --cancers, diseases or--.
Line 65, "cancers, a diseases or" should read --cancers, diseases or--.

Column 4,
Line 35, "$A_3$, $A_1$," should read --$A_3$, $A_4$,--.
Line 35, "$R^7$, $R^5$," should read --$R^7$, $R^8$,--.
Line 64, "$R^7$, $R^5$," should read --$R^7$, $R^8$,--.

Column 5,
Lines 15-16, "cancers, a diseases or" should read --cancers, diseases or--.

Column 6,
Line 5, "include $C_2$-$C_6$" should read --include $C_2$-$C_8$--.
Line 44, "to an aryl groups" should read --to aryl groups--.
Line 46, "to an alkenyl groups" should read --to alkenyl groups--.

Column 7,
Line 18, "to alkyl" should read --refers to alkyl--.

Signed and Sealed this
Seventeenth Day of December, 2013

Margaret A. Focarino
*Commissioner for Patents of the United States Patent and Trademark Office*

CERTIFICATE OF CORRECTION (continued)

Column 9,
Line 59, "formed from to acid" should read --formed from acid--.

Column 11,
Line 20, "calcium ciystal" should read --calcium crystal--.

Column 12,
Lines 18-19, "For examples," should read --For example,--.
Line 24, "inhibit or reduce" should read --inhibits or reduces--.
Line 37, "cancers, a diseases or" should read --cancers, diseases or--.

Column 14,
Line 28, "are administered" should read --is administered--.

Column 17,
Line 1, "cancers, a diseases or" should read --cancers, diseases or--.
Line 20, "cancers, a diseases or" should read --cancers, diseases or--.
Line 32, "cancers, a diseases or" should read --cancers, diseases or--.

Column 18,
Line 43, "$G_3 > R^1$," should read --$G_3$, $R^1$,--.

Column 20,
Lines 58-67,

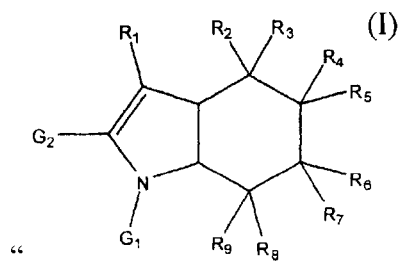 " should read -- 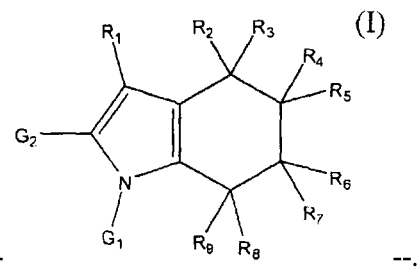 --.

Column 21,
Lines 22-29,

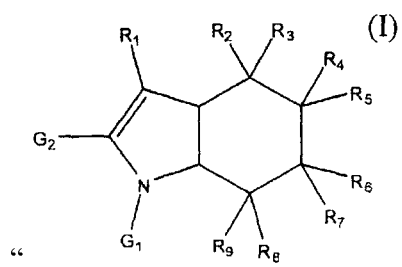 " should read -- 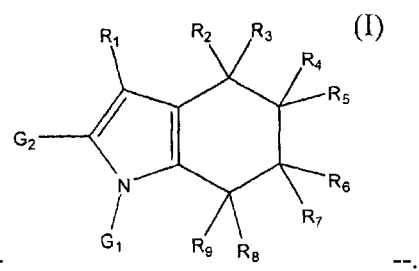 --.

CERTIFICATE OF CORRECTION (continued)
U.S. Pat. No. 8,288,432 B2

Column 21,
Lines 50-58,

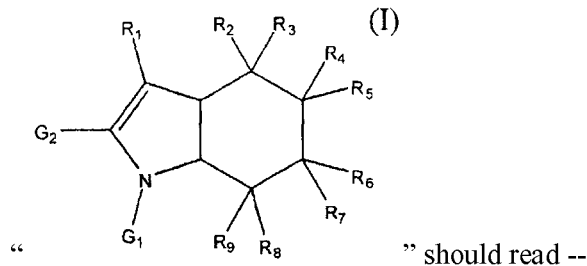 " should read -- 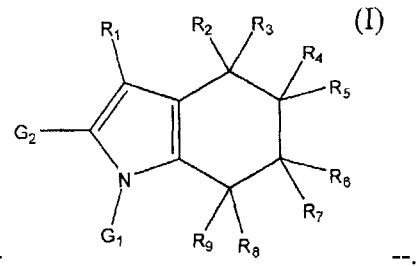 --.

Column 22,
Lines 5-11,

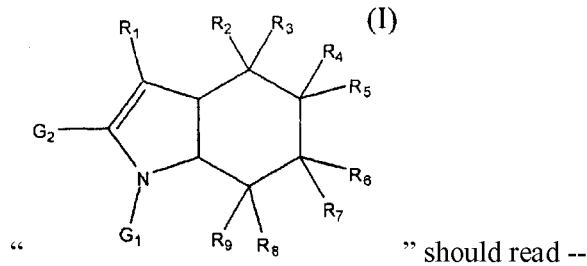 " should read -- 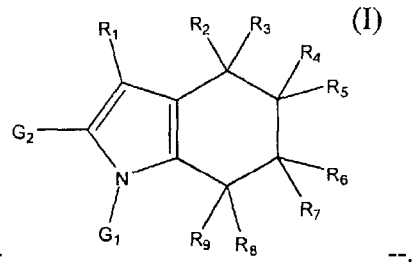 --.

Line 30, "$D_1$; $D_2$," should read --$D_1$, $D_2$,--.

Column 22,
Lines 49-56,

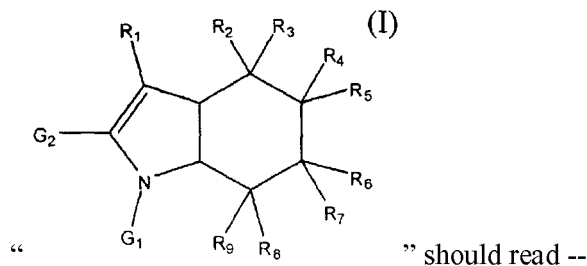 " should read -- 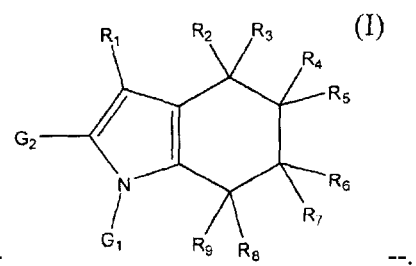 --.

Column 26,
Line 37, "6,7-tetrahydro-4H-indol-1-yl)benzamide" should read
--6,7-tetrahydro-1H-indol-1-yl)benzamide--.

Column 28,
Line 17, "in then entirety." should read --in their entirety.--.
Line 36, "starting L5 materials" should read --starting materials--.

CERTIFICATE OF CORRECTION (continued)
U.S. Pat. No. 8,288,432 B2

Column 41,
Lines 8-9, "4,5,6,7-tetrahydro-4H-indol-1-yl)pyridine-3-carboxylic acid" should read
--4,5,6,7-tetrahydro-1H-indol-1-yl)pyridine-3-carboxylic acid--.

Column 43,
Line 41, "3(4-propyl" should read --3-(4-propyl--.

Column 45,
Line 4, "(2-phenyl)-" should read --(2-phenyl- --.

Column 47,
Line 32, "70%> yield" should read --70% yield--.

Column 66,
Line 45, "(HMC$_3$," should read --(HMC3,--.

In the Claims:

Column 70,
Line 66, "defined in claim 22" should read --defined in claim 1--.

Column 72,
Line 41, "N-{2-(diethylamino)ethyl}-4-(2-methyl-4,5,6,7-tetrahydro-1II-indol-1-yl)benzamide;" should read
--N-[2-(diethylamino)ethyl]-4-(2-methyl-4,5,6,7-tetrahydro-1H-indol-1-yl)benzamide;--.